(12) United States Patent
Aronson et al.

(10) Patent No.: US 7,712,976 B2
(45) Date of Patent: May 11, 2010

(54) ACTIVE OPTICAL CABLE WITH INTEGRATED RETIMING

(75) Inventors: Lewis B. Aronson, Los Altos, CA (US);
Greta Light, San Mateo, CA (US);
The-Linh Nguyen, San Jose, CA (US);
Darin J. Douma, Monrovia, CA (US)

(73) Assignee: Finisar Corporation, Sunnyvale, CA (US)

( * ) Notice: Subject to any disclaimer, the term of this patent is extended or adjusted under 35 U.S.C. 154(b) by 0 days.

(21) Appl. No.: 11/402,169

(22) Filed: Apr. 10, 2006

(65) Prior Publication Data
US 2007/0237471 A1    Oct. 11, 2007

(51) Int. Cl.
G02B 6/36 (2006.01)
G02B 6/12 (2006.01)
G02B 6/38 (2006.01)
G02B 6/44 (2006.01)
G02B 6/00 (2006.01)
H04B 10/00 (2006.01)
H04B 10/04 (2006.01)

(52) U.S. Cl. .............. 385/89; 385/14; 385/53; 385/54; 385/55; 385/70; 385/75; 385/76; 385/77; 385/88; 385/90; 385/100; 385/101; 385/102; 385/139; 398/155; 398/159; 398/193; 398/194

(58) Field of Classification Search ........ 385/53–94, 385/100–102, 14, 139; 398/155, 159, 193, 398/194
See application file for complete search history.

(56) References Cited

U.S. PATENT DOCUMENTS

| | | | |
|---|---|---|---|
| 3,663,822 A | 5/1972 | Uchida | |
| 3,792,284 A | 2/1974 | Kaelin | |
| 4,427,879 A * | 1/1984 | Becher et al. | 250/215 |
| 4,595,839 A | 6/1986 | Braun et al. | |
| 4,768,188 A * | 8/1988 | Barnhart et al. | 370/434 |
| 4,902,092 A | 2/1990 | Grandy | |
| 5,064,299 A | 11/1991 | Hirschmann et al. | |
| 5,166,761 A | 11/1992 | Olson et al. | |
| 5,337,398 A | 8/1994 | Benzoni et al. | |

(Continued)

FOREIGN PATENT DOCUMENTS

JP   07-210644   8/1995

(Continued)

OTHER PUBLICATIONS

Fiedler et al. ("A 1.0625 Gbps Transceiver with 2x-Oversampling and Transmit Signal Pre-Emphasis", ISSCC97/ Session 15/ Serial Data Communication/ Paper FP 15.1).*

(Continued)

*Primary Examiner*—Brian M. Healy
*Assistant Examiner*—Hung Lam
(74) *Attorney, Agent, or Firm*—Workman Nydegger

(57) ABSTRACT

An active cable that is configured to communicate over much of its length using one or more optical fibers, and that includes an integrated electrical connector at least one end. The active cable includes an integrated retiming mechanism. Thus, multiple links of cable may be used while reducing the chance that the jitter will exceed allowable limits. The cable may be an electrical to optical cable, and electrical to electrical cable, or one of many other potential configurations.

21 Claims, 40 Drawing Sheets

U.S. PATENT DOCUMENTS

| | | |
|---|---|---|
| 5,341,086 A | 8/1994 | Fukudome |
| 5,448,661 A | 9/1995 | Takai et al. |
| 5,497,187 A | 3/1996 | Banker et al. |
| 5,515,467 A | 5/1996 | Webb ........................ 385/88 |
| 5,530,787 A | 6/1996 | Arnett |
| 5,631,988 A | 5/1997 | Swirhun et al. |
| 5,668,419 A | 9/1997 | Oktay |
| 5,732,176 A | 3/1998 | Savage, Jr. |
| 5,892,784 A | 4/1999 | Tan et al. |
| 5,907,569 A | 5/1999 | Glance et al. |
| 5,926,303 A | 7/1999 | Giebel et al. |
| 6,036,654 A | 3/2000 | Quinn et al. |
| 6,115,516 A | 9/2000 | Watson et al. |
| 6,179,627 B1 | 1/2001 | Daly et al. |
| 6,217,231 B1 | 4/2001 | Mesaki et al. |
| 6,220,873 B1 | 4/2001 | Samela et al. |
| 6,267,606 B1 | 7/2001 | Poplawski et al. |
| 6,446,867 B1 | 9/2002 | Sanchez |
| 6,458,619 B1 | 10/2002 | Irissou |
| 6,461,059 B2 | 10/2002 | Ando et al. |
| 6,478,625 B2 | 11/2002 | Tolmie et al. |
| 6,502,997 B1 * | 1/2003 | Lee et al. ................ 385/88 |
| 6,515,308 B1 | 2/2003 | Kneissl et al. |
| 6,539,147 B1 | 3/2003 | Mahony |
| 6,540,412 B2 | 4/2003 | Yonemura et al. |
| 6,553,166 B1 | 4/2003 | Caldwell |
| 6,588,942 B1 | 7/2003 | Weld |
| 6,607,307 B2 | 8/2003 | Gilliland et al. |
| 6,717,972 B2 | 4/2004 | Steinle et al. |
| 6,755,575 B2 | 6/2004 | Kronlund |
| 6,758,693 B2 | 7/2004 | Inagaki et al. |
| 6,774,348 B2 | 8/2004 | Tatum et al. |
| 6,793,539 B1 | 9/2004 | Lee et al. |
| 6,806,114 B1 | 10/2004 | Lo |
| 6,822,987 B2 | 11/2004 | Diaz et al. |
| 6,905,257 B2 | 6/2005 | Eichenberger et al. |
| 6,912,361 B2 * | 6/2005 | Aronson et al. ............ 398/135 |
| 6,914,637 B1 | 7/2005 | Wolf et al. |
| 6,920,161 B2 | 7/2005 | Riaziat et al. |
| 6,941,395 B1 | 9/2005 | Galang et al. |
| 6,952,395 B1 | 10/2005 | Manoharan et al. |
| 6,954,592 B2 | 10/2005 | Tan et al. |
| 6,965,722 B1 | 11/2005 | Nguyen ........................ 385/147 |
| 7,062,171 B2 | 6/2006 | Ota et al. |
| 7,065,604 B2 | 6/2006 | Konda et al. |
| 7,070,425 B2 | 7/2006 | Regen et al. |
| 7,088,518 B2 | 8/2006 | Tatum et al. |
| 7,153,039 B2 | 12/2006 | McGarvey et al. |
| 7,154,921 B2 | 12/2006 | Kitamura et al. |
| 7,162,130 B2 | 1/2007 | Castellani et al. |
| 7,170,097 B2 | 1/2007 | Edmond et al. |
| 7,179,329 B2 | 2/2007 | Boone et al. |
| 7,217,022 B2 | 5/2007 | Ruffin |
| 7,269,194 B2 | 9/2007 | Diaz et al. |
| 7,269,673 B2 | 9/2007 | Kim et al. |
| 7,277,620 B2 | 10/2007 | Vongseng et al. |
| 7,371,014 B2 | 5/2008 | Willis et al. |
| 7,373,069 B2 | 5/2008 | Lazo |
| 7,401,985 B2 | 7/2008 | Aronson et al. |
| 7,445,389 B2 | 11/2008 | Aronson |
| 2001/0035994 A1 | 11/2001 | Agazzi et al. |
| 2002/0018609 A1 | 2/2002 | Schumann |
| 2002/0044746 A1 | 4/2002 | Kronlund et al. ............ 385/53 |
| 2002/0049879 A1 | 4/2002 | Eyer |
| 2002/0063935 A1 | 5/2002 | Price et al. |
| 2002/0076157 A1 | 6/2002 | Kropp |
| 2002/0114590 A1 * | 8/2002 | Eichenberger et al. ........ 385/89 |
| 2002/0136510 A1 | 9/2002 | Heinz et al. |
| 2002/0149821 A1 | 10/2002 | Aronson et al. |
| 2002/0159725 A1 * | 10/2002 | Bucklen ................ 385/101 |
| 2002/0160656 A1 | 10/2002 | Nishita |
| 2002/0177362 A1 | 11/2002 | Chang |
| 2003/0016920 A1 | 1/2003 | Sohmura et al. |
| 2003/0021580 A1 | 1/2003 | Matthews |
| 2003/0034963 A1 | 2/2003 | Moon et al. |
| 2003/0208779 A1 | 11/2003 | Green et al. |
| 2003/0223756 A1 | 12/2003 | Tatum et al. |
| 2004/0008996 A1 | 1/2004 | Aronson et al. |
| 2004/0076119 A1 * | 4/2004 | Aronson et al. ............ 370/249 |
| 2004/0141695 A1 | 7/2004 | Miller et al. |
| 2004/0184746 A1 | 9/2004 | Chang et al. |
| 2004/0208600 A1 | 10/2004 | Guenter et al. |
| 2004/0252560 A1 | 12/2004 | Hsieh |
| 2004/0263941 A1 | 12/2004 | Chen et al. |
| 2004/0264879 A1 | 12/2004 | McColloch et al. |
| 2005/0036746 A1 | 2/2005 | Scheibenreif et al. |
| 2005/0053340 A1 | 3/2005 | Toriumi et al. ............ 385/101 |
| 2005/0063440 A1 | 3/2005 | Deppe |
| 2005/0063707 A1 | 3/2005 | Imai |
| 2005/0063711 A1 * | 3/2005 | Rossi et al. ................ 398/198 |
| 2005/0078916 A1 | 4/2005 | Hosking |
| 2005/0105910 A1 | 5/2005 | Light |
| 2005/0105913 A1 | 5/2005 | Ozeki et al. |
| 2005/0105915 A1 | 5/2005 | Light |
| 2005/0180700 A1 | 8/2005 | Farr |
| 2005/0238358 A1 | 10/2005 | Light |
| 2005/0249477 A1 | 11/2005 | Parrish |
| 2005/0286593 A1 | 12/2005 | Guenter |
| 2005/0286893 A1 | 12/2005 | Horiuchi |
| 2006/0008276 A1 | 1/2006 | Sakai et al. |
| 2006/0036788 A1 | 2/2006 | Galang et al. |
| 2006/0045425 A1 | 3/2006 | Kanie et al. |
| 2006/0045437 A1 | 3/2006 | Tatum et al. |
| 2006/0045526 A1 | 3/2006 | Katayama et al. |
| 2006/0049936 A1 | 3/2006 | Collins et al. |
| 2006/0067690 A1 | 3/2006 | Tatum et al. |
| 2006/0077778 A1 | 4/2006 | Tatum et al. |
| 2006/0083518 A1 | 4/2006 | Lee et al. |
| 2006/0088251 A1 | 4/2006 | Wang et al. .................. 385/88 |
| 2006/0093280 A1 | 5/2006 | McColloch et al. |
| 2006/0142744 A1 | 6/2006 | Boutoussov |
| 2007/0058976 A1 | 3/2007 | Tatum et al. |

FOREIGN PATENT DOCUMENTS

| | | |
|---|---|---|
| JP | 08-008818 | 1/1996 |
| JP | 08130508 | 5/1996 |
| JP | 09-162811 | 6/1997 |
| JP | 2000241642 | 9/2000 |
| JP | 2002208896 | 7/2002 |
| JP | 2002-366340 | 12/2002 |
| JP | 2003-163639 | 6/2003 |
| JP | 2003249711 | 9/2003 |
| JP | 2003-332667 | 11/2003 |
| JP | 2004200847 | 7/2004 |
| JP | 2004213949 | 7/2004 |
| JP | 2004241361 | 8/2004 |
| WO | WO03063309 | 7/2003 |
| WO | 2004054139 | 6/2004 |
| WO | WO2004054139 | 6/2004 |

OTHER PUBLICATIONS http://www.fujifilm.com/news/n040908.html; Full-Scale Entry of Optical Transmission System Business Begins as Fujifilm Introduces Optical DVI Link System That Utilizes Lumistar, A Graded Index Plastic Optical Fiber -Realizes World's First 30M-Class High-Speed Optical Linking of Digital Images Using a Plastic Optical Fiber; Sep. 8, 2004, (3 pages).

Optical DVI (Digital Visual Interface)Link System (Picture, 1 page).

http://www.networktechinc.com/dvi-optical-extender.html; DVI Extender Extend a single link digital DVI display up to 4,950 feet (1,500 meters). Also known as: DVI Optical Extension, DVI-D extender, DVI digital to multimode fiber, optical extender, graphic extension modules, fiber optic digital video extender. (web page; 2 pages).

http://www.ramelectronics.net/html/DVI_fiber_cables.html; DVI and HDMI extension, CAT5 and Fiber Optic Perfect Extenders for your Projector, Plasma, LCD screen or HDTV. (web page; 6 pages).

U.S. Appl. No. 11/402,106, filed Apr. 10, 2006; Active Optical Cable With Electrical Connector; Lewis B. Aronson, et al.

U.S. Appl. No. 11/402,186, filed Apr. 10, 2006; Active Optical Cable Electrical Connector; Lewis B. Aronson et al.

U.S. Appl. No. 11/402,241, filed Apr. 10, 2006; Active Optical Cable Electrical Adaptor; Lewis B. Aronson et al.

U.S. Appl. No. 11/402,161, filed Apr. 10, 2006; Electrical-Optical Active Optical Cable; Lewis B. Aronson et al.

U.S. Appl. No. 11/402,802, filed Apr. 10, 2006; Active Optical Cable With Integrated Power; Lewis B. Aronson et al.

U.S. Appl. No. 11/401,803, filed Apr. 10, 2006; Active Optical Cable With Integrated Eye Safety; Lewis B. Aronson.

"Fiber Optic Infrastructure," © 2000 by Extreme Networks, Inc.

"Optical DVI—HDCP Extension Cable," by Opticis, dated Aug. 27, 2003.

Caruso, Jeff; "Bandwidth Boom: Making The Connection, Can Fiber Break Through the Glass Ceiling?" Jul. 13, 1998 [retrieved on Apr. 25, 2005]. (Web page; 3 pages). http://www.internetweek.com/supp/bandwidth/canfiber.htm.

Opticis; "Optical DV1 Extension Module" © 2005 [retrieved on Apr. 25, 2005]. (Web page; 2 pages). http://www.opticis.com/products_2.htm.

Kanellos, Michael; "Intel Gets Optical With Fibre" Mar. 1, 2004 [retrieved on Apr. 26, 2005]. (Web page; 2 pages). http://news.zdnet.co.uk/0,39020330,39147918,00.htm.

Kanellos, Michael; "Intel Connects Chips With Optical Fiber" Feb. 27, 2004 [retrieved on Apr. 26, 2005]. (Web page; 5 pages). http://news.zdnet.com/2100-9574_22-5166883.html.

"Sandia Develops Vertical Cavity Surface Emitting Laser that Promises to Reduce Cost of Fiber Optics Connections," Sandia National Laboratories, Jun. 6, 2000, (Web page; 3 pages). http://www.sandia.gove/media/NewsRet/NR2000/laser.htm.

Digital Visual Interface DVI Revision 1.0, Digital Display Working Group. Apr. 2, 1999.

High-Definition Multimedia Interface Specification Version 1.1, HDMI Licensing, LLC. May 20, 2004.

High-Definition Multimedia Interface Specification Version 1.1, HDMI Licensing, LLC. August 22, 2005.

U.S. Appl. No. 11/468,280, filed Aug. 28, 2006; Optical Networks for Consumer Electronics; Jimmy A. Tatum et al.

U.S. Appl. No. 11/470,623, filed Sep. 6, 2006; Laser Drivers for Closed Path Optical Cables; Jim A. Tatum et al.

Inova Semiconductors, Application Note, GigaStar Digital Display Link, Interfacing Between GigaSTaR DDL and DVI/LVDS, Revision 1.0, 10 pages.

Steve Joiner, Open Fiber Control for Parallel Optics, Communication Semiconductor Solutions Division, Mar. 27, 1997, 13, USA.

U.S. Appl. No. 10/829,609, filed Apr. 22, 2004 entitled "Compact Optical Transceivers."

"IEC 825-1 Eye Safety Classifcation of Some Consumer Electronic products," A.C. Boucouvalas, Bournemouth University, School of Electronics, Talbot campus, Fern Barrow, Pole, Dorset, BH12 5BB, U.K. E-mail: tbournemouth.ac.uk, 1996 The Institution of Electrical Engineers, printed and published by the IEE, Savoy Place, London WC2R OBL, UK, (Web page; 6 pages).

U.S. Appl. No. 11/009,208, Mail Date Oct. 26, 2007, Notice of Allowance.

U.S. Appl. No. 11/009,208, Mail Date Oct. 1, 2007, Office Action.

U.S. Appl. No. 11/009,208, Mail Date Apr. 3, 2007, Final Office Action.

U.S. Appl. No. 11/009,208, Mail Date Jul. 26, 2006, Office Action.

U.S. Appl. No. 11/009,208, Mail Date Feb. 14, 2006, Office Action.

U.S. Appl. No. 11/198,619, Mail Date Dec. 17, 2008, Office Action.

U.S. Appl. No. 11/198,619, Mail Date Apr. 18, 2008, Final Office Action.

U.S. Appl. No. 11/198,619, Mail Date Nov. 16, 2007, Office Action.

U.S. Appl. No. 11/198,619, Mail Date May 4, 2007, Final Office Action.

U.S. Appl. No. 11/198,619, Mail Date Oct. 11, 2006, Office Action.

U.S. Appl. No. 11/468,280, Mail Date Oct. 20, 2008, Office Action.

U.S. Appl. No. 11/468,280, Mail Date Jul. 28, 2008, Office Action.

U.S. Appl. No. 11/468,280, Mail Date Mar. 20, 2008, Final Office Action.

U.S. Appl. No. 11/468,280, Mail Date Sep. 11, 2007, Office Action.

U.S. Appl. No. 11/402,106, Mail Date Oct. 20, 2008, Notice of Allowance.

U.S. Appl. No. 11/402,106, Mail Date Apr. 29, 2008, Office Action.

U.S. Appl. No. 11/402,106, Mail Date Dec. 28, 2007, Final Office Action.

U.S. Appl. No. 11/402,106, Mail Date May 7, 2007, Final Office Action.

U.S. Appl. No. 11/402,106, Mail Date Sep. 21, 2006, Office Action.

U.S. Appl. No. 11/402,186, Mail Date Jul. 3, 2007, Final Office Action.

U.S. Appl. No. 11/402,186, Mail Date Oct. 10, 2006, Office Action.

U.S. Appl. No. 11/198,606, Mail Date Jul. 9, 2008, Final Office Action.

U.S. Appl. No. 11/198,606, Mail Date Dec. 31, 2007, Office Action.

U.S. Appl. No. 11/470,623, Mail Date Sep. 9, 2008, Final Office Action.

U.S. Appl. No. 11/470,623, Mail Date Feb. 19, 2008, Office Action.

U.S. Appl. No. 11/401,803, Mail Date Jun. 30, 2008, Notice of Allowance.

U.S. Appl. No. 11/401,803, Mail Date Aug. 24, 2007, Office Action.

U.S. Appl. No. 11/401,803, Mail Date Jul. 11, 2007, Office Action.

U.S. Appl. No. 11/402,241, Mail Date Mar. 25, 2008, Office Action.

U.S. Appl. No. 11/402,241, Mail Date Apr. 17, 2007, Office Action.

U.S. Appl. No. 11/401,802, Mail Date Mar. 20, 2008, Final Office Action.

U.S. Appl. No. 11/401,802, Mail Date Apr. 17, 2007, Office Action.

U.S. Appl. No. 11/402,161, Mail Date Mar. 14, 2008, Notice of Allowance.

U.S. Appl. No. 11/402,161, Mail Date Sep. 11, 2007, Office Action.

U.S. Appl. No. 11/402,161, Mail Date May 31, 2007, Office Action.

Opticis, M1-1P0 DVI—HDCP Extension Cable, Stretch your Digital Visual Interface Experience, Version 1.03 Aug. 2003, www.opticis.com, 2pages.

* cited by examiner

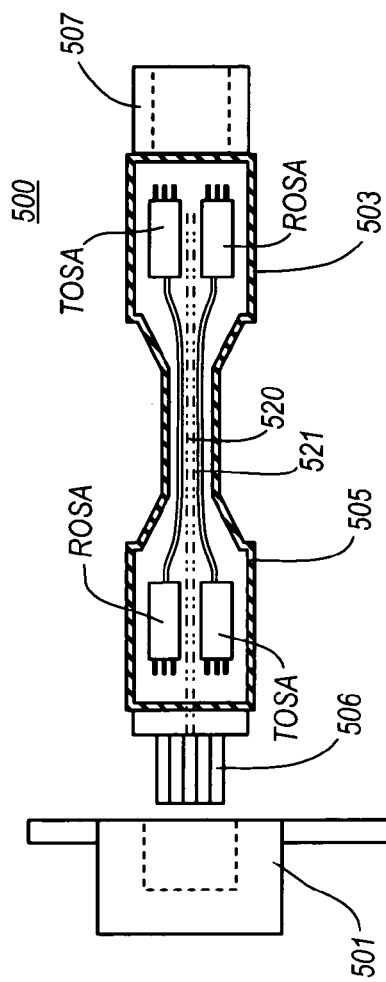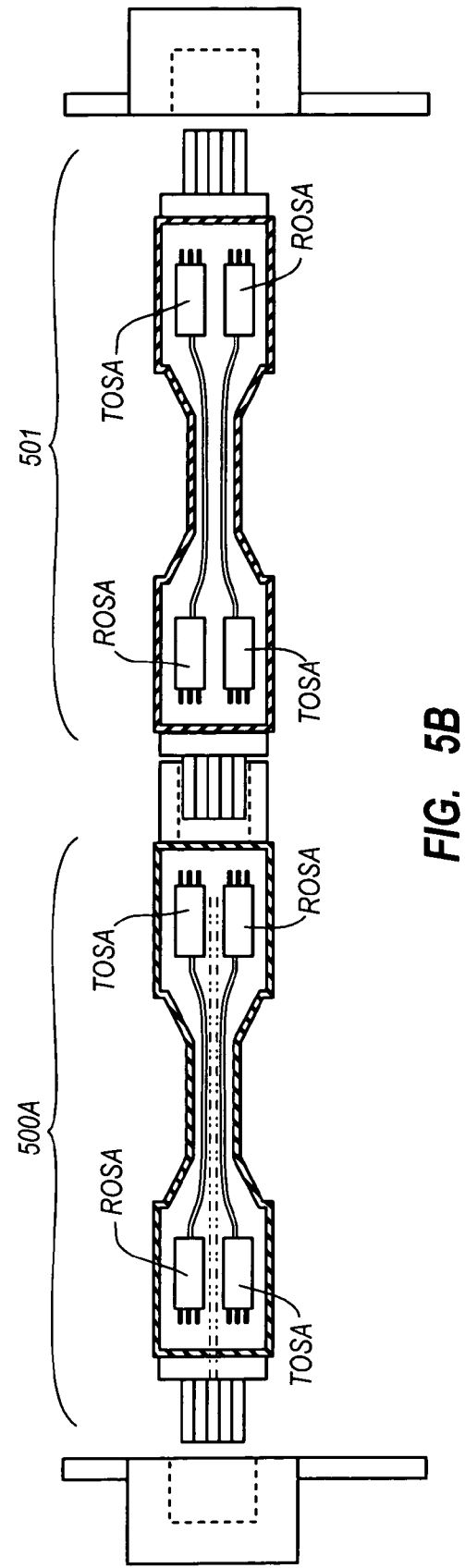
FIG. 5A
FIG. 5B

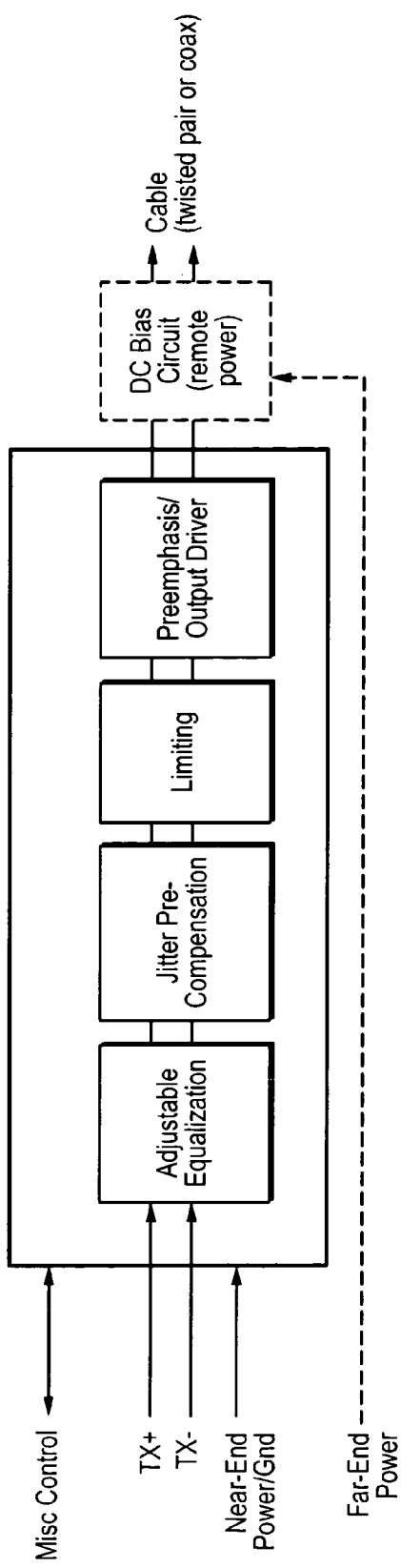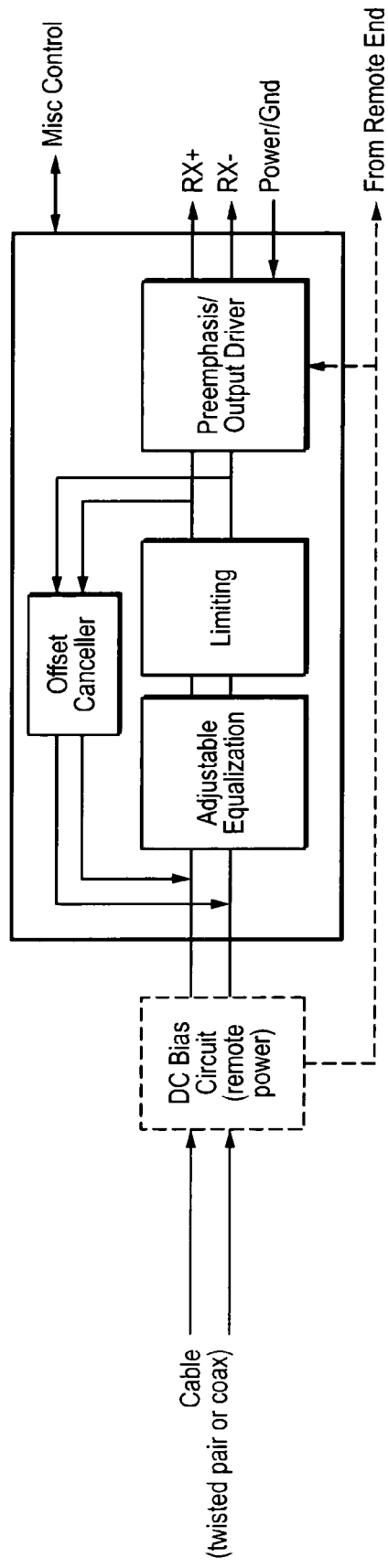
FIG. 12A
FIG. 12B

ACTIVE OPTICAL CABLE WITH INTEGRATED RETIMING

BACKGROUND

Communication technology has transformed our world. As the amount of information communicated over networks has increased, high speed transmission has become ever more critical. High speed communications often rely on the presence of high bandwidth capacity links between network nodes. There are both copper-based solutions and optical solutions used when setting up a high bandwidth capacity link. A link may typically comprise a transmitter that transmits a signal over a medium to a receiver, either in one direction between two network nodes, or bi-directionally. An optical link might include, for example, an optical transmitter, a fiber optic medium, and an optical receiver for each direction of communication. In duplex mode, an optical transceiver serves as both an optical transmitter that serves to transmit optically over one fiber to the other node, while receiving optical signals over another fiber (typically in the same fiber-optic cable).

Presently, communication at more than 1 gigabit per second (also commonly referred to as "1 G") links are quite common. Standards for communicating at 1 G are well established. For instance, the Gigabit Ethernet standard has been available for some time, and specifies standards for communicating using Ethernet technology at the high rate of 1 G. At 1 G, optical links tend to be used more for longer spanning links (e.g., greater than 100 meters), whereas copper solutions tend to be used more for shorter links due in large part to the promulgation of the 1000Base-T standard, which permits 1 G communication over standard Category 5 ("Cat-5") unshielded twisted-pair network cable for links up to 100 m.

More recently, high-capacity links at 10 gigabits per second (often referred to in the industry as "10 G") have been standardized. As bandwidth requirements increase, potential solutions become more difficult to accomplish, especially with copper-based solutions. One copper-based 10 G solution is known as 10GBASE-CX4 (see IEEE Std 802.3ak-2004, "Amendment: Physical Layer and Management Parameters for 10 Gb/s Operation Type 10GBASE-CX4" Mar. 1, 2004), which accomplishes the higher bandwidth, despite the use of copper. 10GBASE-CX4 uses a cable, which includes 4 shielded different pairs carrying a quarter of the bandwidth in each direction, for a total of 8 differential copper pairs. This cable is quite bulky (typically about 0.4" or 10 mm in diameter) and expensive to make and cannot be terminated in the field (as can CAT-5 for example). Furthermore, this copper-based 10 G solution is limited to distances of about 15 m without special efforts. Alternative copper-based 10 G solutions are being developed and standardized but are likely also to require significant power consumption. The primary example is known as 10GBASE-T under development in the IEEE (see IEEE draft standard 802.3an, "Part 3: Carrier Sense Multiple Access with CollisionDetection (CSMA/CD) Access Method and Physical Layer Specifications Amendment: Physical Layer and Management Parameters for 10 Gb/s Operation, Type 10GBASE-T" 2006). This standard uses CAT5 e or CAT6A unshielded twisted pair cable for distances to 55 m and 100 m respectively. However it is expected that because of the extremely complex signal processing required, this standard will require circuitry with very high power dissipation, initially as high as 8-15 Watts (per port and thus twice this per link). A lower power variant which only achieves 30 m on CAT6A cable is still expected to be more than 4 Watts per port. These high power levels represent both a significant increase in operating costs and perhaps more importantly, limitations on the density of ports which can be provided on a front panel. For example, power dissipations of 8-15 W could limit port density to 8 ports or less in the space of a typical 1U rack unit, whereas 1000BASE-T and 1 G optical interfaces such as the SFP transceiver can provide up to 48 ports in the same space. Nevertheless, because of the cost of present day optical solutions at 10 G, there remains interest in this copper solution.

At the present stage, those setting up the high-bandwidth link will often weigh the pros and cons of using a copper-based solution versus an optical solution. Depending on the results of that decision, the systems will be set up with an electrical port if they decided to proceed with a copper-based solution, or an optical port (often more specifically a cage and connector to receiver a standard mechanical form factor optical transceiver such as the SFP) if they decided to proceed with an optical solution.

BRIEF SUMMARY

Although not required, embodiments of the present invention relate to an active cable that is configured to communicate over much of its length using one or more optical fibers, and that includes an integrated electrical connector at at least one end. The active cable includes an integrated retiming mechanism. Thus, multiple links of cable may be used while reducing the chance that the jitter will exceed allowable limits. This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

BRIEF DESCRIPTION OF THE DRAWINGS

The appended drawings are used in order to more particularly describe embodiments of the present invention. Understanding that these drawings depict only typical embodiments of the invention and are not therefore to be considered to be limiting of its scope, the embodiments will be described and explained with additional specificity and detail through the use of the accompanying drawings in which:

FIG. 5A illustrates an electrical-to-electrical male-to-female cable;

FIG. 5B illustrates a three cable link that incorporates several instances of the cable of FIG. 5A;

FIG. 12A illustrates an active copper cable transmitter integrated circuit;

FIG. 12 illustrates an active copper cable receiver integrated circuit;

DETAILED DESCRIPTION OF THE PREFERRED EMBODIMENTS

Embodiments of the present invention relate to the use of a communication cable that is exposed at least at one end using an electrical connection, while communicating over much of its length using optical fiber. Thus, those designing or selecting networking equipment or administrating network nodes need not choose a copper-based solution or an optical solution in communicating over a network. Instead, the network node need only have an electrical port of some type to thereby support either copper-based communication or optical communication. In addition to network applications, such a cable can support point to point high speed serial connections such as the transmission of serialized video data from source to a display. The communication over the optical fiber may be high speed and suitable for 10 G applications and higher. As will described below, cable designs which are purely electrical but mechanically and electrically interoperate with the optical cables described herein may be included as part of a complete system to provide the most effective solutions over the widest range of applications.

Figure 1:
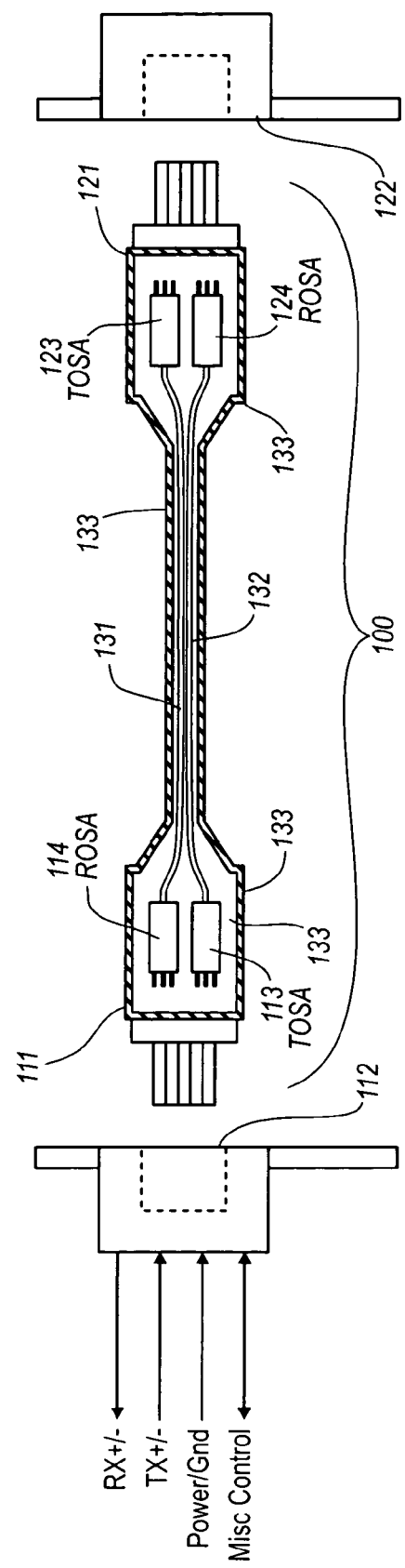
FIG. 1 illustrates a fully duplex electrical-to-electrical cable.

FIG. 1 illustrates an integrated cable 100 that has electrical connections 111 and 121 at both ends. Each electrical connection is sized and configured to connect to a corresponding electrical port at each network node. For example, electrical connector 111 is configured to connect to electrical port 112 at one network node, while the electrical connector 121 is configured to connect to the electrical port 122 at the other network node. From the external connection viewpoint, it is as though the cable is entirely an electrical cable.

However, upon closer examination of the cable 100 of FIG. 1, communication over at least part of the cable length is actually accomplished via optical fibers. Each end of the cable 100 has optics that support duplex-mode optical communications. Specifically, the optics at each end of the cable 100 include a transmit optical sub-assembly (TOSA) for transmission of an optical signal over one optical fiber and a receive optical sub-assembly (ROSA) for receipt of an optical signal from another optical fiber. Integrated circuits to drive the transmitting optics and to receive the detected signal are included. These ICs may be outside the TOSA or ROSA or may be integrated directly in their design. Though the cable 100 is illustrated as supporting duplex-mode in which optical communication occurs in either direction, the cable may also perform communication in one direction consisting of a single transmitter at one end and a single receiver at the other.

Referring in further detail to FIG. 1, the cable 100 includes two optical fibers 131 and 132 integrated within the cable 100. When an electrical signal is applied to the appropriate connections of the electrical connector 121 (e.g., through the electrical port 122), those electrical signals are converted by a laser driver and TOSA 123 (or more specifically by an electro-optical transducer within the TOSA 123) to a corresponding optical signal. As noted, the laser driver may be included within the TOSA. The optical signal is transmitted over optical fiber 131 to ROSA 114. The ROSA 114 (or more specifically, an opto-electronic transducer within the ROSA 114) converts the optical signal received from the optical fiber 131 into a corresponding electrical signal. Typically the optical transducer would consist of a PIN detector and a preamplifier Integrated Circuit (IC), usually with a transimpedance amplifier front-end design. A limiting amplifier may also be integrated with the preamplifier or provided separately. The electrical signal is applied on the appropriate connections of the electrical connector 111, whereupon it is provided to the electrical port 112. While the cable 100 may be of any length, in one embodiment, the length is from 1 to 100 meters. The cable may support high speed communication range between 1 to 10 gigabits per second and beyond.

If the principles of the present invention are to be applied to bi-directional communication, when an electrical signal is applied to the appropriate connections of the electrical connector 111 (e.g., through the electrical port 112), those electrical signals are converted by a laser driver and TOSA 113 (or more specifically by an electro-optical transducer within the TOSA 113) to a corresponding optical signal. Once again, the laser driver may (but need not) be integrated within the TOSA. The optical signal is transmitted over optical fiber 132 to ROSA 124. The ROSA 124 (or more specifically, an opto-electronic transducer within the ROSA 124) converts the optical signal received from the optical fiber 132 into a corresponding electrical signal. The electrical signal is applied on the appropriate connections of the electrical connector 121, whereupon it is provided to the electrical port 122. The cable 100 may additionally include a protective coating 133 which protects the optical fibers, the optics and portions of the electrical connectors. Finally, though not shown in the figure, the fiber optic cable would typically include some form of strength member such as Kevlar yarn.

In principle, any type of optical fiber (single mode or multimode) could be used with the appropriate TOSA and ROSA designs. In some embodiments, however, the use of multimode fiber for links of 100 m and less with shortwave (~850 nm) VCSEL sources may be desirable. There are several important types of multimode fiber worth considering and distinguishing which is preferred in different situations. Of course, as the relative costs and alternatives associated with each of the multimode fiber solutions changes over time, the considerations referred to below may also change.

Presently, a quite cost effective choice for connections at least to 30 meters would be a type of multimode fiber generically referred to as OM2 which has a core and cladding diameter of about 50 and 125 microns respectively and has a minimum overfilled bandwidth (OFL) of about 500 MHz·km. While links can be constructed using this fiber for distances beyond 30 meters, the fiber would start to add a significant amount of jitter to the link (discussed generally below) which may be an undesirable tradeoff.

For links longer than about 30 meters, fiber with a tighter tolerance on the core design but with identical mechanical dimensions may be desirable. In particularly, a class of fiber generally known as OM3 which has a minimum OFL of 2000 MHz·km is available, and would provide very small signal impairment to a distance of 100 meters or more (and it has conventionally been used for links up to perhaps 300 meters).

Those skilled in the arts will recognize that the distance at which to use a certain type of fiber will be determined by many factors and may result in a tradeoff point significantly different than 30 meters.

An important new type of multimode fiber made with organic polymer (plastic) material may prove extremely cost effective for these applications because of the simplicity of the termination of a fiber itself. Plastic fibers have been available for many years but have generally required very short wavelength sources (about 650 nm) and because of their simple step index core design have bandwidths orders of magnitude too low for 1 G to 10 G applications. Recently however, designs have been introduced which substitute fluorine for hydrogen in the polymer structure reducing attenuation at longer wavelength such as 850 nm. More importantly, graded index core designs have been realized which provide OFL bandwidths of 300 MHz·km or more which is sufficient for links of 20 meters or longer.

Of course, the opto-electronic conversion process and the electro-optic conversion process require power in order to convert between optical and electrical energy. Thus, the electrical connectors supply power from the host at at least one end of the cable 133 to power the opto-electronic conversion. The power connection may be, for example, a 3.3 volt power connection. In FIG. 1, for example, the electrical port 112 is illustrated as supplying Power/Gnd connections for conveying electrical power from the host to electrical connector 111.

Thus, conveyance of information is accomplished largely by means of an optical signal, while providing electrical connections on both ends of the cable. The purchaser of the cable need not even be aware that the cable is an optical cable. In fact, a copper cable could be provided for particularly short links (perhaps 1 to 5 meters) which emulates the cable 100 of FIG. 1, embodiments of which are described further below with respect to FIGS. 8A through 13B.

While a single cable assembly linking two pieces of equipment is probably the simplest and lowest cost configuration in terms of hardware and perhaps preferred for shorter links (for example, less than 10 meters), it may prove inconvenient to install for longer connections (for example, more than 30 meters). For longer distances, connections of multiple cables may be more convenient. In conventional optical links, for example, it is common for a longer length of cable to be terminated at each end at a patch panel consisting of one or more cable plug end connectors. A short connection is made from the optical ports on network equipment at each end of the link to the corresponding patch panel using a relatively short (from 1 to 5 meter) patch cable. In other cases, even more complicated connections are used involving as many as 4 to 6 connections.

While some embodiments of potential applications of the present invention could be served by a single cable, variations which would allow the connection of at least three cables would be of great utility. There are several possible methods by which the present cable may be interconnected to other such cables or other variants to be described, all of which being encompassed within the principles of the present invention. The various embodiments have different relative advantages.

Figure 2A:
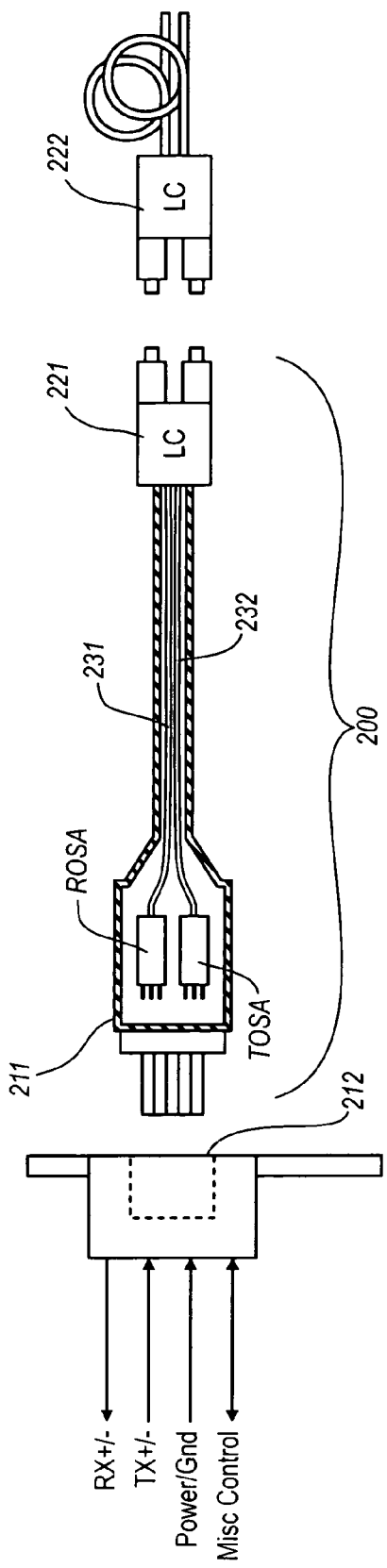
FIG. 2A illustrates a fully duplex electrical-to-optical cable.

FIG. 2A illustrates an integrated cable 200 in accordance with another embodiment of the invention in which the cable 200 may be used as one link in a multiple link connection. The integrated cable 200 of FIG. 2A is similar to the integrated cable 100 of FIG. 1, except that the integrated cable 200 has an electrical connector 211 on only one end of the cable for connection with the electrical port 212, and an optical connector 221 on the other end of the cable. The optical connector 221 is configured to permit the cable to receive optical signals from other optical cables through optical fiber 231 using connectors 221 and 222, and transmit optical signals from optical fiber 232 through the other optical cable also using connectors 221 and 222.

In the illustrated embodiment of FIG. 2A, the optical connector 221 is illustrated as a standard LC optical connector (see ANSI/TIA/EIA 604-10. "FOCIS-10 Fiber Optic Connector Intermateability Standard" 10/99 for more information concerning the standard LC optical connector). However, any optical connection may suffice including, but not limited to, SC optical connectors (see IEC61754-4 "Fiber optic connector interface Part 4: Type SC connector family" Ed 1.2, 2002-2003 for more information concern the standard SC optical connector) as well as other optical connections, whether now existing or to be developed in the future. While the cable 200 may be of any length, in one embodiment, the length is from 1 to 5 meters.

Figure 2B:
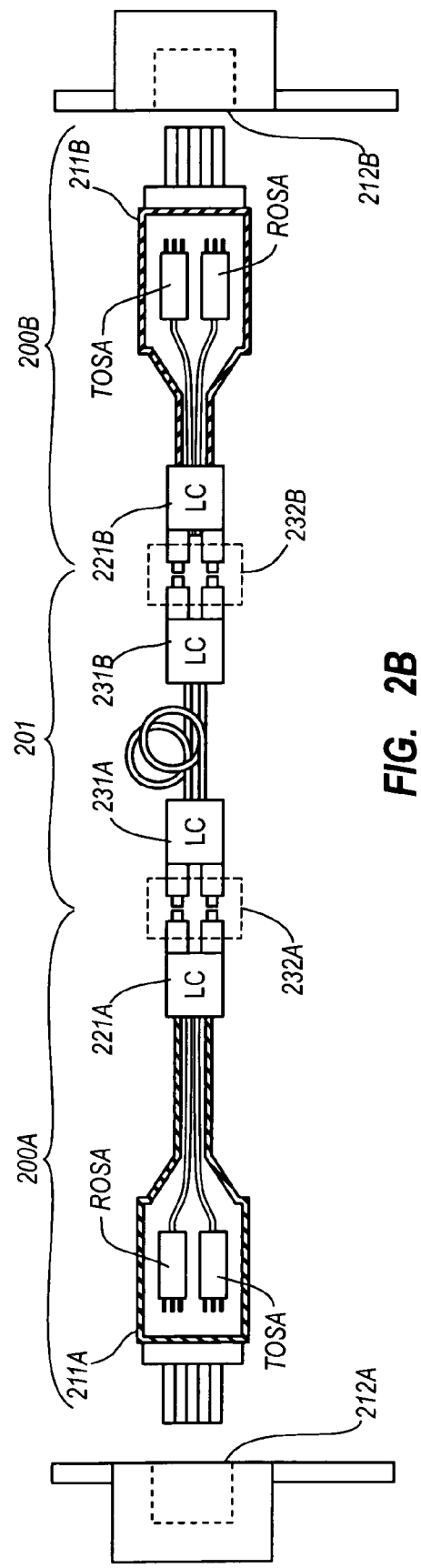
FIG. 2B illustrates a three cable link in which there are electrical-to-optical cables on each end of the sequence, and a fully optical cable disposed therebetween.

The cable illustrated in FIG. 2A may be used in a 3 cable configuration as shown in FIG. 2B where an electrical to optical cable 200A is connected to an optical cable 201 and then to a second optical to electrical cable 200B. The electrical to optical cables and optical to electrical cables may be referred to herein as "E-O" cables. In one embodiment, the E-O cables 200A and 200B are each instances of the cable 200 illustrated and described with respect to FIG. 2A. The optical cable 201 may, but need not, be a standard optical cable.

Thus, electrical signals received from electrical port 212B of the right host in FIG. 2B may be received by the electrical connector 211B of the E-O cable 200B, converted into an optical signal using the TOSA and associated laser driver of the E-O. cable 200B, pass through the E-O optical interface 232B defined by the connection between optical connectors 221B and 231B, pass through the optical cable 201, pass through the optical interface 232A defined by the connection between optical connectors 231A and 221A, through the E-O cable 200A as an optical signal, to finally be received by the ROSA of the E-O cable 200A, whereupon the corresponding electrical signal is received by the electrical port 212A of the left host through the electrical connection 211A.

Conversely, electrical signals received from electrical port 212A of the left host in FIG. 21B may be received by the electrical connector 211A of the E-O cable 200A, converted into an optical signal using the TOSA and associated laser driver of the E-O cable 200A, pass through the E-O optical interface 232A defined by the connection between optical interface 221A and 231A, pass through the optical cable 201, pass through the optical interface 232B defined by the connection between optical connectors 231B and 221B, through the E-O cable 200B as an optical signal, to finally be received by the ROSA of the E-O cable 200B, whereupon the corresponding electrical signal is received by the electrical port 212B of the right host through the electrical connection 211B. In alternative embodiments, the multi-cable link illustrated in FIG. 2B may be extended to consist of multiple lengths of standard optical cable to extend the link to beyond 3 cables.

The E-O cable 200 could have specifications on the optical input and output such as the minimum and maximum transmitted modulated power and the minimum and maximum acceptable receive power. These could either be custom specifications to enable a particular range of links with given fiber types. Alternatively, the optical interface of this cable could comply with one or more existing or future optical standards for multimode or single mode fiber connections.

Figure 2C:
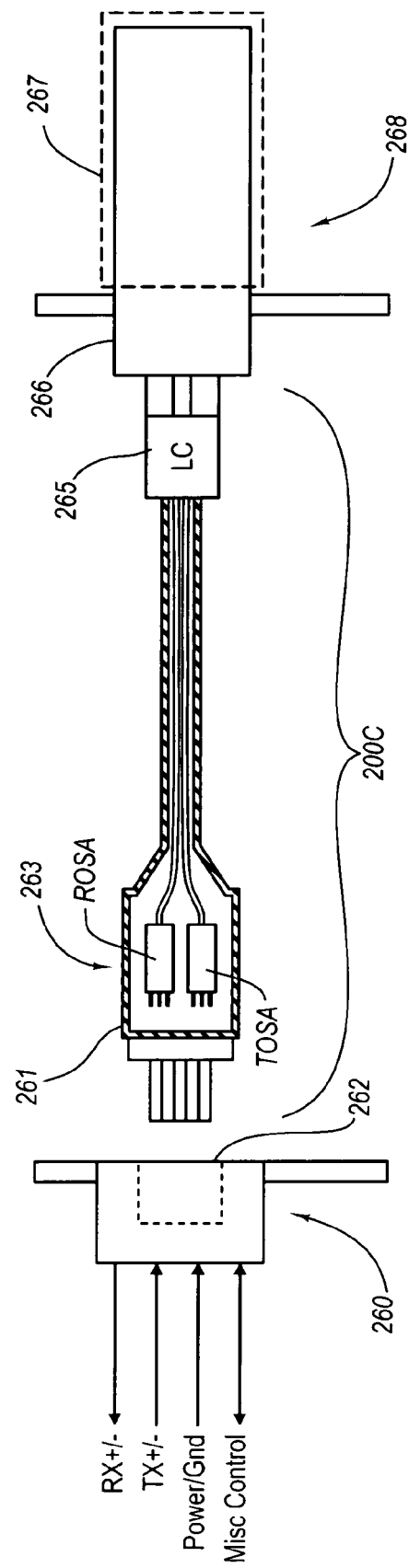
FIG. 2C illustrates an electrical-to-optical cable in which the optical end is coupled to an external optical transceiver.

One example would be the IEEE 10 G BASE-SR standard which allows transmission of up to 300 meters on some grades of multimode optical fiber. This also allows a link as shown in FIG. 2C where one end 263 of the E-O cable 200C is connected to a first piece of network equipment 260 by connecting electrical connection 261 of the cable 200C to an electrical port 262. The E-O cable 200C may be, for example, one instance of the E-O cable 200 of FIG. 2A. The other end 265 of the E-O cable 200C may be configured as an optical connector that is connected to an optical transceiver 266, which has an electrical interface 267 with a second piece of network equipment 268. Thus, in one embodiment, the E-O cable 200C may interoperate with existing optical transceivers such as, for example, the SFP (see Small Form-factor Pluggable (SFP) Transceiver Multi-source Agreement (MSA), Sep. 14, 2000. Also, IF-8074i Specification for SFP (Small Formfactor Pluggable) Transceiver Rev 1.0 May 12, 2001), XFP (see http://www.xfpmsa.org/XFP_SFF_INF_8077i_Rev4_0.pdf), XENPAK (see http://www.xenpak.org/MSA/XENPAK_MSA_R3.0.pdf), X2 (see http://www.x2msa.org/X2_MSA_Rev2.0b.pdf) or XPAK transceivers, as long as the cable 200C followed a consistent set of optical specifications suitable for the transceiver type. The configuration shown in FIG. 2C could also include one or more lengths of optical fiber with standard connectors, with the number determined by the optical link budget to which the E-O cable and optical transceiver comply.

Referring for a moment back to FIG. 1, although the cable 100 communicates over much of its length using optical signals, the cable 100 is connected externally using electrical connectors at both end. Thus, the electrical to electrical (E-E) cable 100 illustrated in FIG. 1 does not have to meet any external optical specification. This is a great advantage to achieving low cost. These inventive principles make it possible to retain this advantage in multiple cable links in a number of possible ways.

Figure 3A:
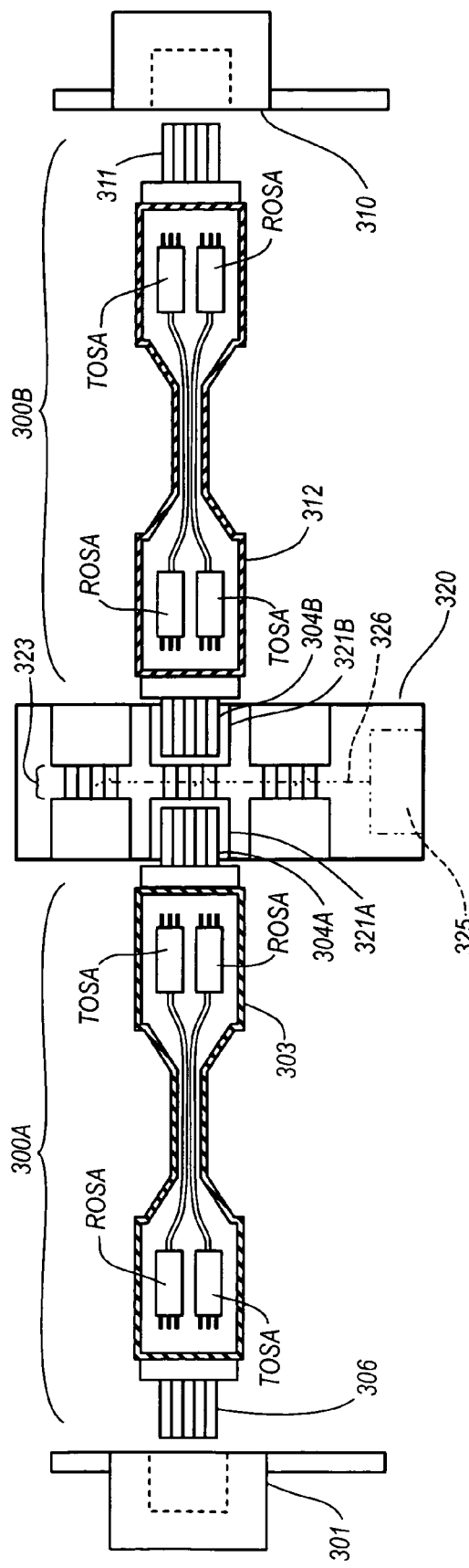
FIG. 3A illustrates two electrical-to-electrical cables coupled to a cable plug end adaptor.

In one embodiment, the cable 100 is used in a three link system of E-E cables by connecting the cables 300A and 300B passively with a cable plug end connection 320 as shown in FIG. 3A, or passively with any other male to male adaptor. The cables 300A and 300B may each be instances of the cable 100 of FIG. 1. For instance, the cable might have a male gender connector (portion 306 of cable 300A, and portion 311 of cable 300B) with the corresponding host receptacles 301 and 310 each being a female connector. In this case, a cable plug end connector 320 would be comprised of two female receptacles 321A and 321B with the receiver connections of one cable (e.g., cable 300A) connected to the transmitter connections of a second cable (e.g., cable 300B), and vice versa. The female receptacle 321A receives the mail connector 304A of the cable 300A, whereas the female receptacle 321B receives the mail connector 304B of the cable 300B. Additionally, low speed control or indicator lines 323 may be used to supply power and low speed control data to the appropriate connection.

One consideration about the above described connection is that it requires that power be available to the optics in the connected ends of the E-E cable. In one embodiment of the E-E cable, there is no copper or other electrical conductor and thus no power connection between the cable ends, with the power for each end being supplied by the host system at each end. In one embodiment, power is delivered to the cable ends in one or more of the following two ways.

Figure 3B:
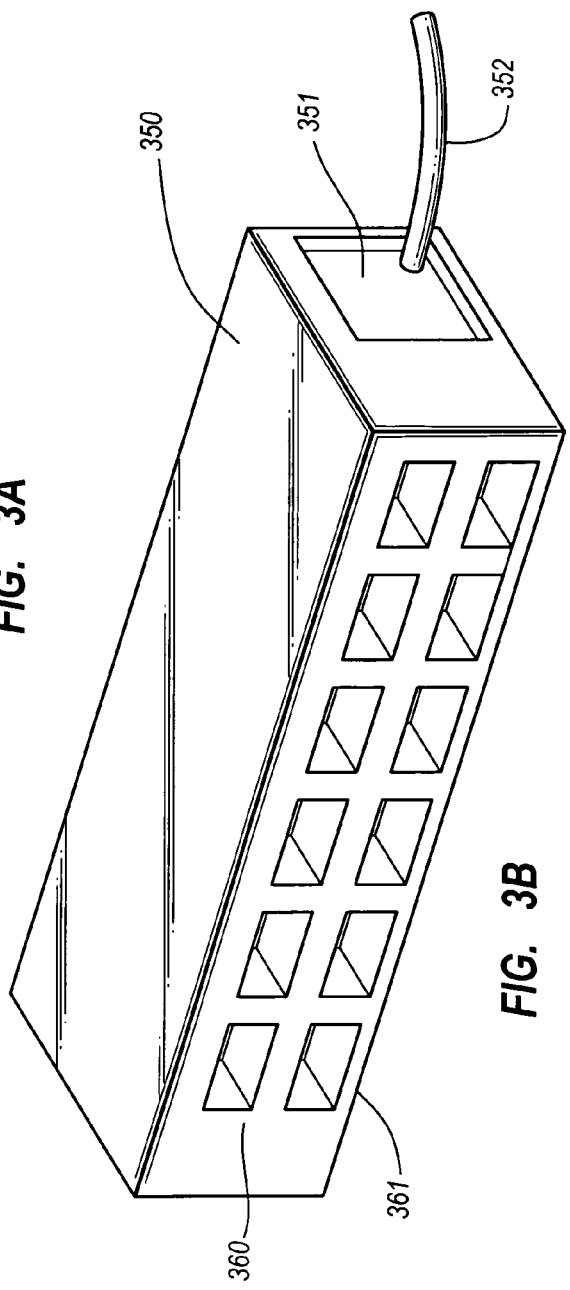
FIG. 3B illustrates more of the mechanical aspects of the cable plug end adaptor of FIG. 3A.

FIGS. 3A and 3B illustrated a cable plug end adapter for connecting two E-E cables of the type illustrated in FIG. 1. The power for the two connector ends, 303 and 312 is provided separately to the cable plug end adapter. As one example, shown in FIG. 3A, a chassis 325 may be provided with a single power connection and power supply 326 which in turns supplies power to one or cable plug end adapters. FIG. 3B shows another example of such a powered set of receptacle to receptacle adapters 350 where the inputs (e.g., input 360) and outputs (e.g., 361) (note that the inputs and outputs are reversible) are arranged on the same side of the chassis. The adapter 350 itself receives power via power line 352 being fed into the adaptor 350 at portion 351.

Figure 4:
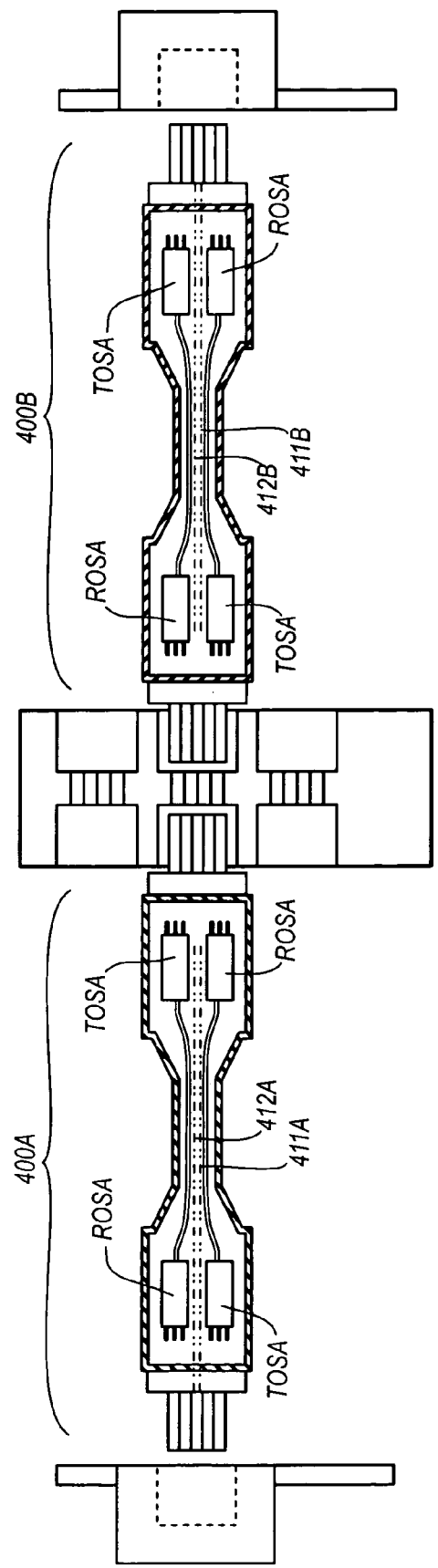
FIG. 4 illustrates two electrical-to-electrical cables with internal power connections coupled to a cable plug end adaptor.

A second method for providing power is illustrated in FIG. 4, which is similar to the structure described with respect to FIG. 3A. However, in this case, E-E cables 400A and 400B are provided. Either or both of the cables 400A and 400B may be the same as that described with respect to FIG. 1, except that at least a pair of electrical conductors (411A and 412A in the case of cable 400A, or 411B and 412B in the case of cable 400B) is provided in the cable along with the optical fibers. These conductors 411 and 412 may either directly connected to the power connections on either end or in order to provide isolation between the two host ends in the normal connections. Pins may be provided separately for the near-end and far-end power connections. In one example, the conductor 411 may be a ground conductor, whereas the conductor 412 may be a power conductor.

An alternative form of the E-E cable could be used to concatenate two or more E-E cables without the need for a separate adapter/connector. This alternative E-E cable 500 is illustrated in FIG. 5A, and the corresponding 2 cable configuration shown in FIG. 5B. The E-E cable 500 shown in FIG. 5A has a male plug connector 506 on one end 505 (i.e., the leftward illustrated end), which would be connected to. the female receptacle 501 on the leftward illustrated host system, and contains transmit and receive optics in the form of a TOSA and a ROSA. The other end 503 (i.e., the rightward illustrated end) of the cable would also contain transmit and receive optics coupled to the optical fiber, also in the form of a TOSA and a ROSA. This right end 503, however, would be configured with the receptacle female gender connector 507 which would function like a host connector, so that further cables may be attached to the cable 500 in a similar manner as those cables would be attached to a host connector. In one embodiment, the cable 500 might be a relative short "patch-cord" lengths of approximately one to five meters. The electrical conductors 520 and 521 are provided in order to provide power to the remote receptacle end 503 (the rightward end) from the host system (illustrated on the left). Referring to FIG. 5B, an instance 500A of the cable 500 of FIG. 5 may be combined with another cable 501 (which is similar to the cable 100 of FIG. 1) to form a series of two cables. Furthermore, a series of three or more cables may be accomplished by connecting multiple instances of the cable of FIG. 5A, with the cable of FIG. 1. For instance, if three cables were to be used, two instances of the cable of FIG. 5A may be combined with one instance of the cable of FIG. 1. In that case, the center cable may be of a relatively long run of, for example, from ten to one hundred meters.

It may prove advantageous to provide separate power supplies for the near end (host side) and far end of a cable which incorporates electrical power conductors for a number of reasons. One reason is the desire to provide a degree of isolation between the interconnect systems. The second reason is to limit the supply requirements of the near end connection used in the majority of connections.

Finally, and probably most important is the desire to overcome some degree of voltage drop along the electrical conductors particularly is light weight, thinner conductors (higher gauge) are used. The use of a higher far end supply voltage may take one of two forms. The first is the use of a slightly higher supply voltage to overcome the conductor voltage drop. As a particular, the active devices in each end of the cable might require a supply voltage of +3.3V±5% (3.145 to 3.465V). In this case, requiring a 3.6V±5% (3.42 to 3.78V) on the far end supply connection would easily overcome the voltage drop expected in patchcords of 5 m or less with typical copper wire gauges. The second case is where there is a need to overcome losses in longer cable runs or to supply a larger amount of power to equipment at the cable end (for example adapters with retimers or even remote disk drives). In this case, it may make sense to use a much higher voltage (say about 40 Volts) where the resistive current loss would be much less. When such high voltages are used, the power must be converted down to lower voltages at the far end through the use of a switching power supply for example.

In any of the above described systems, it might be advantageous to specify the characteristics of various elements in the system in terms of the amount of signal timing jitter they add in order to limit the total jitter of the link to a value which can be handled by the circuit element which ultimately recovers the clock and retimes the signal. Jitter refers to the error in the time position of the digital data transitions and can have numerous sources some of which can be characterized as random and others which result in deterministic, usually data dependent errors in timing.

The above-described methods and mechanisms of linking cables will involve more interfaces (including the connectors, the laser driver and receiver ICs and the lasers and fibers themselves) that can add jitter to the transmitted data signal as compared to a single cable. Thus, meeting a reasonable jitter budget will generally be significantly more difficult in a multi-cable system as described than in a single cable (which could even be tested for its total jitter contribution in the factory).

It is possible to overcome potential jitter limitations by incorporating retiming circuits into the link. For example, a clock and data recovery circuit will eliminate jitter beyond a given frequency effectively resetting the jitter budget in this type of system. Although notRetiming circuits could be incorporated in the cable plug end adapters (or other adaptor for each direction of each duplex link described above and illustrated in FIGS. 3A, and 4, where the power for the optics and the retiming circuit would be supplied locally or from the patchcord-cable respectively. An example of such a system is shown in FIGS. 6A and 6B, in which one or more adapters are incorporated in a single chassis, and using a single Integrated Circuit (IC) that incorporates more than one channel of retiming circuits.

Figure 6A:
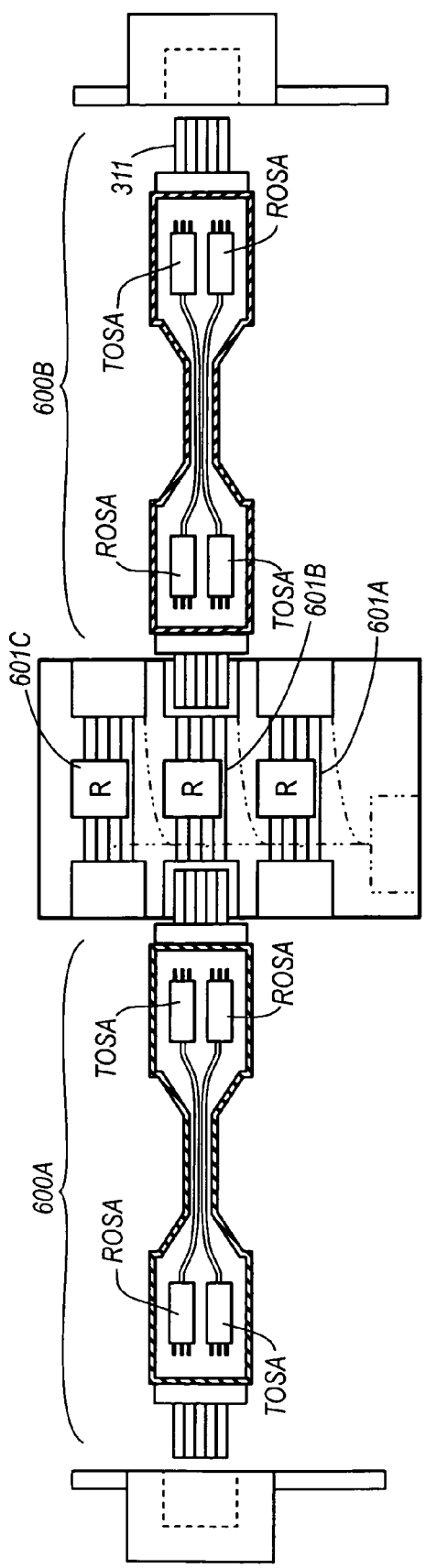
FIG. 6A illustrates the configuration of FIG. 3A, except with retiming incorporated.

Specifically, FIG. 6A illustrates a configuration that is similar to the configuration of FIG. 3A, except that there is a retiming circuit 601A, 601B or 601C within the cable plug end adaptor and interposed within the corresponding electrical channel within the cable plug end adaptor. For instance, retiming circuit 601B is interposed between active cables 600A and 600B to provide for appropriate jitter reduction through retiming. Actually, there are two retiming circuits represented by the retiming circuit 601B, one for each direction of communication. The same can be said for retiming circuits 601A and 601B. Here, power is supplied by the cable plug end connection itself. Mechanisms for retiming are known in the art and thus will not be described in detailed herein.

Figure 6B:
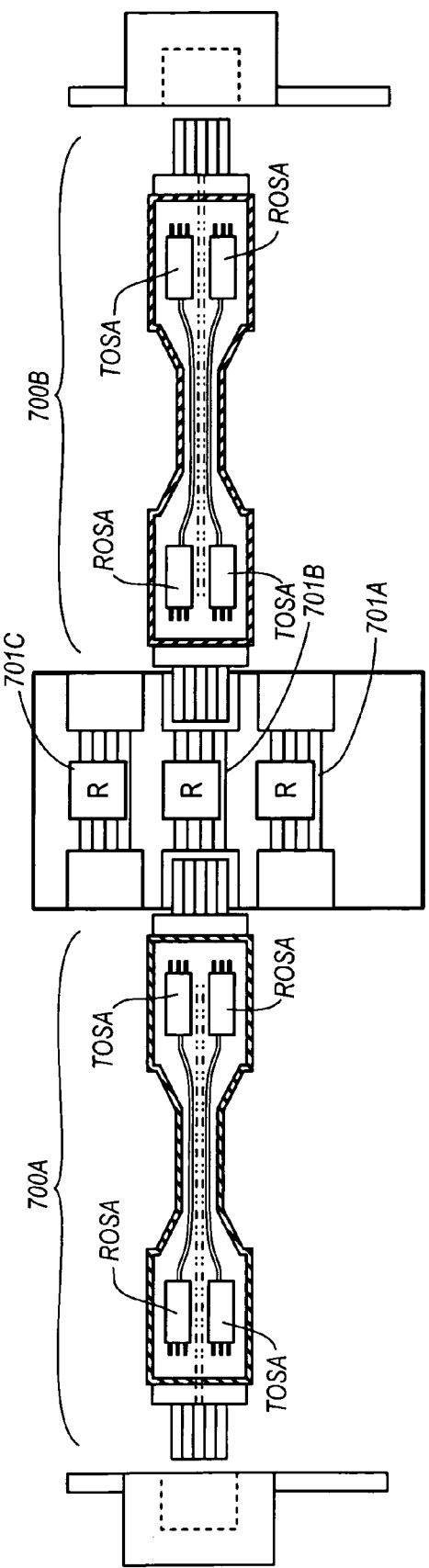
FIG. 6B illustrates the configuration of FIG. 4, except with retiming incorporated.

FIG. 6B illustrates a configuration that is similar to the configuration of FIG. 6A, except that now power conductors are provided in one or both of the active cables 700A and 700B to provide power to the cable plug end connector. Power from one or both of these connectors could be used to power the retiming circuits 701A, 701B and 701C (once again, six retiming circuits total), which operate to retime the electrical signals in the corresponding channel. For instance, retiming circuit 701B is interposed between active cables 700A and 700B to provide for appropriate jitter reduction through retiming.

Figure 7A:
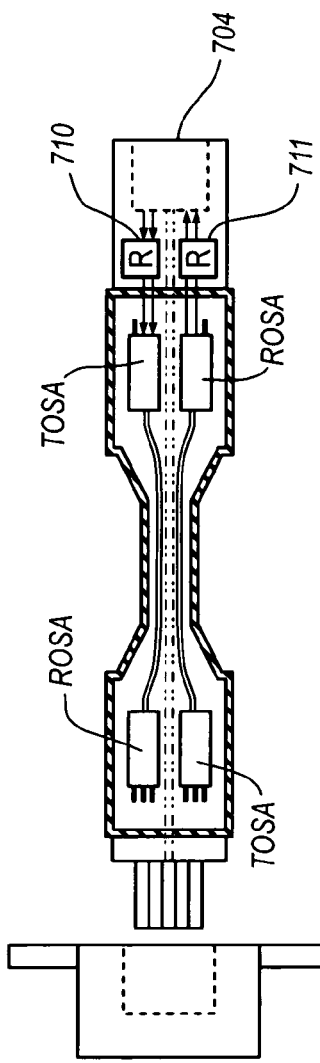
FIG. 7A illustrates the configuration of FIG. 5A, except with retiming incorporated.
Figure 7B:
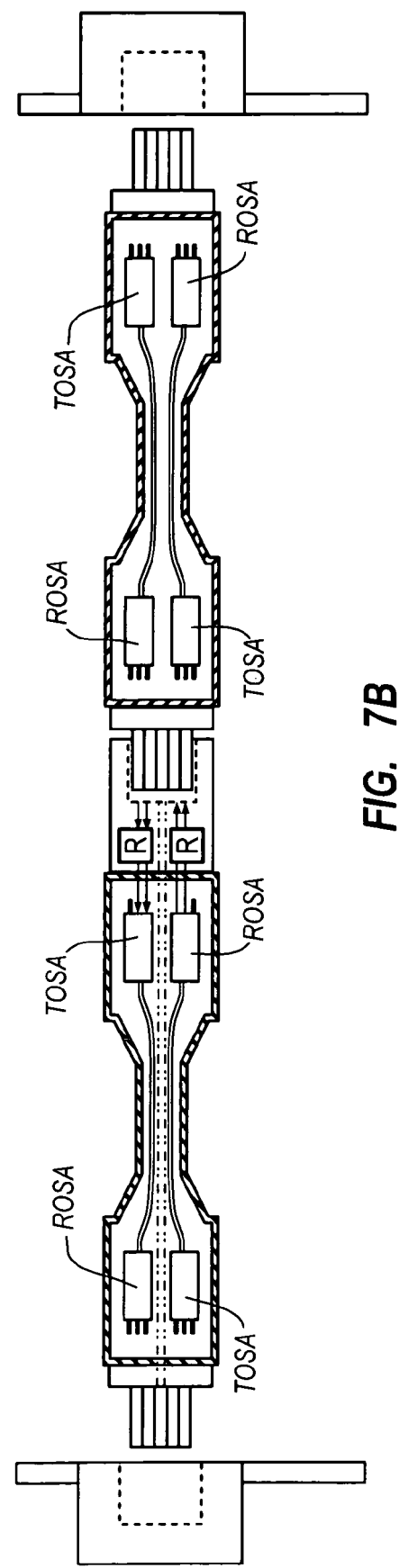
FIG. 7B illustrates the configuration of FIG. 5B, except with retiming incorporated.

Similarly, a retiming circuit could be added to the plug-receptacle type patchcord described in FIG. 5A. This embodiment is illustrated in FIG. 7A, and the associated 2 cable connection of FIG. 5B using this arrangement is shown in FIG. 7B. For instance, referring to FIG. 7A, electrical signals received from the female electrical connector 704 are retimed by retiming circuit 710, whereas electrical signals to be transmitted onto the female electrical connector 704 are retimed by retiming circuit 711.

As described in the some of the implementations of the copper based solution, the cable may also include a mechanism for supporting adaptive equalization of an input high speed electrical signal to reduce total link jitter, a mechanism for providing host selectable equalization of an input high speed electrical signal to reduce total link jitter, a mechanism that provides pre-emphasis of an output high speed electrical signal to reduce total link jitter, a mechanism for providing host selectable pre-emphasis of an output high speed electrical signal to reduce total link jitter. Different host systems may require different degrees of equalization and/or preemphasis because of the particular length or other nature of the electrical interconnect between the cable receptacle and the next IC elements. The integrated cable may support predefined. limits of added deterministic and total jitter of a high speed signal, where such limits may be chosen to allow concatenation of up to 3 cables.

Another means of controlling jitter is non-linear jitter compensation which detects and adjusts edges of particular transitions (see United States Patent Publication No. 20050175355). This method is particularly well suited for compensating for known fixed deterministic jitter sources such as those arising from a particular length of host PCB trace.

It should be noted that while most of the jitter reduction techniques described address the jitter introduced by channel limitations on the host system or on a copper based cable, they may also be usefully applied to compensate for non-idealities of the optical transmitter or receiver (such as those do the non-linear characteristics of the laser source). They may also be used to compensate for the channel characteristics of the fiber itself. Depending on the type of fiber used and the length employed relative to it's total frequency bandwidth, the compensation may be for a simple frequency rolloff or for the more complex multiple peaked impulse responses seen in typical multimode fiber due to differential mode delay.

Cables in accordance with the principles of the present invention may also include additional functionality. For instance, the cable may include a mechanism for confirming whether or not a full duplex connection is present (e.g., by transmitting and receiving a relatively lower optical power level within Class 1 eye safety limits over either or both of the first optical fiber and the second optical fiber), a mechanism to reduce or shut-off optical power whenever a full duplex connection is not confirmed, and/or a mechanism to keep the optical power reduced or off until the presences of a full duplex connection is verified.

The electrical connector may include connections for a loss of signal (LOS) indication, a fault indication, a link disable control signal, presence indication of the integrated cable to a host system that is associated with the first or even second electrical port, an interrupt signal, a reference clock input, low speed serial data interfaces and/or any other connections for control of the cable.

The low speed serial data interface may be configured for use in control of the first electro-optical transducer, may be part of a system for the transmission of out of band data, may be configured to read or write data to nonvolatile memory in the optics portion of the cable, and/or may be used for one or more functions selected from the following list: serial identifier codes, customer security codes. Customer security codes could be provided to specifically allow only host qualified implementations of the cable and to detect outright counterfeit parts. Diagnostic information, which would be dynamically updated in volatile memory could be provided over the same serial interface. The serial interface may also be used for factory setup of the device to load non-volatile data to an internal EEPROM, FLASH memory or set of fusible links in the laser driver and/or receiver IC. The serial interface may be any serial interface, whether not existing (such as SPI interface or I2C interface) or whether to be developed in the future.

The cable may also include its own eye safety measures including a mechanism to disable one or more optical transmitter within the integrated cable if the integrated cable is physically severed such as, for example, when the nominal transmitted power may be greater than the IEC class 1 eye safety limit, a mechanism to transmit optical power at eye safe levels if the integrated cable is physically severed, and/or a mechanism to assert a fault signal if the integrated cable is severed. Furthermore, the eye safety circuit could be used to reassert the link if the shutoff were caused by a reversible cause such as the shutoff of power to the remote end.

One particular mechanism, which might be integrated in the cable, is the Open Fiber Control (OFC) system developed as part of the Fibre Channel standard (see ANSI X3.230-1994 section 6.2.3 pp 42-48). In fact, a considerably simplified version of the OFC protocol could be used since OFC must deal with two independent transceivers and must function properly if a non-OFC transceiver is connected to an OFC device. In the case of an active cable where both ends are controlled, this situation cannot occur. In any case, the eye safety features in the cable may be designed to function in the event of any reasonable single fault condition.

The cable may include at least one electrical conductor spanning the length of the integrated cable. As previously mentioned, this electrical conductor may be used to transmit electrical power from one end of the cable to the other end of the cable. However, alternatively or in addition, there may be electrical conductors for transmitting low speed serial data from one end of the integrated cable to the other end of the integrated cable. Furthermore, the cables included for transmitting electrical power may be simultaneously used for transmission of low speed serial data.

Figure 8A:
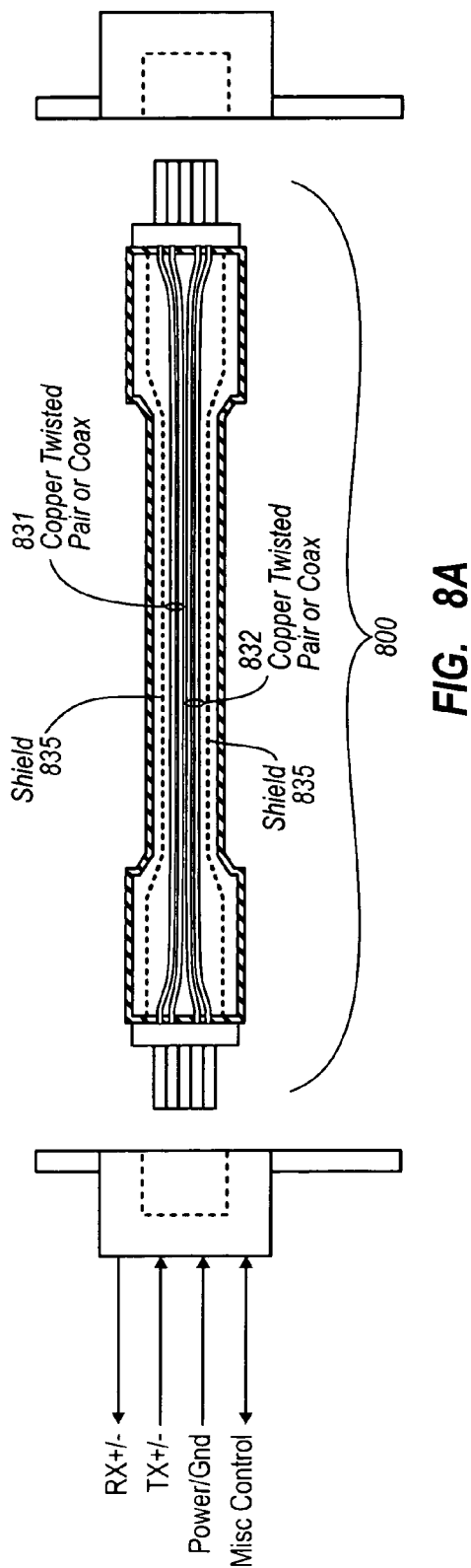
FIG. 8A illustrates a passive electrical-to-electrical copper cable that includes an electrical connector that is structured the same as an electrical connector of the electrical-to-electrical optical cable of FIG. 1 or FIG. 2A.
Figure 8B:
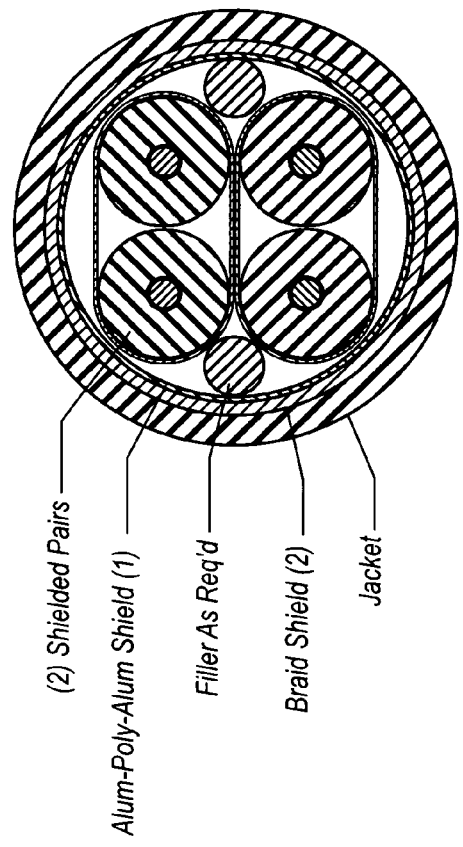
FIG. 8B illustrates a view of an example cross-section of the copper cable of FIG. 8A.

FIG. 8A shows perhaps the simplest implementation of a copper cable 800 designed to interoperate with the optical cables previously described. In this example, the link is entirely passive, with a pair of copper conductors (pairs 831 and 832) carrying the two duplex data streams between each connector. The copper conductor pair couple may be in the form of a shielded or unshielded twisted pair (as used in CAT-5 cabling) or in the form of a single ended or differential coaxial cables. For such a high bandwidth link, it would very advantageous to also include an overall cable shield 835, tied to chassis ground of at last one host to limit electromagnetic emissions. FIG. 8B illustrates a cross-section of what the cable 800 might look like. The other components of the cable 800 may be structured the same as described above for the cable 100.

Figure 9:
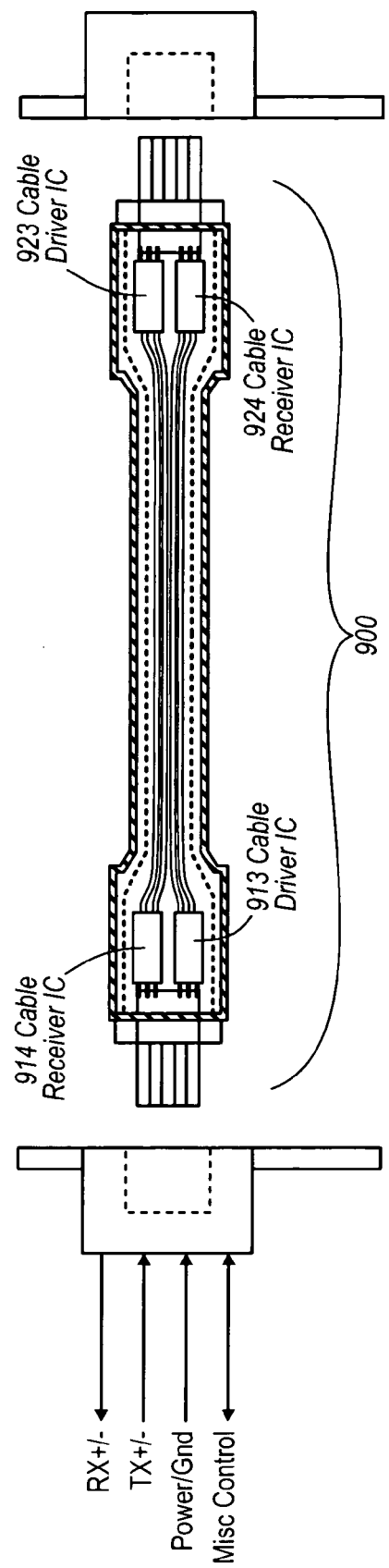
FIG. 9 illustrates an active electrical-to-electrical copper cable that includes an electrical connector that is structured the same as an electrical connector of the electrical-to-electrical optical cable of FIG. 1 or FIG. 2A.

For a 10 G data rate and a reasonable size cable, the possible transmission length without special means in the host system would be very short, perhaps on the order of 1 meter of length. To improve the transmission length, active elements could be incorporated into the cable design as is illustrated into FIG. 9. In FIG. 9, cable driver ICs 913 and 923 and cable receiver ICs 914 and 924 are included in the cable ends. The functionality of these ICs will be described further below. Otherwise, the cable 900 of FIG. 9 may be structured the same as described above for cable 800 of FIG. 8.

Figure 10:
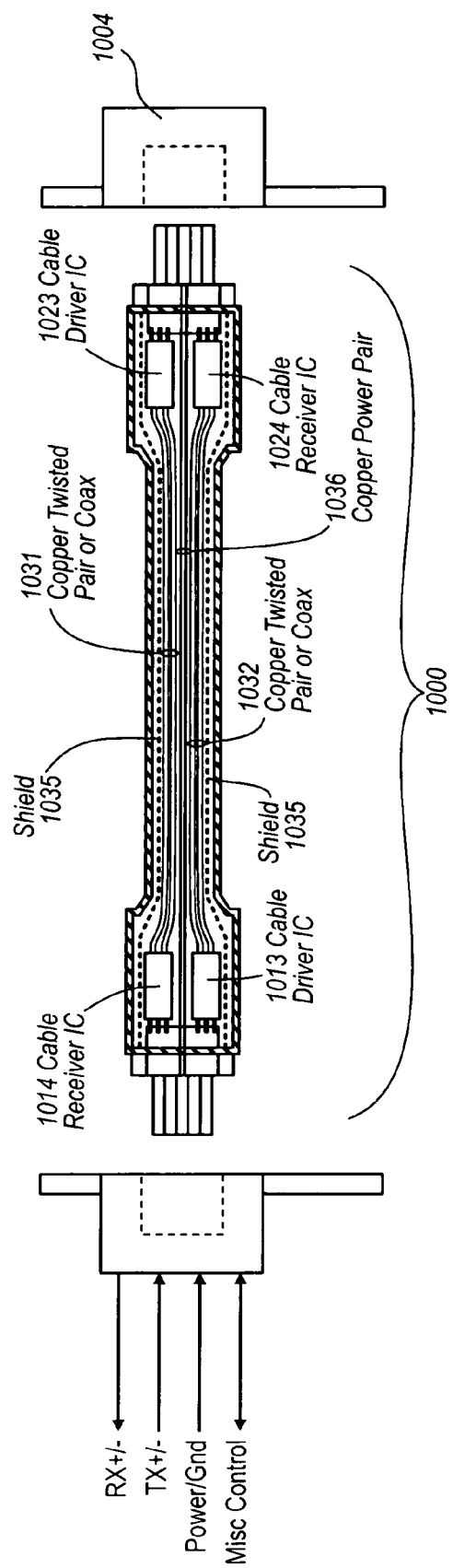
FIG. 10 illustrates an active electrical-to-electrical copper cable that includes a power transmission line and that includes an electrical connector that is structured the same as an electrical connector of the electrical-to-electrical optical cable.

The same considerations for supplying power over the cable discussed previously apply to the copper variants as well; however there are some differences in implementation. For example, if needed, the copper signal conductors in FIG. 8 could be adapted to apply a supply voltage. Alternately, a separate pair of conductors for power could be included as shown in the cable 1000 with active cable drivers 1013, 1014, 1023 and 1024 illustrated in FIG. 10. Since the need for a remote power is particular to two or more cable connections, FIG. 10 shows the remote end of the cable with a female receptacle 1004 to be used as a patchcord. In addition to the copper signal pairs 1031 and 1032, a copper power pair 1036 is provided for providing power from one end of the cable 1000 to the other. A shield 1035 is also provided for EMI protection.

Figure 11:
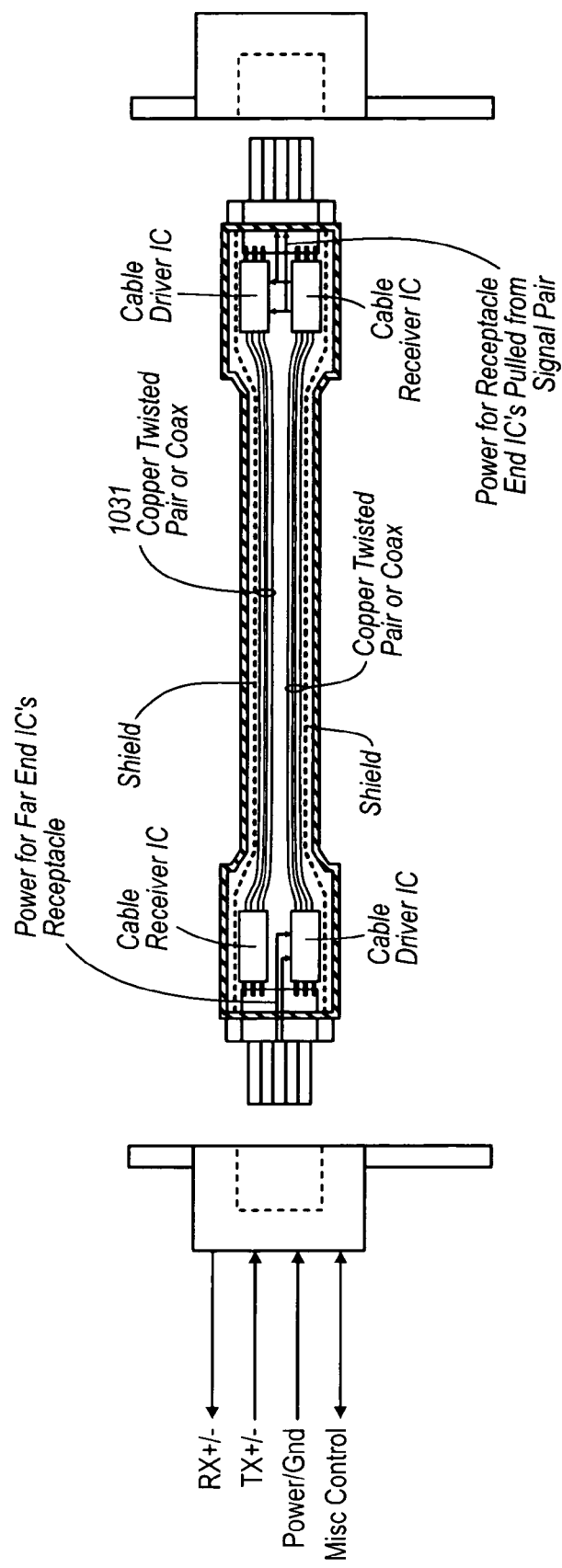
FIG. 11 illustrates an active electrical-to-electrical copper cable that includes a mechanism for transmitting power of the signal carrying lines, and that includes an electrical connector that is structured the same as an electrical connector of the electrical-to-electrical optical cable.

FIG. 11 illustrates the same cable functionality as FIG. 10, but where the power is supplied to the remote end over the signal pairs, rather than having a dedicated power pair. Specifically, power from one end of the cable is provided into the copper twisted pair, and pulled from that twisted pair at the other end of the cable.

FIGS. 12A and 12B illustrates some of the useful features which might be incorporated into the ICs in a copper active cable design. FIG. 12A shows the transmitter Integrated Circuitry (IC). The first block in this IC would provide equalization to compensation for high frequency loss in the host board traces. Such equalization could be fixed, host selectable via a serial interface or automatically adaptive to the host impairments. The next block shown is jitter precompensation. In this relatively new technique, particular data transitions which tend to have the most significant associated deterministic timing errors (jitter) are detected and fixed small time delays are added to compensate. This can be used to compensate for both host board impairments as well as for at least a portion of the bandwidth impairment of the copper cable. The next block is a limiting function which restores the signal levels amplitudes which vary according to the host ICs and may have been further attenuated by the host transmission lines. The final block provides preemphasis to the high frequency content of the transmitted signal to overcome the larger loss on the cable of these high frequencies. This is well known technique and gains of 12 dB or larger may be used. The amount of gain can be adjusted at factory setup individually to match the particular length of the characteristics of the copper cabling.

Preemphasis is accomplished by either boosting the high frequency content or removing low frequency content. In either case, the resulting electrical waveform which results tends to show a large overshoot in after the transmission edge.

It should be noted that only a subset of the functional blocks may be included in the cable driver IC represented in FIG. 12A particularly since some of their effective functionality is overlapping.

Also shown in FIG. 12A, but likely not fully integrated into the IC itself would be optional circuit elements for combining a DC power connection into the signal power cable. The most straightforward means would be the use of a bias T where a large inductor or chain of inductors and other matching components is used to couple in DC current into the copper cable without significantly perturbing the high frequency characteristics of the high speed transmission lines.

FIG. 12B shows the elements which could be included in an active cable IC receiver for the copper implementations of the cable. The elements follow somewhat in the reverse of the driver IC, but with important differences.

Beginning on the left of FIG. 12B, where the copper pair or coax is received from the main length of the cable, there is an optional DC bias circuit to recover far end power from other cable end. This power can be used to supply the receiver IC itself and/or other elements in that cable end, or even components to which the remote cable end is attached, such as a powered adapter for connecting a following length of cable.

The next block shown, completely within the IC, is adjustable equalization. This block of equalization is provided to compensate for the cable high frequency rolloff, rather than the host PCB traces in the case of the driver. As in the case of the driver, it may provide fixed, adjustable or adaptive equalization. Adjustable but factory set equalization is of particular interest because the cable length and characteristics will be established at the time of the cable manufacture.

Following optional equalization, a limiting amplifier restores the zero and one levels to uniform amplitudes. In most such receivers, it is necessary to maintain an appropriate DC level at the circuit inputs to maintain proper duty cycle operation. This is typically implemented as shown by a DC restore loop which also establishes a low frequency cut-on of the high speed channel, which must be chosen appropriate for the minimum data rate and coding scheme.

Finally, for driving the host PCB traces at this end of the cable, an output driver is provided with optional preemphasis. In the case of the receiver, the preemphasis would be provided to help overcome high frequency losses on long PCB traces which can add significant jitter at 10 G operation. The preemphasis could be fixed, adjustable with adjustment at the factory or based on host control information on the expected loss characteristics of the PCB channel.

Figure 13A:
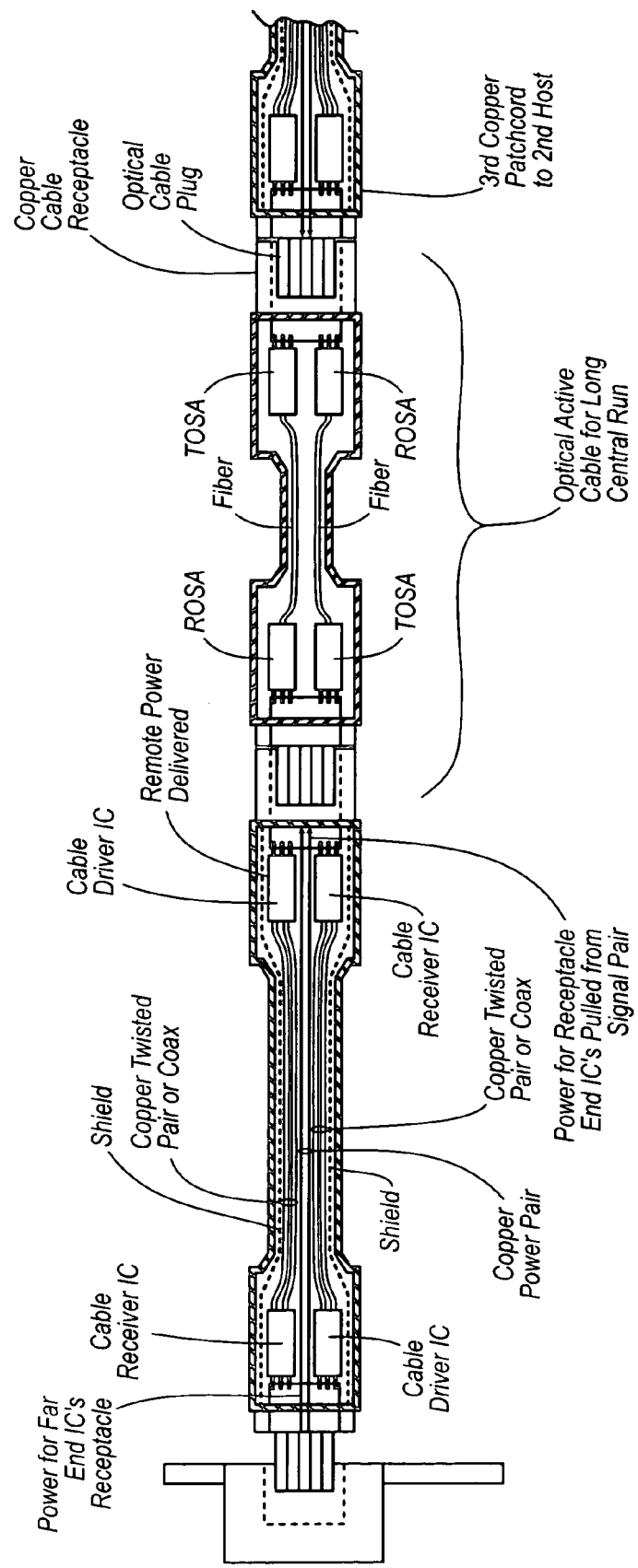
FIG. 13A illustrates a three cable link that includes electrical-to-electrical copper cables on the ends and an optical cable with electrical connectors in the middle, in which power is supplied to the electrical connections in the optical cable using dedicated power transmission lines.

FIGS. 13A and B illustrates what might be the most economical arrangement to achieve the advantages of a three cable connection. In this case, copper based patchcords are used for relatively short (1-5 meters) connections from host equipment to patchpanels, where they would join to a long length (5-100 meters) of fiber optic based active cable. In addition to potentially lower cost than a very short optical active cable, the copper cable may more easily provide the power to the central cable run. FIG. 13A shows the arrangement where such power is carried by a dedicated conductor pair, whereas FIG. 13B shows the power transferred over one of the high speed signaling pairs.

Figure 13B:
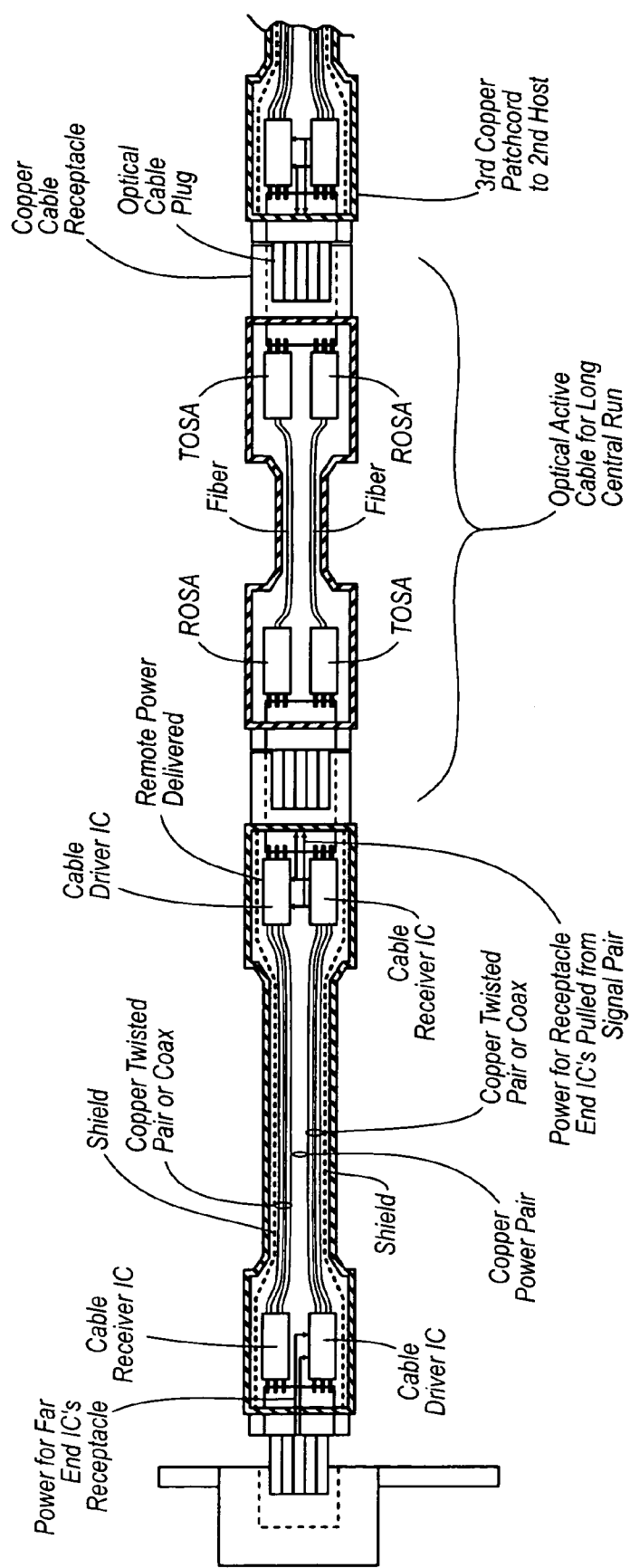
FIG. 13B illustrates a three cable link that includes electrical-to-electrical copper cables on the ends and an optical cable with electrical connectors in the middle, in which power is supplied to the electrical connections in the optical cable using the signal carrying lines of the copper cables.

While FIGS. 13A and 13B show the short copper connections as a male to female connector arrangement, which directly connects to a standard male to male central cable, it should be obvious to one skilled in the arts that the adapter arrangements illustrated in FIGS. 3 and 4 may be similarly employed. Similarly, it should also be cleared that implementations in FIGS. 6 and 7 which employee retimers for added jitter reduction are also possible and with the same potential advantages.

Thus, the user need not be concerned about choosing whether copper-based solutions or optical solutions are more appropriate, and then choose to configure the system with the appropriate ports. Instead, the user may just plug in the cable, and enjoy all of the benefits of optical communication such as, for example, high bandwidth communication with low power consumption and high port density, and with less pre-processing and post-processing of information. Alternatively, the user could choose a copper based version of the cable for particularly short links (say from the top to the bottom of a rack of switching equipment) if economically advantageous.

Figure 14A:
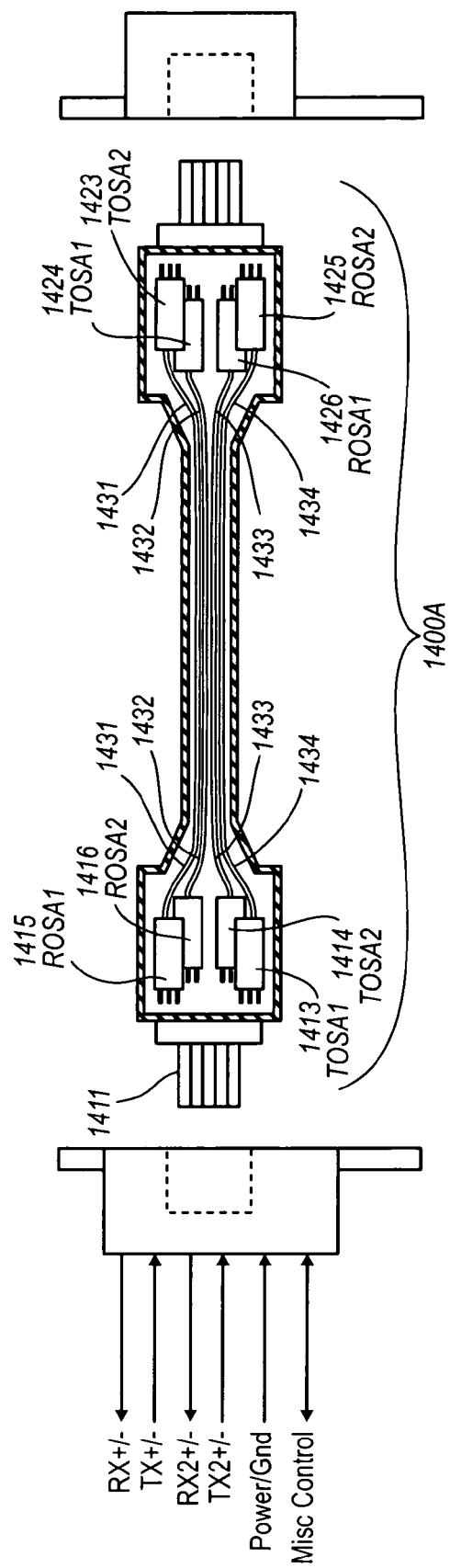
FIG. 14A illustrates a dual link electrical-to-electrical optical cable.

A useful variation of these optical link cables with electrical interface is the possibility of carrying more than one bidirectional signal in a single cable. In particular, the size of the optical subassemblies, the low power dissipation possible and the density of pinout may allow the relatively easy implementation of two links within a connector width of approximately less than one half inch, or roughly the size of the very common RJ-45 network connector. For example, as shown in FIG. 14A, the electrical connector 811 is defined with two sets of differential input and outputs (e.g., RX, RX2, TX and TX2) each representing independent bidirectional links, and the connector end may then contain two sets of TOSAs 1413 and 1414 and/or ROSAs 1415 and 1416, which in turn are connected to 4 separate fibers 1431 through 1434. Alternatively, the two channels may be integrated in a single TOSA with a dual channel laser driver and two VCSELS, either discrete or on the same subassembly. It will be apparent to one skilled at the art after having read this description that the principle of having two (or more) channels in a cable may be applied to all the variants of the cables described above as well as to the various means of interconnecting cables directly or through a separate adapter. Two sets of TOSAs 1423 and 1424 and ROSAs 1425 and 1426 may be included in the other end of the cable as well, thus establish a dual link duplex active cable 1400A. It should be clear that implementations with more than 2 links in a single assembly are also possible.

Figure 14B:
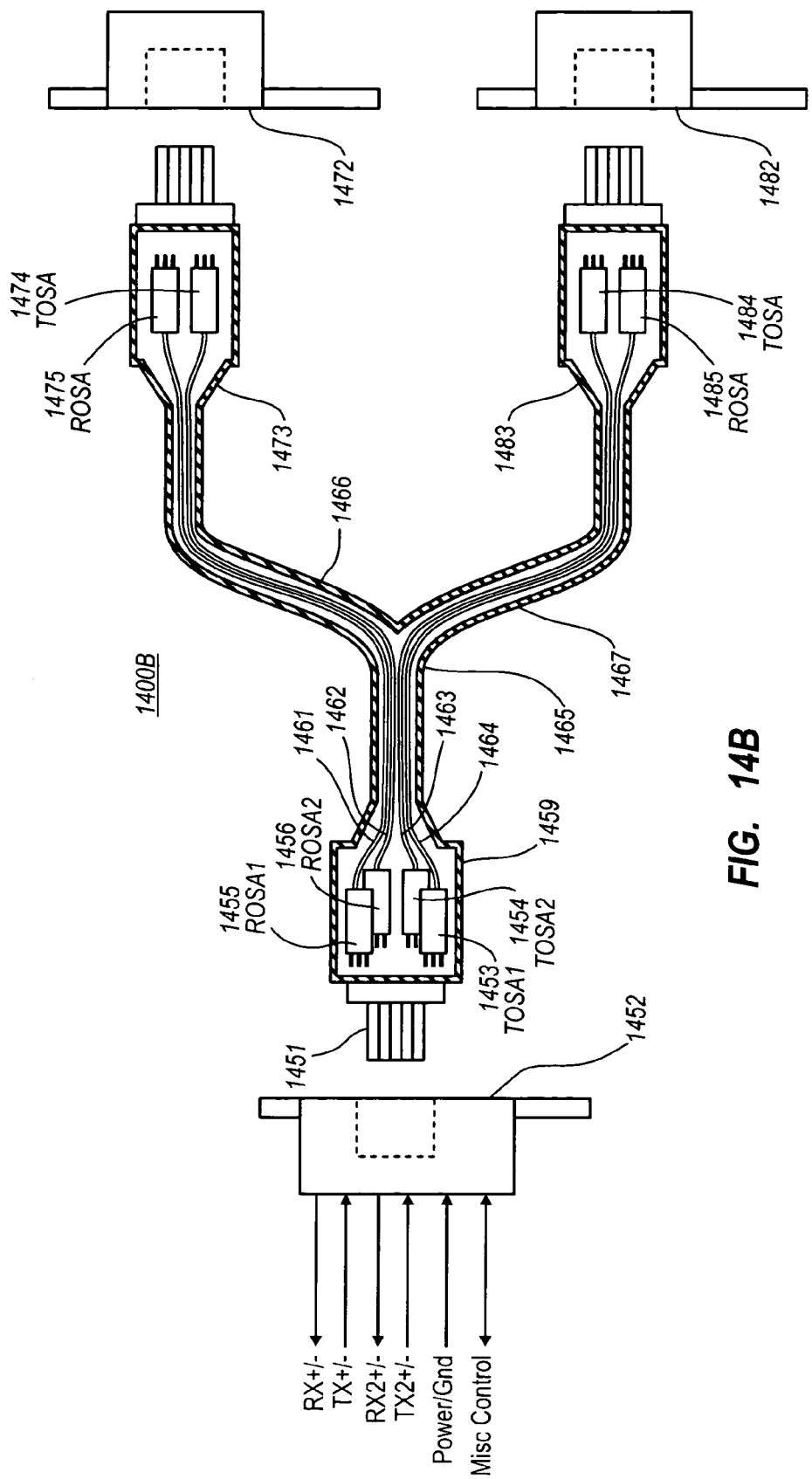
FIG. 14B illustrates a dual link electrical to two single link electrical cable.

FIG. 14B illustrates an embodiment that is similar to FIG. 14A in that one end 1459 supports two independent channels, but somewhere along its length 1465, the cable splits into two single channel cables 1466 and 1467, each terminating in a single channel connector 1473 and 1483, respectively, each having a single TOSA and ROSA. For instance, cable end 1473 may be received by receptacle 1472 and includes TOSA 1474 and ROSA 1475, whereas cable end 1483 may be received by receptacle 1482 and include TOSA 1484 and ROSA 1485. Each TOSA 1474 and 1484 is connected through a respective optical fiber 1462 and 1461 to a corresponding ROSA 1456 and 1455 in the dual link end 1459 of the cable 1400B. Each ROSA 1475 and 1485 is connected through a respective optical fiber 1463 and 1464 to a corresponding TOSA. The electrical connector 1451 of the dual link end 1459 of the cable is received by the electrical receptacle 1452 of the host. Note that the host transmits two differential high speed data signals TX and TX2, and receives two differential high speed data signals RX and RX2.

Finally, there are a number of characteristics of the electrical connector system which would be favorable for such an application. First, there might be a latching mechanism such as the tab style latch found in an RJ-45 style connector or a push-pull style latch employed in the SC style fiber optic connector.

Second, the receptacle on the host system may include provisions for visual indicators of link activity and other status. This may be accomplished by two means common in the RJ-45 connector system. The first is inclusion of LEDs in the front panel face of the host receptacle with electrical connections to the host PCB. A second method is to include plastic light pipes within the receptacle assembly to guide light from LEDs on the host PCBA to the front surface of the receptacle.

Third, the cable may have a provision for some sort of keying system to allow or prevent different types of host systems from being interconnected. One example where a keying system would be important is to prevent the insertion of a single link cable in a dual link port. Another example would be the prevention of the connection of two host systems running different protocols, though this could be detected by protocol means themselves. For example, exactly the same cable may be useful for Ethernet and Fiber Channel applications, yet a system's administrator running a datacenter with both types of equipment may wish to prevent the interconnection of these systems by simple mechanical means. Of course color coding or other simple means could be used for this purpose as well. Keying features on a connector often comprise a mechanical protrusion on one of a set of locations on the host receptacle and corresponding slots on the cable plug, or vice versa. Examples of these features can be found in the definition of the HSSDC2 connector (see Small Form Factor Committee document SFF-8421 rev 2.6, Oct. 17, 2005).

There are many possible choices for the electrical connector in terms of the number of pins, their function and their relative arrangement.

Figure 15A:
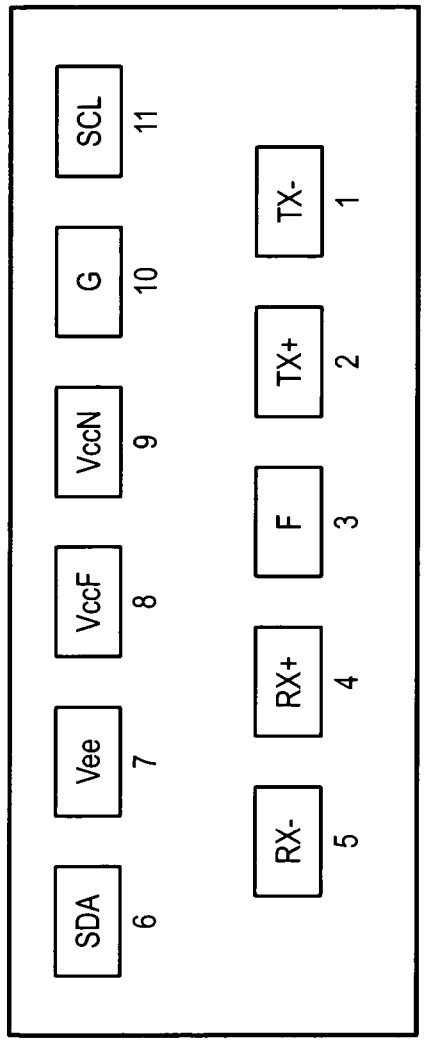
FIG. 15A illustrates an example 11 pin arrangement of a single link cable.
Figure 15A:
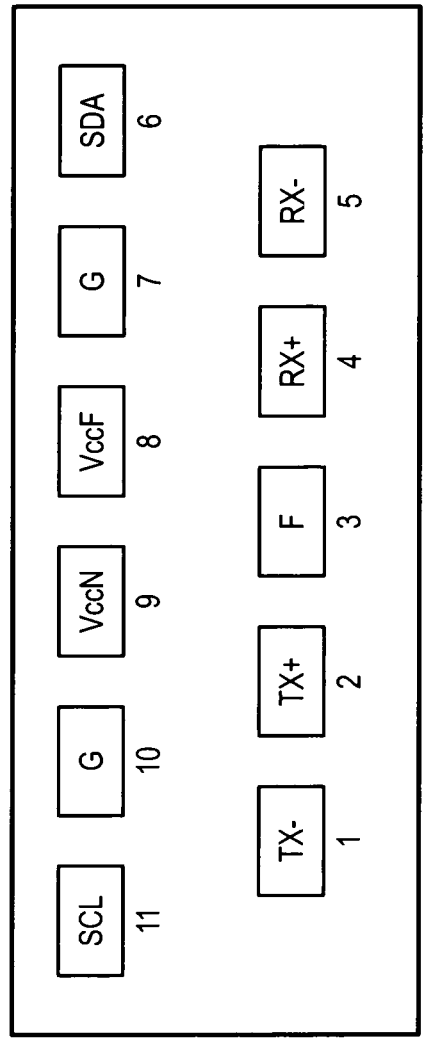

FIG. 15A shows one possible pin arrangement involving 11 contacts, both from the view of the cable plug end (top) as well as looking into the host receptacle (bottom). Some pins are necessary for any implementation such as the power for the near end circuitry, Vcc, the ground connections, Vee, the high speed differential transmit signals, TX+ and TX− and the high speed differential receive signals, RX+ and RX−. Other optional signals of use in some implementations are a separate power connection for far end power connections, VccF, a Fault/Interrupt pin, F/INT to indicate any problems with the link, and in the case of the Interrupt function, to prompt the host to query for more information, a serial data interface. In this case, a pair of pins representing a serial data line SDA and an associated serial data clock SCK such as used in the I2C communication system.

The far end power connection, VccF has been described previously as providing an isolated or alternative voltage to supply the active components within or beyond the far end of the cable, primarily for applications which concatenate multiple cables in the various manners described above.

Figure 15B:
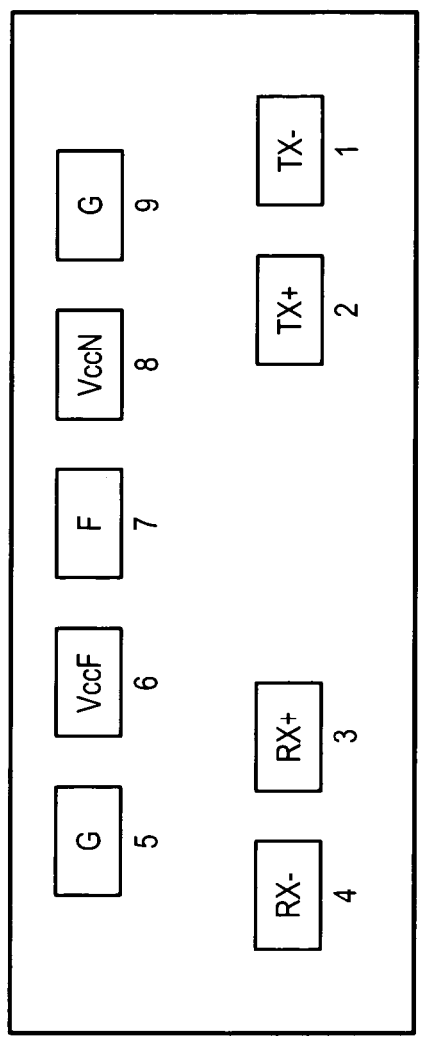
FIG. 15B illustrates an example 9 pin arrangement of a single link cable.
Figure 15B:
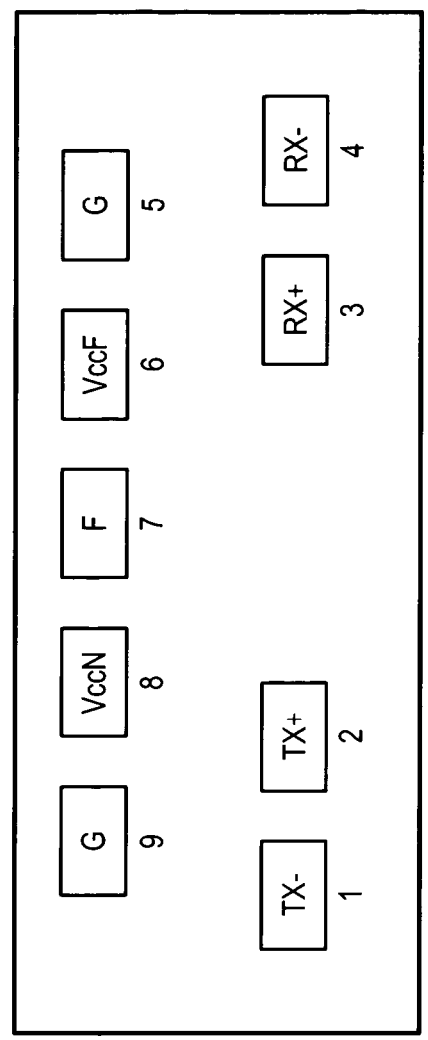

FIG. 15B shows a slightly different but important simplified pinout with only 9 connections. In this case, there are no separate connections for a serial data interface. Nevertheless it possible to still those connections over one of the set of high speed data pins through various possible means. These include, but are not limited to common mode signaling of the low speed interface on the differential high speed lines, or modulation of the low speed interface below the low frequency cut-on of the high speed data frequency content (which is typically modulated to achieve DC balance with no appreciable signal content below a given frequency typically now lower than about 30 kHz for these applications).

The seeming disadvantage of not having separate pins for the serial data path or the complexity of combining the low and high speed paths may be more than offset by the savings in the connector design by reducing to the minimum possible pin count.

Figure 15E:
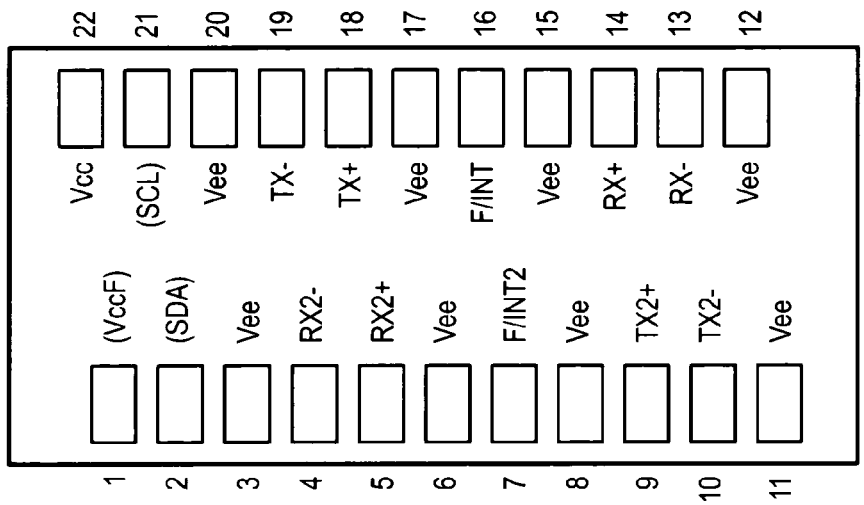
FIG. 15E illustrates an example 22 pin arrangement of a dual link cable.
Figure 15D:
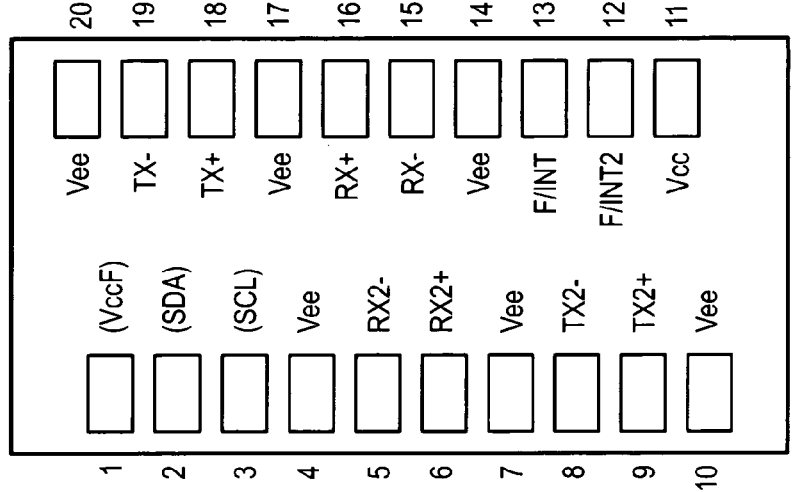
FIG. 15D illustrates an example 20 pin arrangement of a dual link cable.
Figure 15C:
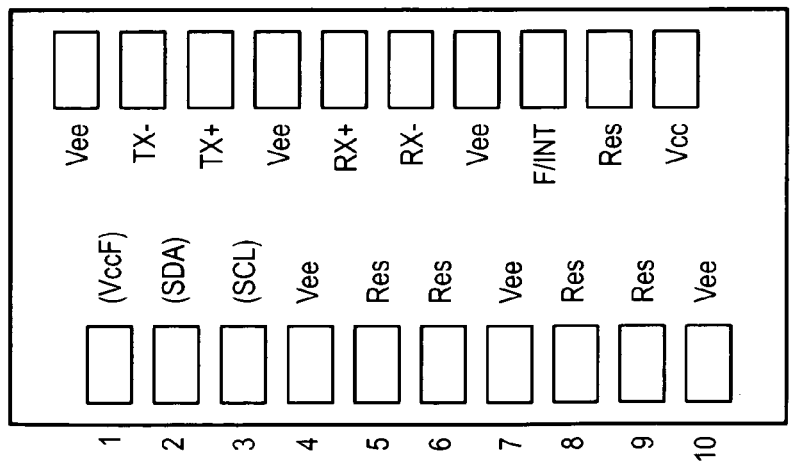
FIG. 15C illustrates an example 20 pin arrangement of a single link cable.

FIG. 15C shows one possible pin arrangement for a single channel cable using a 20 contact connector. This particular physical arrangement of pin contacts is of interest because it is based on the same layout as the PCB edge connector of the SFP and XFP form factors which have been proven to have good performance at 10 G serial data rates.

While numerous arrangements of these pins may be practical, FIG. 15C illustrates high speed pairs TX+, TX−, RX+ and RX− are surrounded by ground lines Vee, which is useful both in achieving the desired impedance (for example 100 Ohms differential) of the differential lines, as well as reducing crosstalk between high speed lines. Several lines Res are shown as reserved for future functions. Two-wire interface lines (SDA) and (SCL) may provide serial data to the electrical connector for controlling the optics and for other desired functions.

FIG. 15D shows a similar pin arrangement, but one designed for cables carrying two full duplex links. Specifically, pins TX2+, TX2−, RX2+ and RX2− are used for a second duplex link, as well as a separate Fault line F/INT2. Finally, FIG. 15E shows a 22 pin arrangement for a dual link which differs from FIGS. 15C and 15D in that it provides more ground separation between the high speed pairs. It should be obvious to one skilled in the arts that a simplified version for a single link can be derived from FIG. 15C and that certain aspects of the arrangements are arbitrary.

Thus, the cable permits high-speed communication using optics while not requiring that the network nodes interface with the cable using optics. Instead, the user may simply plug the cable into electrical connections. The cable may also include additional functionality to improve the performance and safety of the cable.

Figure 16:
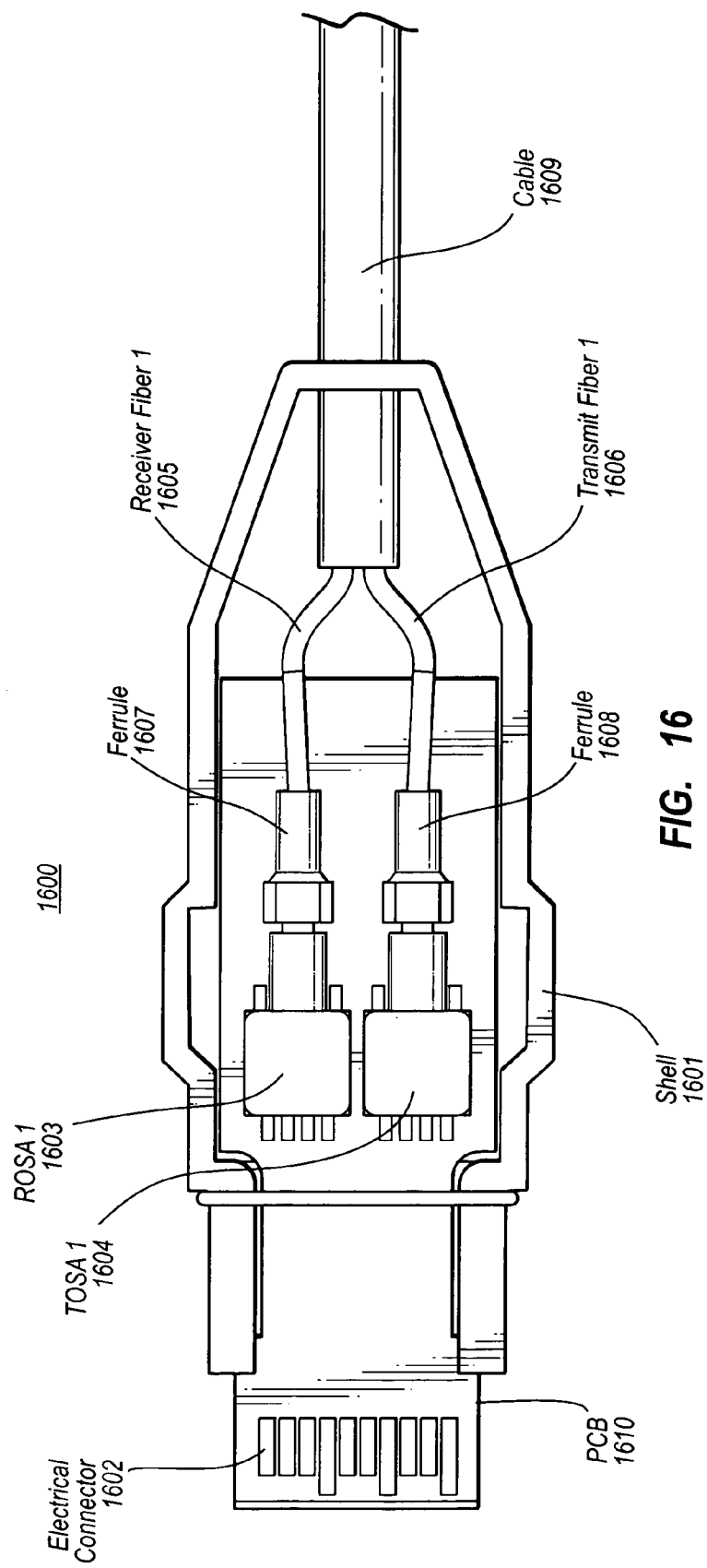
FIG. 16 illustrates a schematic of the internals of one end of a single link cable including the electrical connector.

FIG. 16 illustrates a view of one end 1600 of one embodiment of a single link active cable. A top part of the shell 1601 is cut away for illustrative purposes so that the internals of the end 1600 may be viewed. The end 1600 has 10 electrical traces disposed on each side of printed circuit board 1610, allowing for a total of 20 electrical traces. In this case, the PCB edge contact design is the same as that in the existing SFP form factor standard, though that is not a requirement of such a design. Thus, the end 1600 may support the connection configurations of FIG. 15C or 15D. The end 1600 includes ROSA 1603 and TOSA 1604, which are coupled to the corresponding receive optical fiber 1605 and the transmit optical fiber 1606 via ferrules 1607 and 1608, respectively. The optical fibers 1605 and 1606 form part of cable 1609, which is protected by the cable jacket. The cable typically would also incorporate a strength member such as Kevlar yarn which would be anchored to the interface between the external portion of the cable and the plug shell.

Figure 17A:
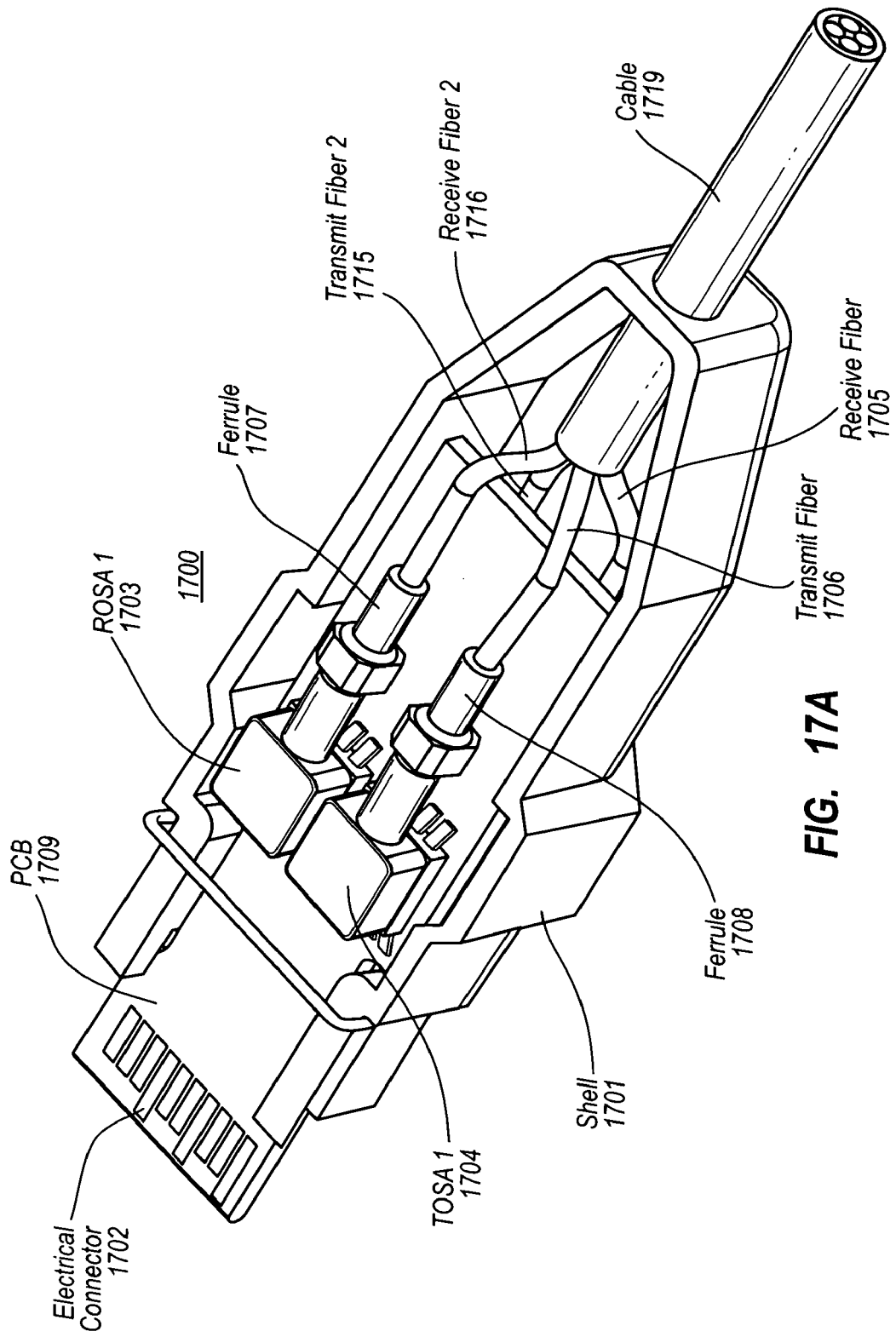
FIG. 17A schematically illustrates the internals of one end of a dual link cable including the electrical connector.

FIG. 17A illustrates a view of one end 1700 of an embodiment of a dual link fully-duplex active cable. Once again, the top part of the shell 1701 is cut away for illustrative purposes. The end 1700 has 10 electrical traces disposed on each side of an electrical connector 1702 portion of the printed circuit board 1709, allowing for a total of 20 electrical traces. Thus, the end 1700 may support the connection configurations of FIGS. 15C and 15D. However, another electrical trace could be added to each side of the electrical connector 1702 to permit a total of 22 traces to thereby support the connection configuration of FIG. 15E. The end 1700 includes ROSA 1703 and TOSA 1704, which are coupled to a corresponding receive optical fiber 1705 and the transmit optical fiber 1706 via ferrules 1707 and 1708, respectively, on one side of the printed circuit board 1709. Symmetrically, another set of ROSA and TOSAs is disposed on the far end of the support board, though not shown in this illustration, which may be similarly coupled to corresponding fibers 1715 and 1716 via corresponding ferrules. The optical fibers 1705, 1706, 1715 and 1716 form part of cable 1719, which is protected by the cable jacket.

Figure 17B:
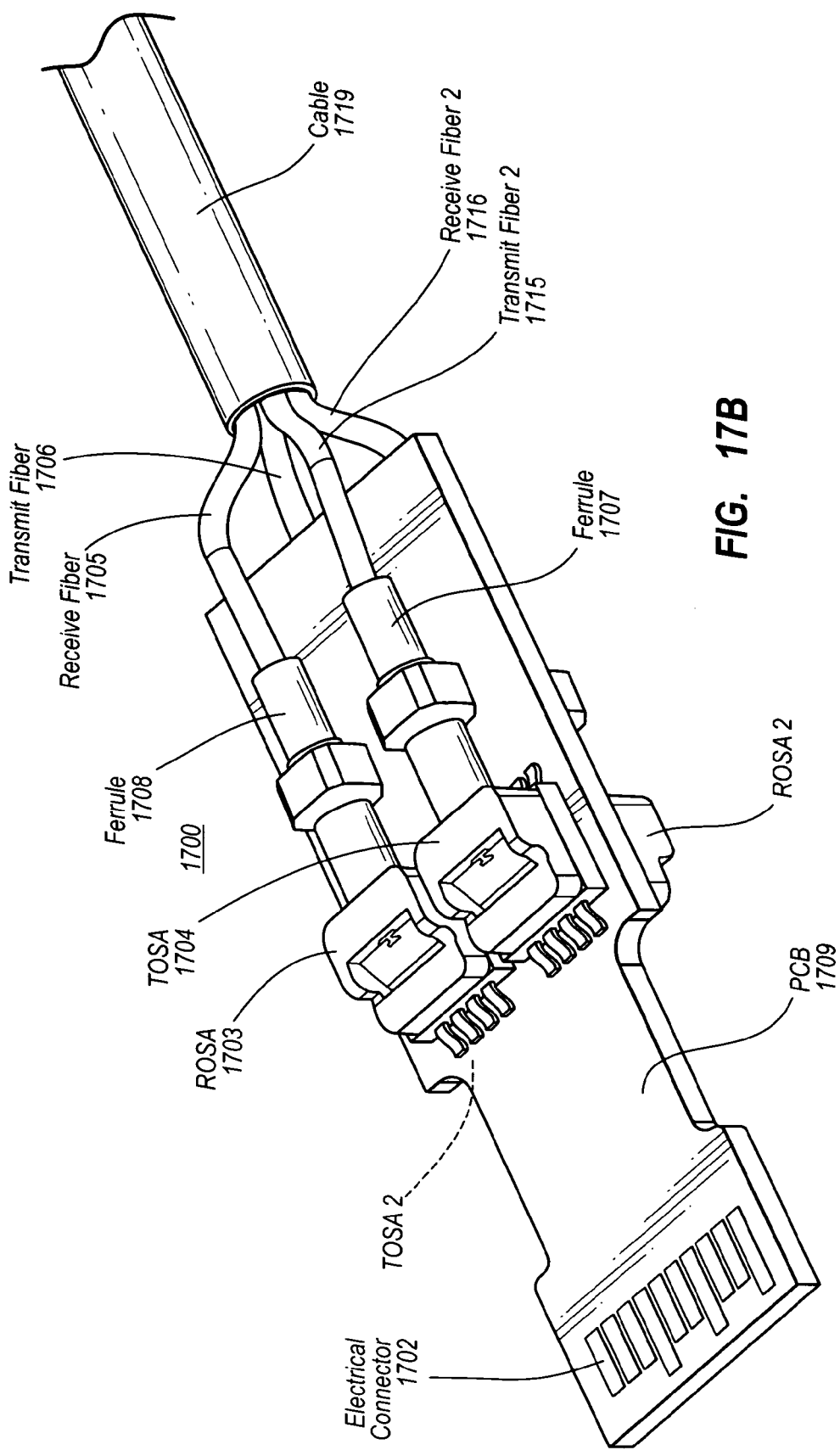
FIG. 17B illustrates another perspective view of the electrical connector end of FIG. 17A.
Figure 17C:
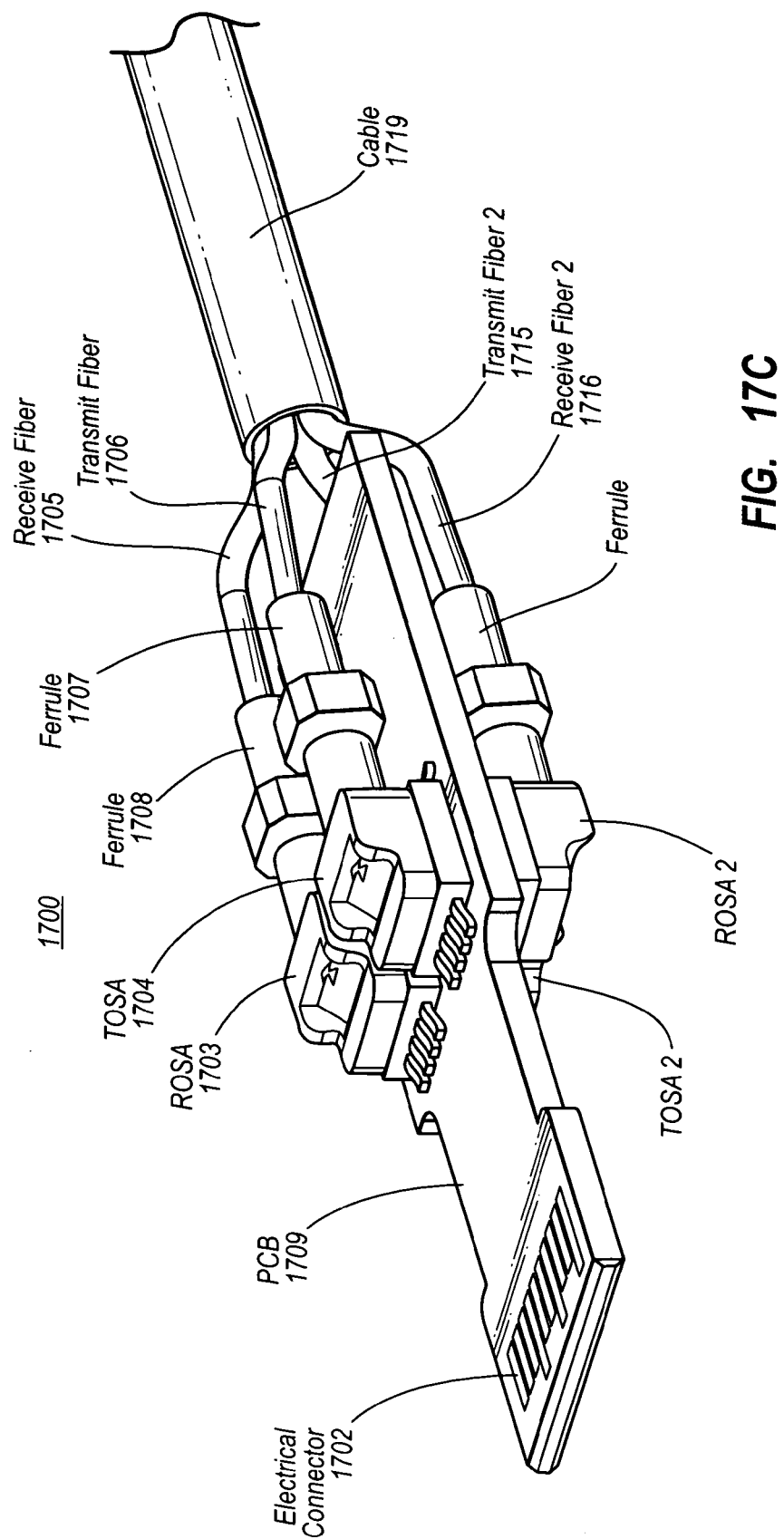
FIG. 17C illustrates yet another perspective view of the electrical connector end of FIG. 17A.

FIG. 17B illustrates a perspective view of the end 1700 of FIG. 17A, only with the shell 1701 entirely removed. Here, the ROSAs on both sides of the printed circuit board may be viewed. The TOSA on the far end of the printed circuit board is still not viewable, but it may be simply placed opposite the respective ROSA on the near side of the printed board. FIG. 17C illustrates another perspective view of the end 1700 of FIG. 17A.

Figure 18:
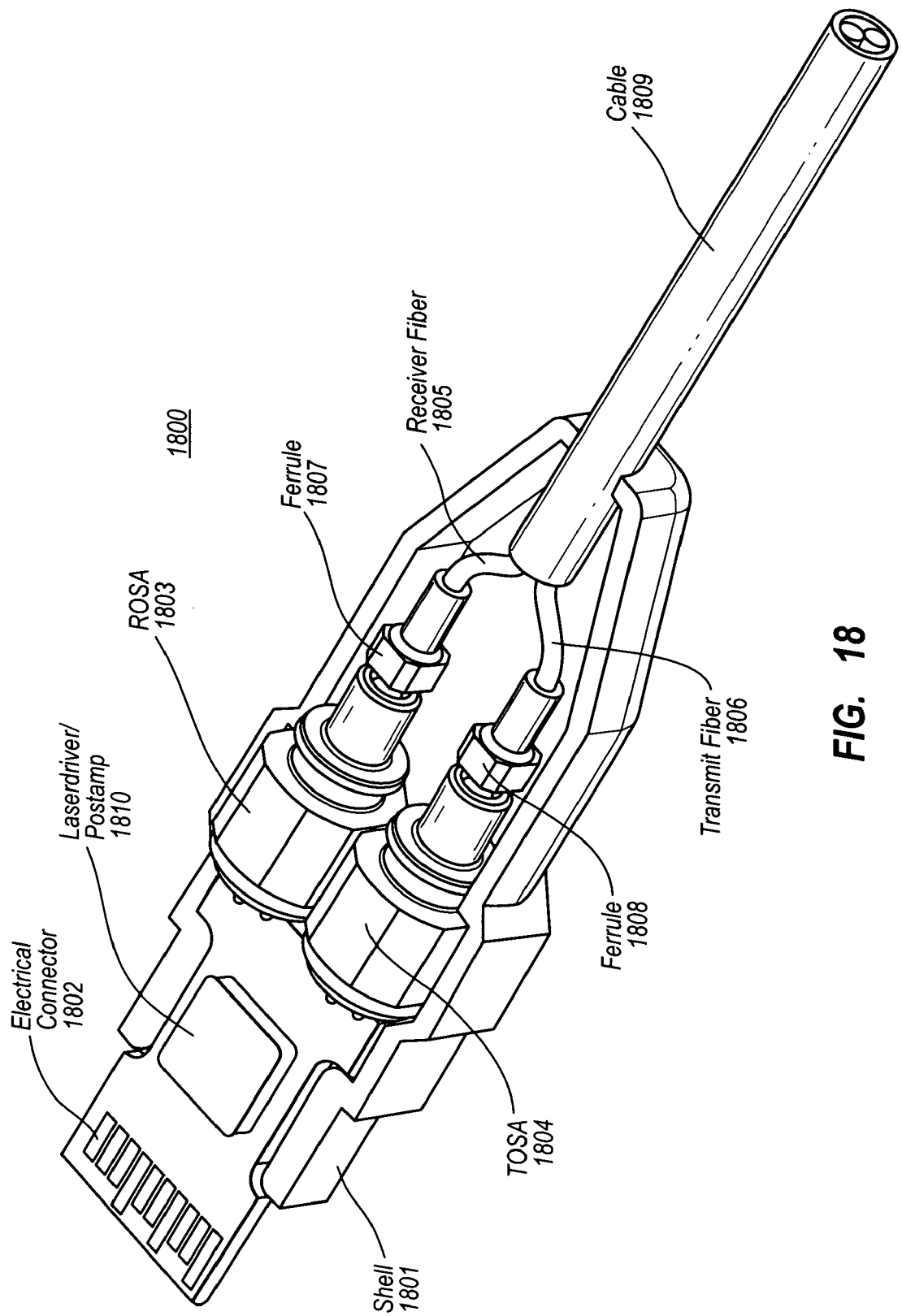
FIG. 18 illustrates a perspective view of an electrical end a single link cable in accordance with the principles of the present invention.

FIG. 18 illustrates a view of one end 1800 of an embodiment of a single link fully-duplex active cable, with its protective shell removed for easier visualization. The electrical connectors 1802 may be similar to the electrical connectors 1602 of FIG. 16. Here, the laser driver and post amplifier are integrated into a single integrated circuit 1810. An EEPROM, which might be used to store setup or serial ID information, could be mounted on the far side of the printed circuit board. The end 1800 includes ROSA 1803 and TOSA 1804, which are coupled to the corresponding receive optical fiber 1805 and the transmit optical fiber 1806 via ferrules 1807 and 1808, respectively. The optical fibers 1805 and 1806 form part of cable 1809, which is protected by the cable jacket.

FIG. 2C above illustrated how a variant of the optical cable with an optical interface compliant with optical link standards could be used to interconnect a host system with an electrical active cable receptacle to another system with an industry standard optical transceiver. This very useful application can also be achieved through the use of an adapter which plugs into the cage system of a standard form factor optical transceiver and which satisfies all the signaling requirements of that interface. In addition to connecting a system with a dedicated active cable receptacle to that with an industry standard optical transceiver, two such adapters could be used to interconnect any present day systems with such industry standard transceivers. In general, such adapters may satisfy the mechanical electrical signaling requirements of the various form factor standards which have generally been established through multisource agreements in the industry (references above).

Figure 19:
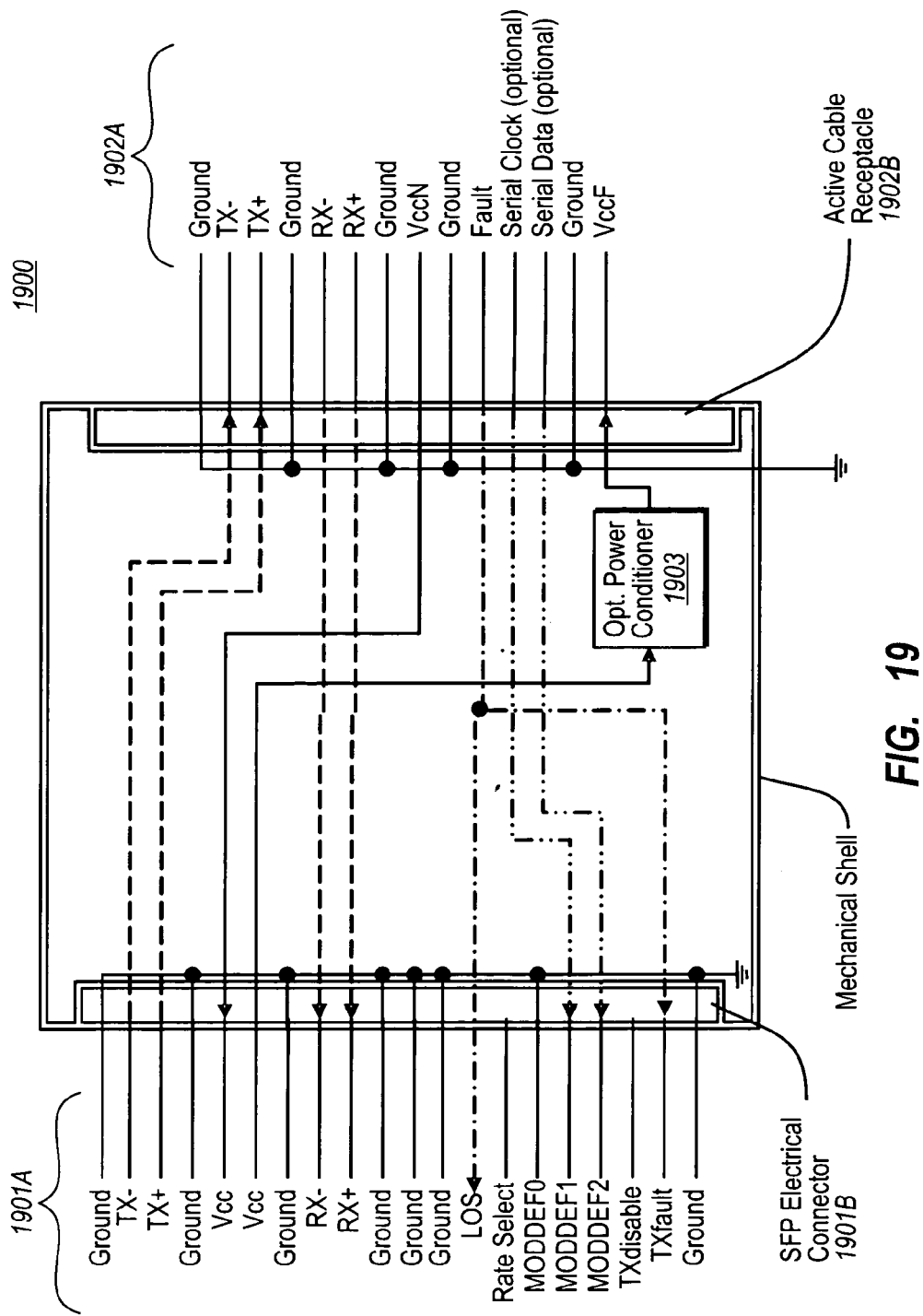
FIG. 19 illustrates an SFP to active cable adaptor electrical conversion mapping component.

FIG. 19 illustrates a signal mapping diagram of an adaptor 1900 that adapts between the common SFP standard and the active cable signals illustrated with respect to FIGS. 15A-C. On the left side of the adaptor 1900 are the standard SFP signals 1901A coupled to an SFP connector abstractly represented by reference number 1902A. On the right of the adaptor 1900 are the active signals 1901B of FIG. 15A-15C coupled to the active cable connector abstractly represented by reference number 1902B. The adaptor 1900 may include an optional power conditioner 1903 if power regulation is needed between the SFP power supply Vcc and the active cable power supply VccF.

Figure 20A:
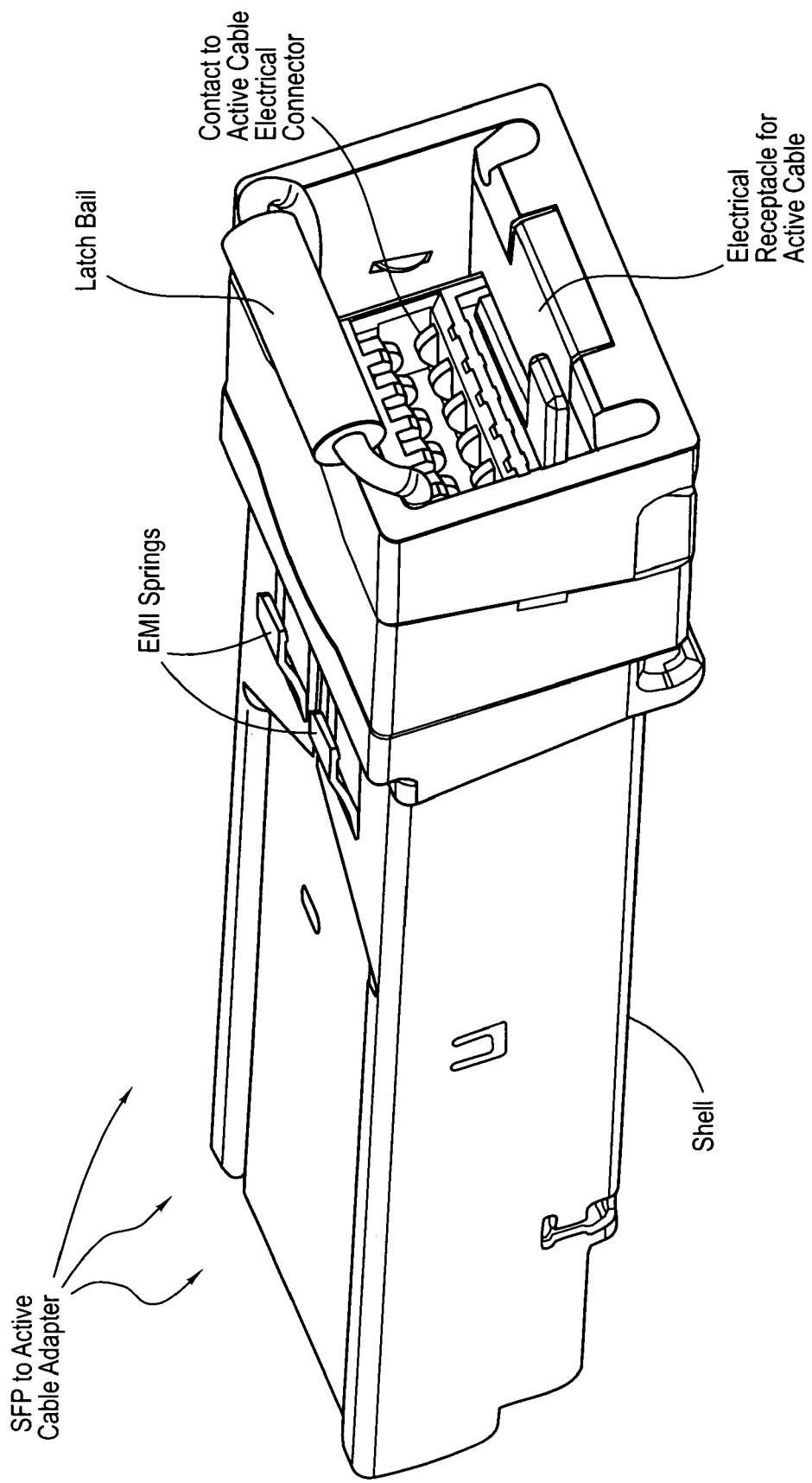
FIG. 20A illustrates a first view of an SFP to active cable adaptor in accordance with one embodiment of the present invention.

FIG. 20A illustrates a first embodiment of a mechanical design of an SFP to active cable adaptor. Here, a shell is shown protecting hidden internal circuitry and components. The proximate end of the adaptor shows the electrical receptacle for the active cable, with a latch bail to actuate the retention mechanism of the overall adapter (a standard feature of the SFP mechanical interface). A separate. latch mechanism, [Shown only as a small catch in the view FIG. 20B] is provided for retaining the cable to the adaptor. Several contacts are shown which contact the respective electrical traces of the active cable end when the active cable is inserted into its corresponding electrical receptacle on the adaptor. EMI spring are shown that ensure electrical contact of the shell to the host, to thereby ensure that the shell carries a voltage that at least partially prevents electromagnetic emissions from the host system or adaptor itself from exiting the system.

Figure 20B:
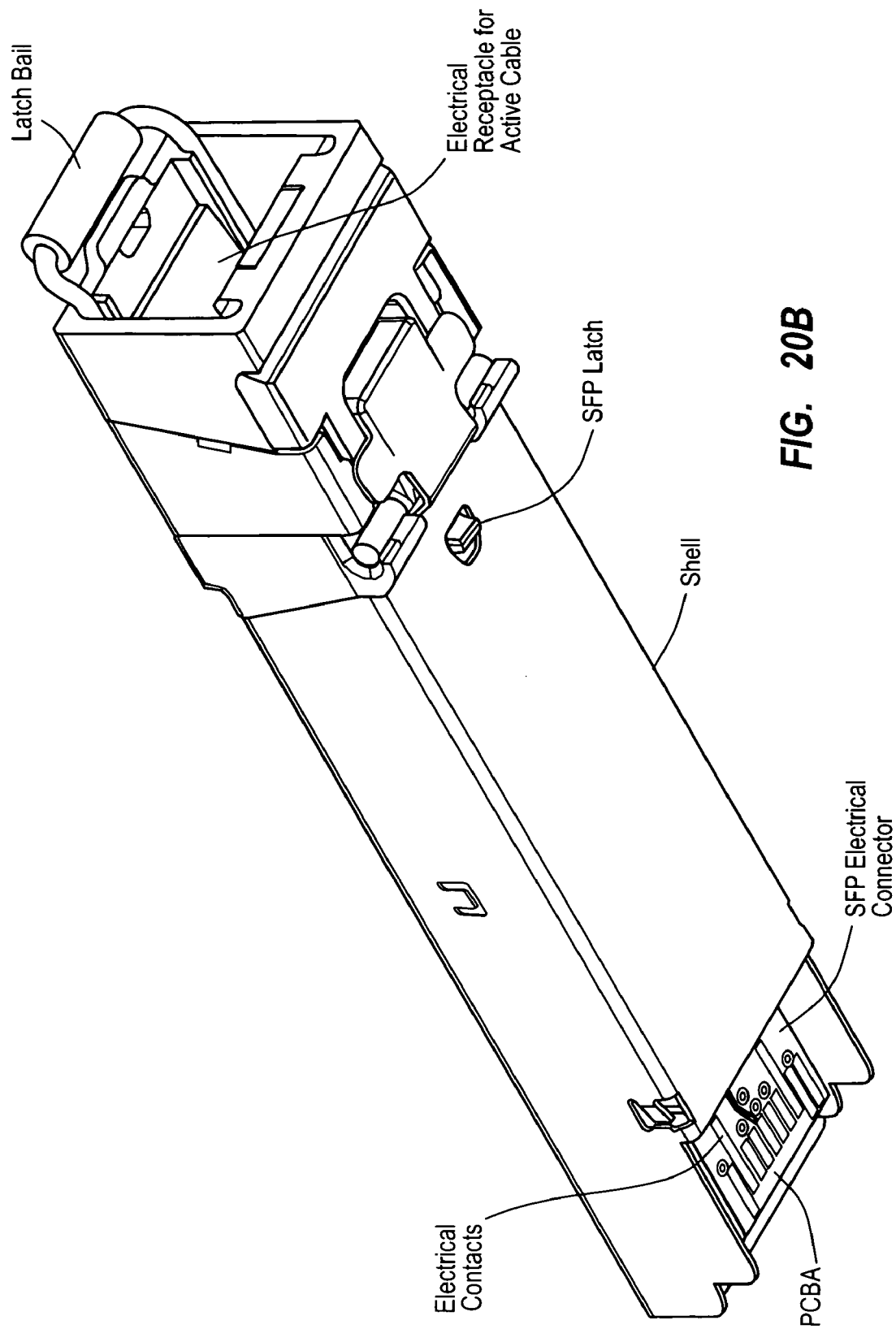
FIG. 20B illustrates another perspective view of the adaptor of FIG. 20A.

FIG. 20B illustrates another perspective view of the mechanism design of the adaptor of FIG. 20A. Here, the SFP end of the adaptor is shown in detail. The SPF end includes a Printed Circuit Board (PCBA) that has multiple electrical contacts suitable for reception of any SFP-compliance connector. An SFP latch is also shown, which complies with the SFP standard.

Figure 20C:
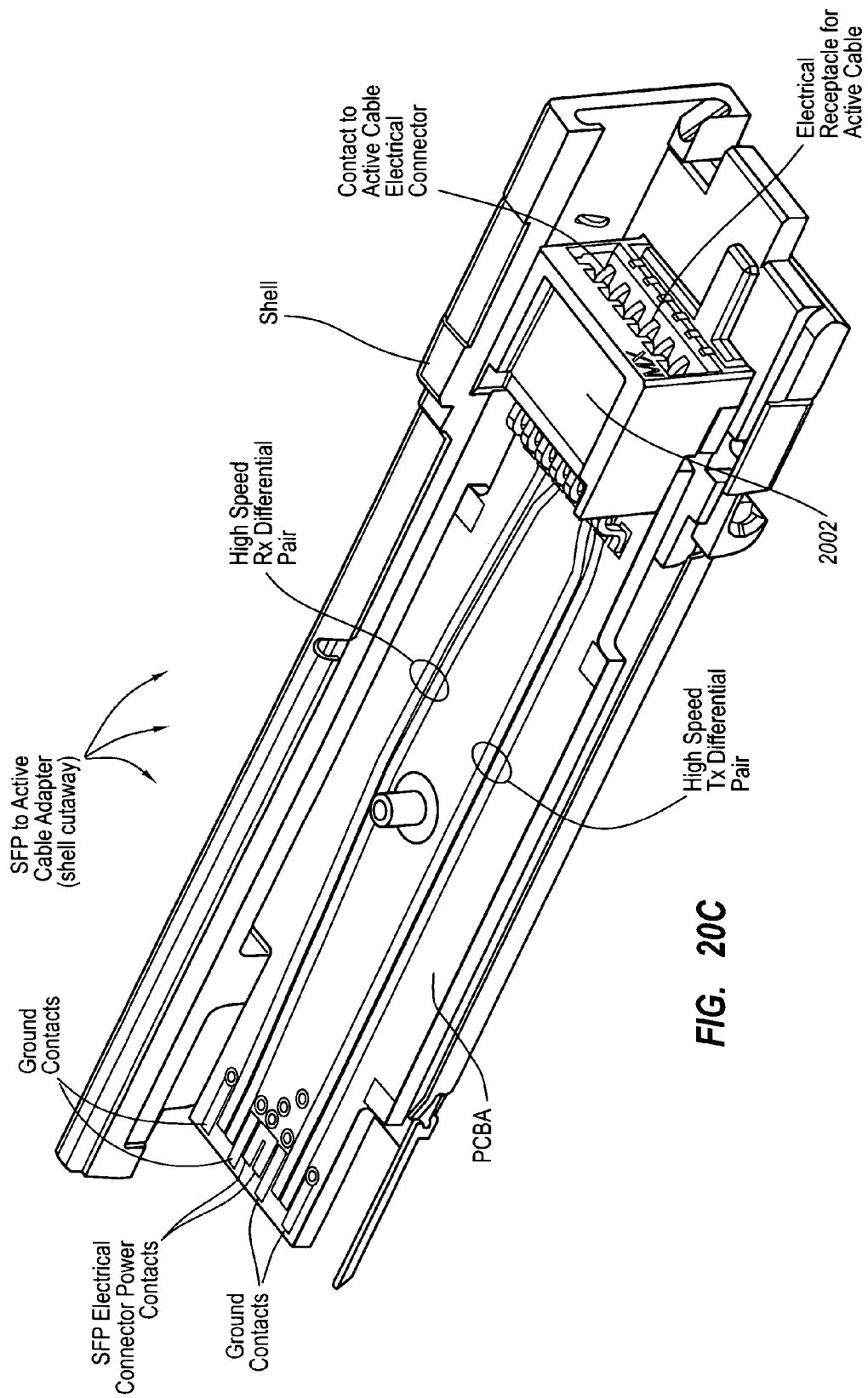
FIG. 20C illustrates yet another perspective view of the adaptor of FIG. 20A.
Figure 20D:
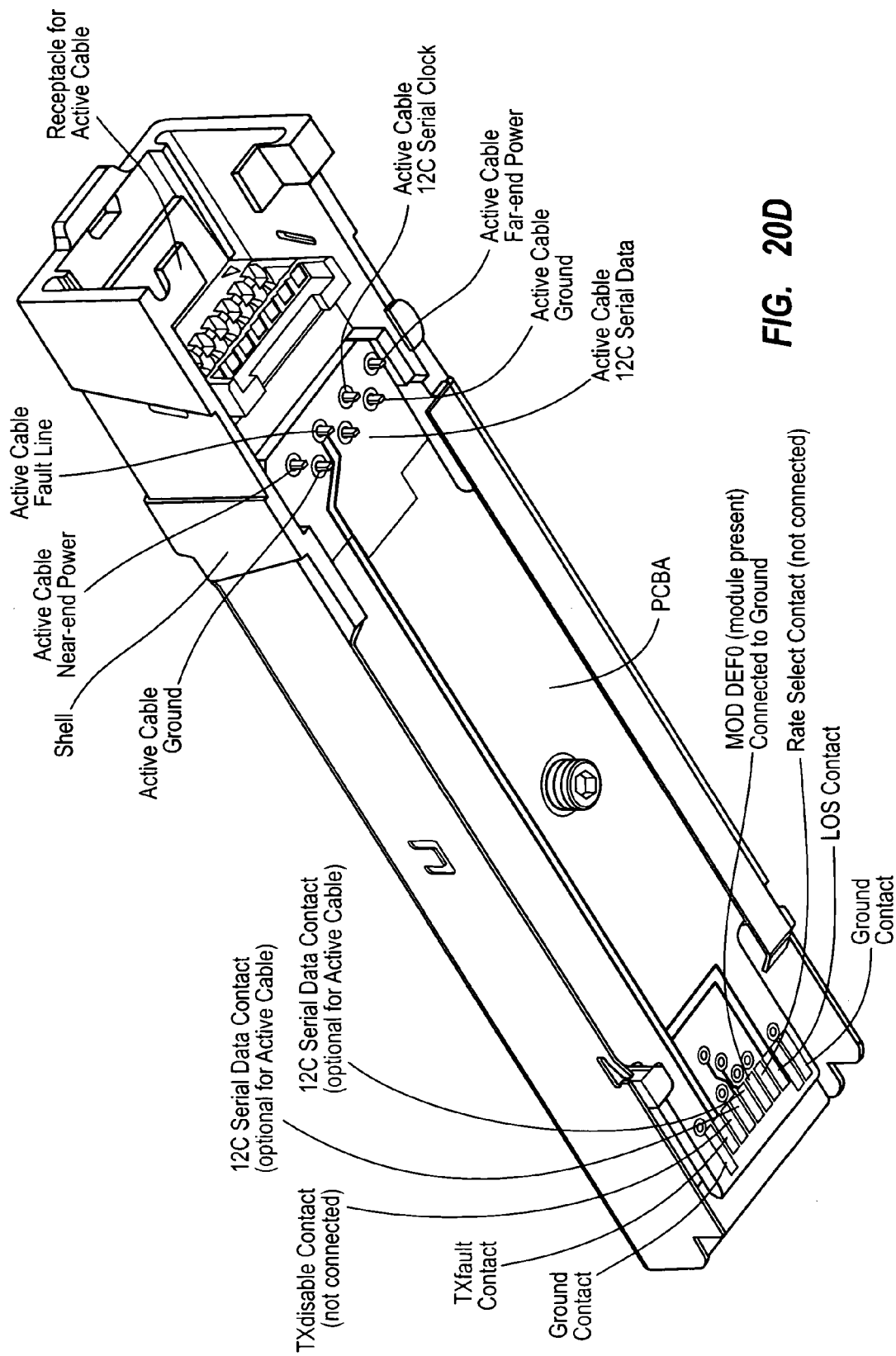
FIG. 20D illustrates a final perspective view of the adaptor of FIG. 20A.
Figure 21:
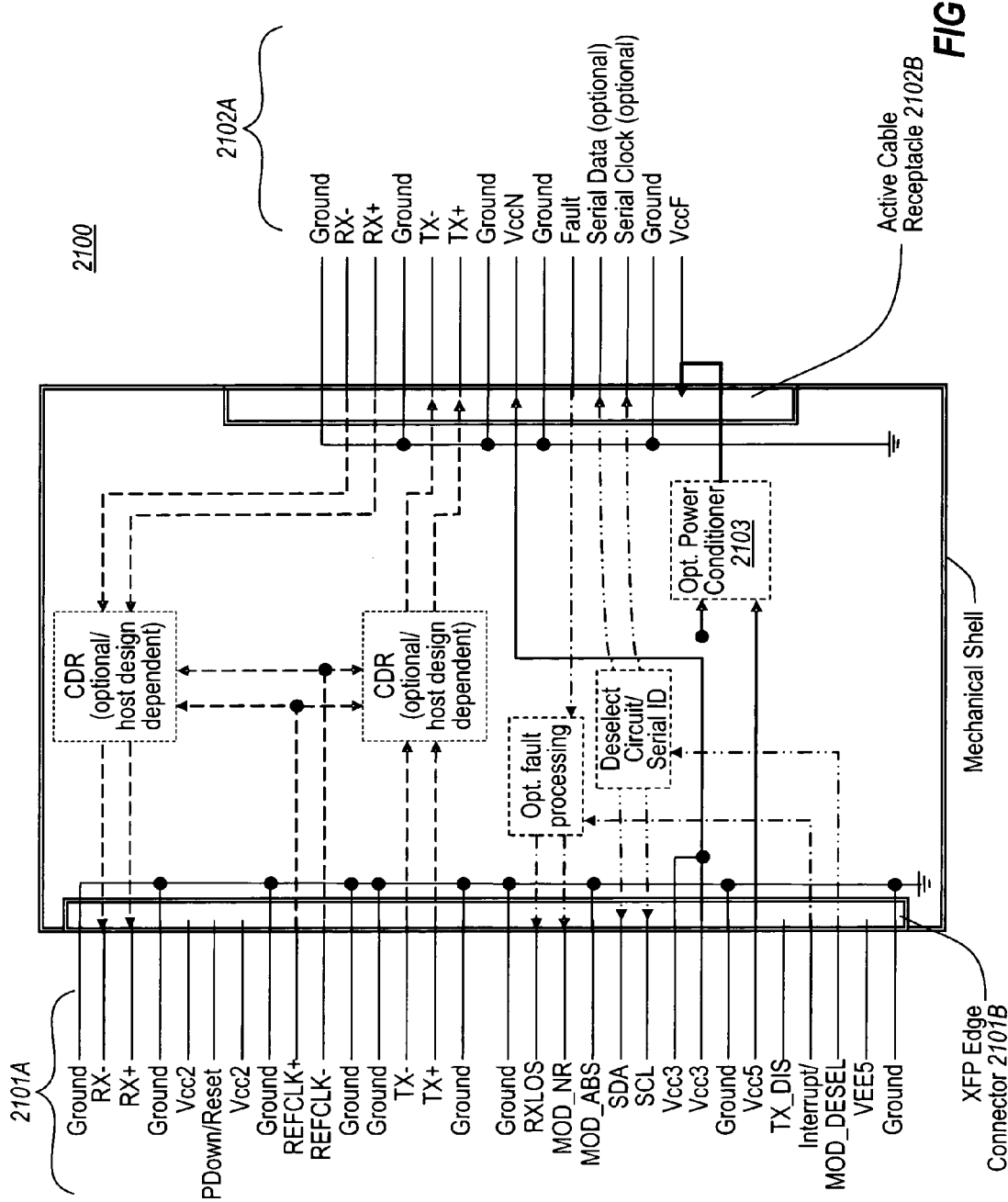
FIG. 21 illustrate an XFP to active cable adaptor electrical conversion mapping component.

FIG. 20C illustrates a top perspective view of the adaptor with more of its shell cut-away to expose the various components on the upper surface of the printed circuit board including electrical traces from the SFP electrical connector, and the signal mapping component 2002. The signal mapping component 2002 mechanically receives the active cable so as to be electrically coupled to the active cable, and is electrically hardwired to the SFP traces. The mapping component 2002 may perform appropriate signal mapping, an example of which being illustrated in FIG. 19. FIG. 20D illustrates a bottom perspective view of the adaptor with more of its shell cut away to expose the various components of the lower surface of the printed circuit board FIG. 21 illustrates a signal mapping diagram of an adaptor 2100 that adapts between the common XFP standard and the active cable signals illustrated with respect to FIG. 15A-15C. On the left side of the adaptor 1500 are the standard XFP signals 2101A coupled to an XFP edge connector abstractly represented by reference number 2102A. On the right of the adaptor 2100 are the active signals 2101B of FIG. 15A-15C coupled to the active cable connector abstractly represented by reference number 2102B. The adaptor 2100 may include an optional power conditioner 2103 if power regulation is needed between the XFP power supply Vcc and the active cable power supply VccF.

The XFP standard requires a retiming function which may be included in the adaptor and is illustrated in FIG. 21 as the two optional CDR blocks. However it may provide a useful cost and power savings to eliminate the retiming function. This may be acceptable if the active cable sufficiently limits jitter because of the choice of fiber, length or any of the number of active jitter reductions described previously, such as jitter precompensation.

Figure 22A:
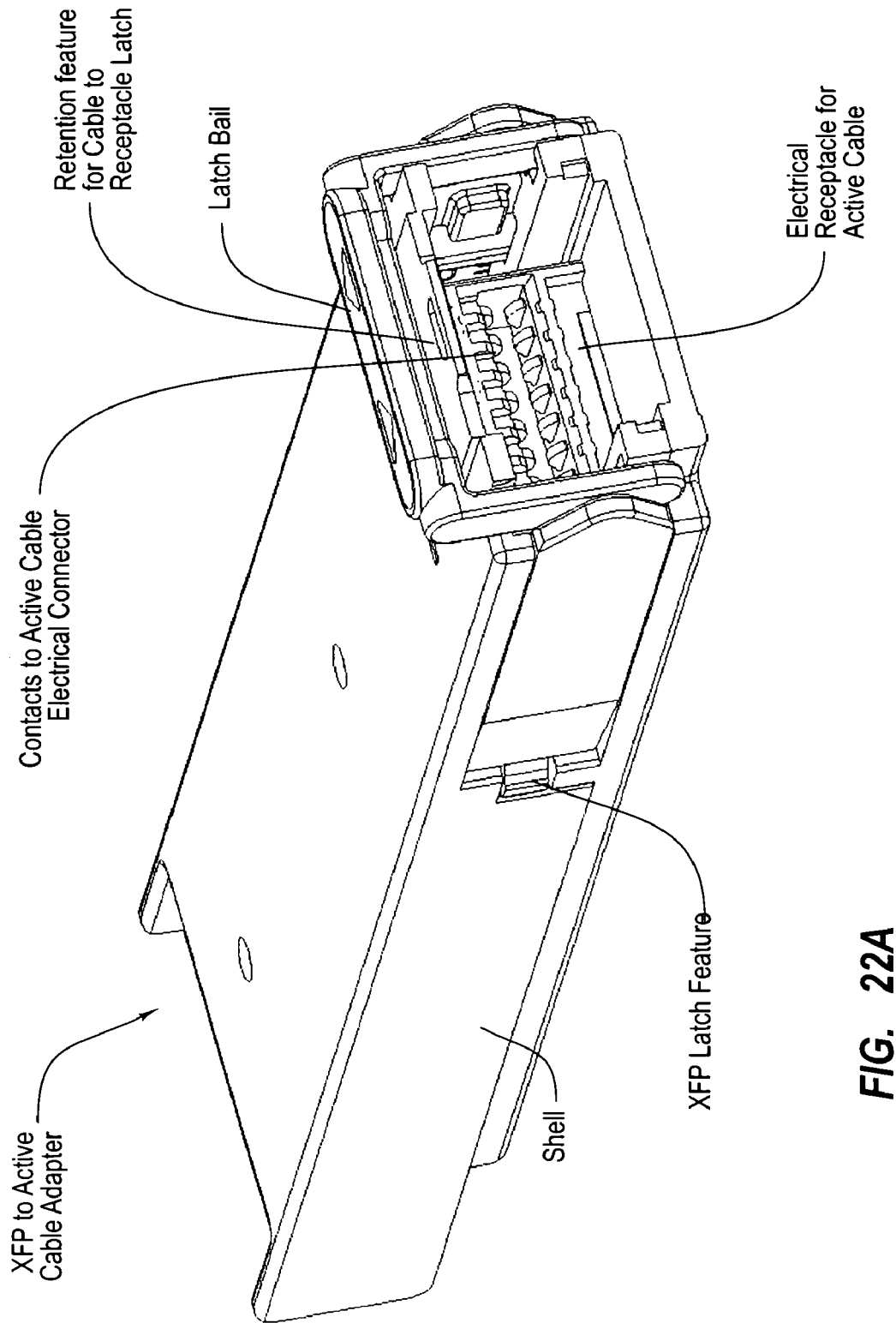
FIG. 22A illustrates a first view of an XFP to active cable adaptor in accordance with one embodiment of the present invention.

FIG. 22A illustrates a view of first embodiment of a mechanical design of an XFP to active cable adapter. The proximate end of the adaptor shows the electrical receptacle for the active cable, with a latch bail to actuate the retention mechanism of the overall adapter (a standard feature of the XFP mechanical interface, which in this illustration is implemented as two sliding latch features on the sides, only one of which is visible). A separate latch mechanism (shown only as a small catch in the view FIG. 22A) is provided for retaining the cable to the adaptor. Several contacts are shown which contact the respective electrical traces of the active cable end when the active cable is inserted into its corresponding electrical receptacle on the adaptor.

Figure 22B:
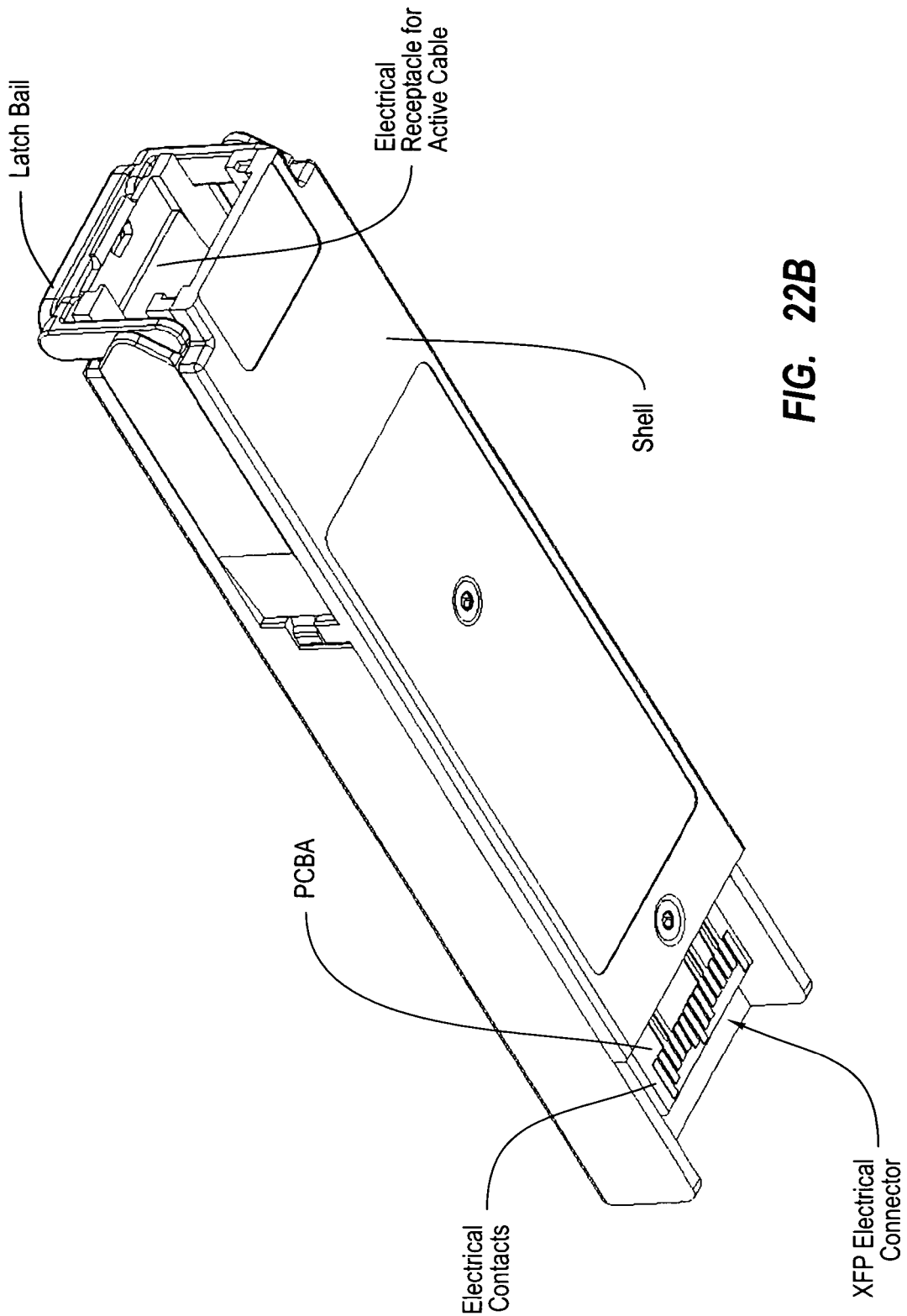
FIG. 22B illustrates another perspective view of the adaptor of FIG. 22A.

FIG. 22B illustrates another perspective view of the design of the adaptor in FIG. 16A. This view shows part of the XFP to host interface on the internal PCBA.

Figure 22C:
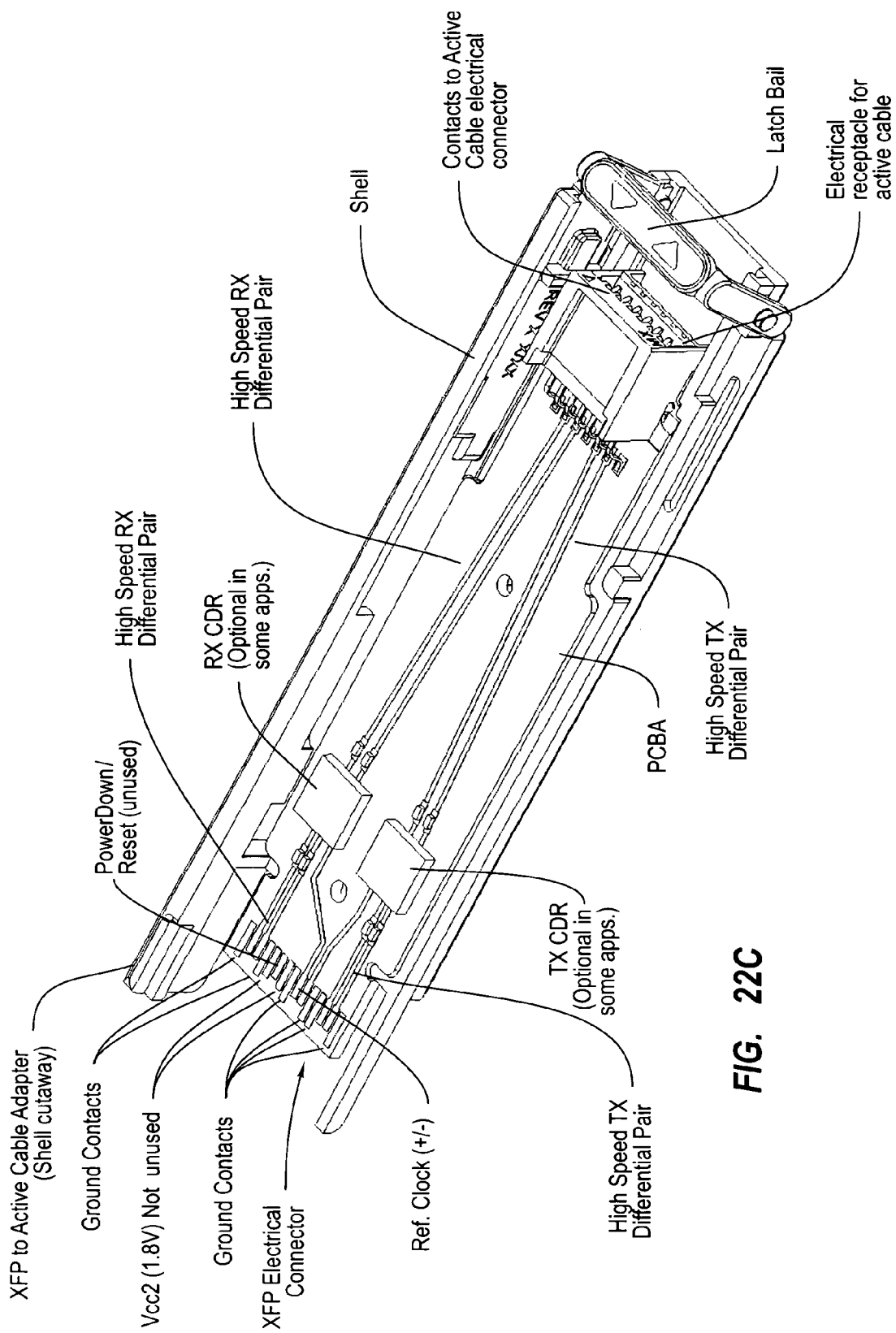
FIG. 22C illustrates yet another perspective view of the adaptor of FIG. 22A.

FIG. 22C illustrates a top perspective with a portion of the shell cut-away to expose features of the internal design, particularly the layout of the top of the PCBA. High speed signals from the XFP edge connector are routed directly to and from a TX and RX CDR respectively. The output of the TX CDR is directly tied to the TX pins of the active cable electrical receptacle. Similarly, high speed lines from the receive pins of the active cable receptacle are coupled to the RX CDR.

Figure 22D:
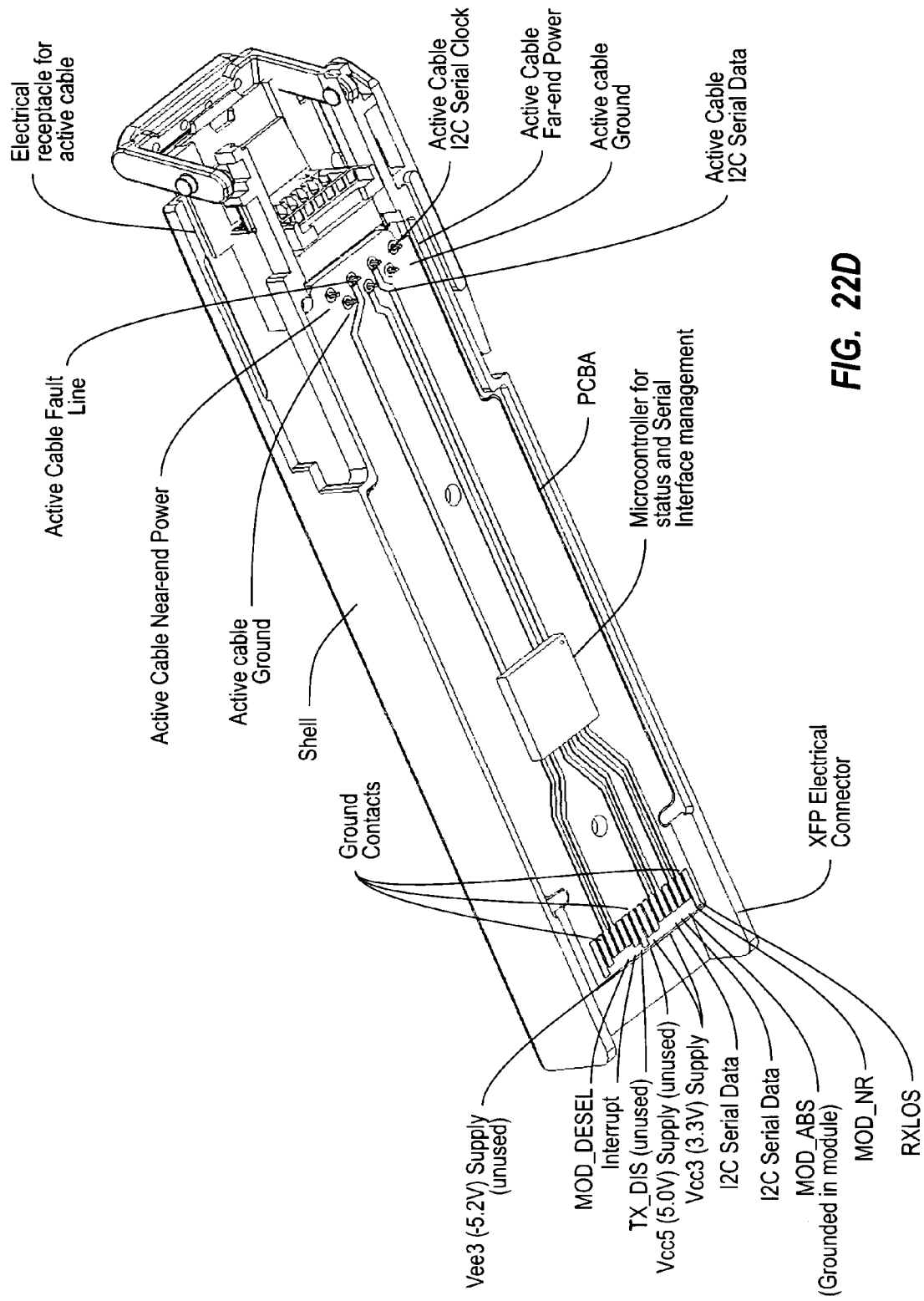
FIG. 22D illustrates a final perspective view of the adaptor of FIG. 22A.

FIG. 22D shows a bottom perspective view of the adapter with the bottom shell cover removed. This view illustrates connection of the various low speed status and control lines through a microcontroller to adapt them to the related signals used by the active cable receptacle while at the same time the expectation of the host system for the responses from these connections. The microcontroller can similarly provide EEPROM to provide an appropriate response to a serial ID query from the host. Also show in FIG. 22D are the various power supply connections for the 3.3V and 5.0V supplies as well as the previously discussed APS supply.

The final type of adaptor discussed is for use in X2 receptacles. The X2 is one of three form factors which implement a XAUI (10 Gigabit Attachment Unit Interface) electrical interface, the other two being the XENPAK and XPAK form factors. The host side electrical interface of these three designs is essentially identical and they differ only in mechanical features.

FIG. 22 illustrates a signal mapping diagram of an X2 to active cable adapter. The main feature of the XAUI interface is that the overall 10 G datastream is carried over four lower speed connections in each direction (labeled as RX+/−0-3 and TX+/−0-3). Because the four XAUI lines uses a different signal coding format than the 10 G serial connections, the actual transition rate is somewhat higher than a quarter of the rate of the serial interface. In addition to the parallel electrical interface, the XAUI standard requires jitter reduction, retiming and recoding the signals before transmission as a signal, as vary as a wide range of low speed control and monitoring signals. Presently, most of these features have been implemented in a single IC commonly known as a XAUI SERDES (serialiser-deserialiser) and shown in FIG. 17

Figure 23:
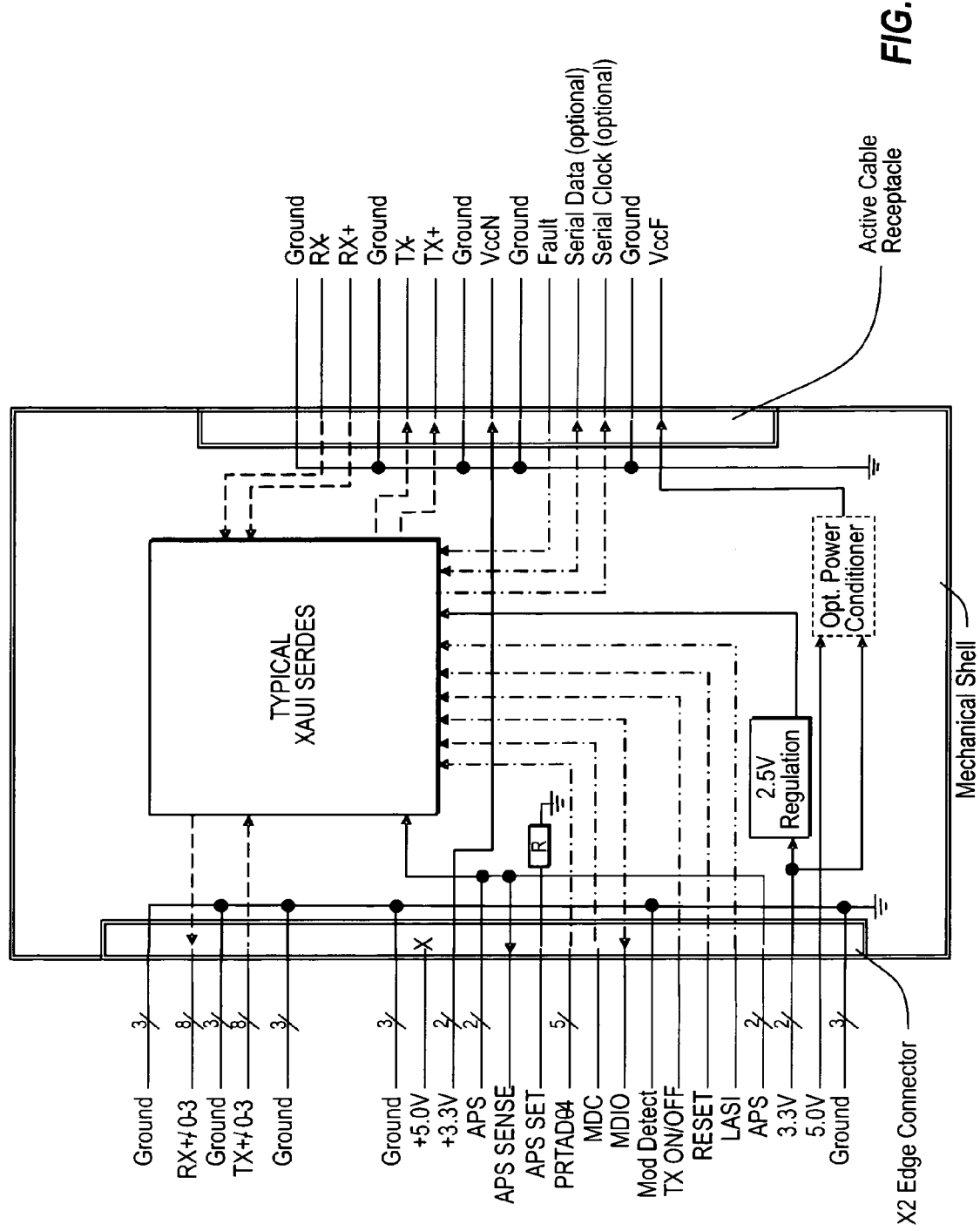
FIG. 23 illustrate an X2 to active cable adaptor electrical conversion mapping component.

Another feature of the XAUI interface is an adjustable power supply, labeled APS on the pin connections in FIG. 23. This special connection is for an adjustable power supply pn the host system for which the voltage is set by a resistor to ground inside the X2 module (or in this case adapter) connected to a pin labeled APS SET. A third related pin labeled APS sense carries an internal measurement of the APS voltage back to the host system as part of the voltage control feedback loop. In the present embodiment, this adjustable power supply is only used for powering the XAUI SERDES itself, typically a low voltage CMOS IC.

Figure 24A:
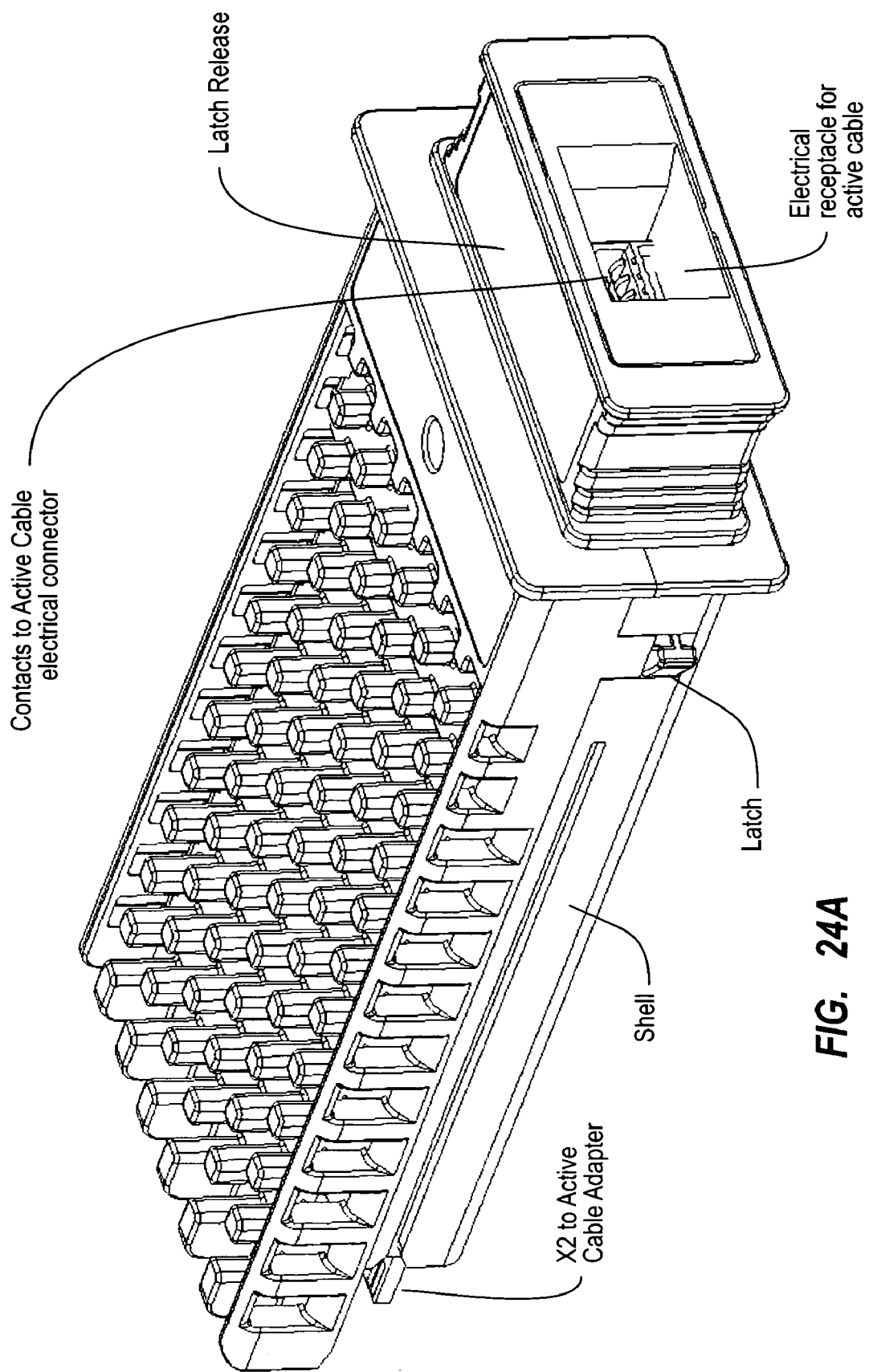
FIG. 24A illustrates a first view of an X2 to active cable adaptor in accordance with one embodiment of the present invention.

FIG. 24A illustrates a view of first embodiment of a mechanical design of an X2 to active cable adapter. The proximate end of the adaptor shows the electrical receptacle for the active cable, with a latch release to actuate the retention mechanism of the overall adapter (a standard feature of the X2 mechanical interface, which in this illustration is implemented as two retracting latch features on the sides, only one of which is visible). A separate latch mechanism, (not shown) is provided for retaining the cable to the adaptor. Several contacts are shown which contact the respective electrical traces of the active cable end when the active cable is inserted into its corresponding electrical receptacle on the adaptor.

Figure 24B:
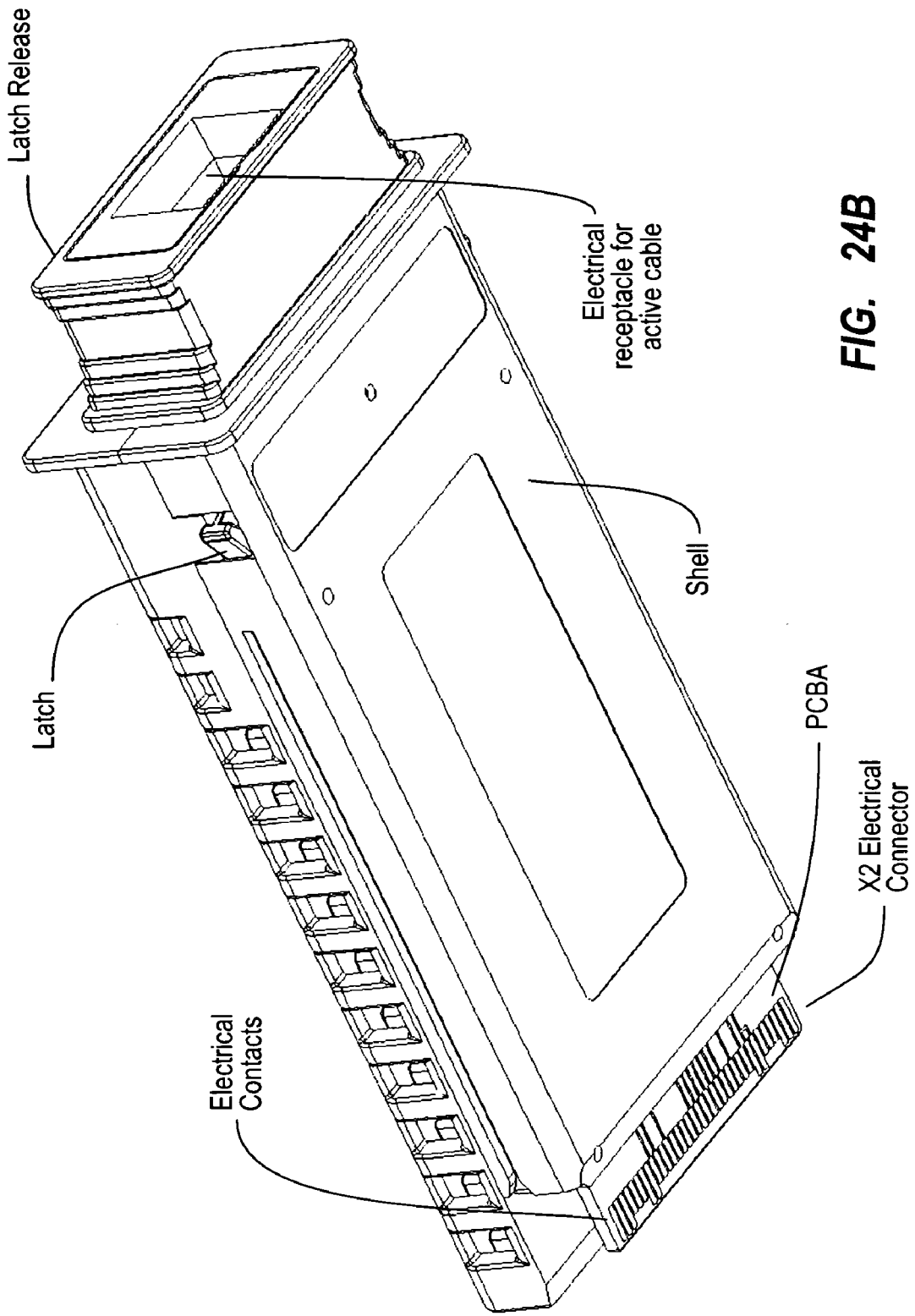
FIG. 24B illustrates another perspective view of the adaptor of FIG. 24A.

FIG. 24B illustrates another perspective view of the design of the adaptor in FIG. 24A. This view shows part of the X2 to host interface on the internal PCBA.

Figure 24C:
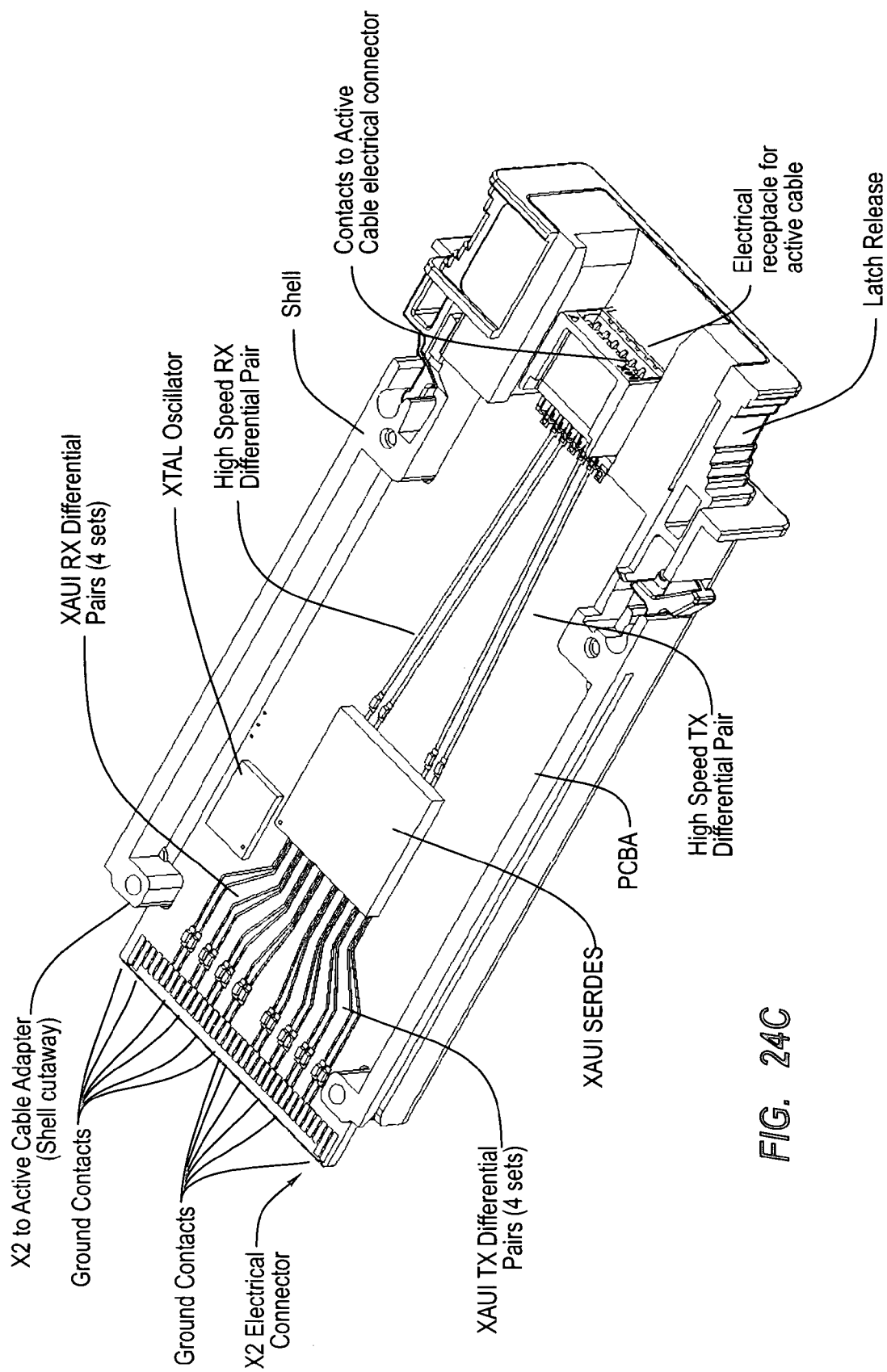
FIG. 24C illustrates yet another perspective view of the adaptor of FIG. 24A.
Figure 24D:
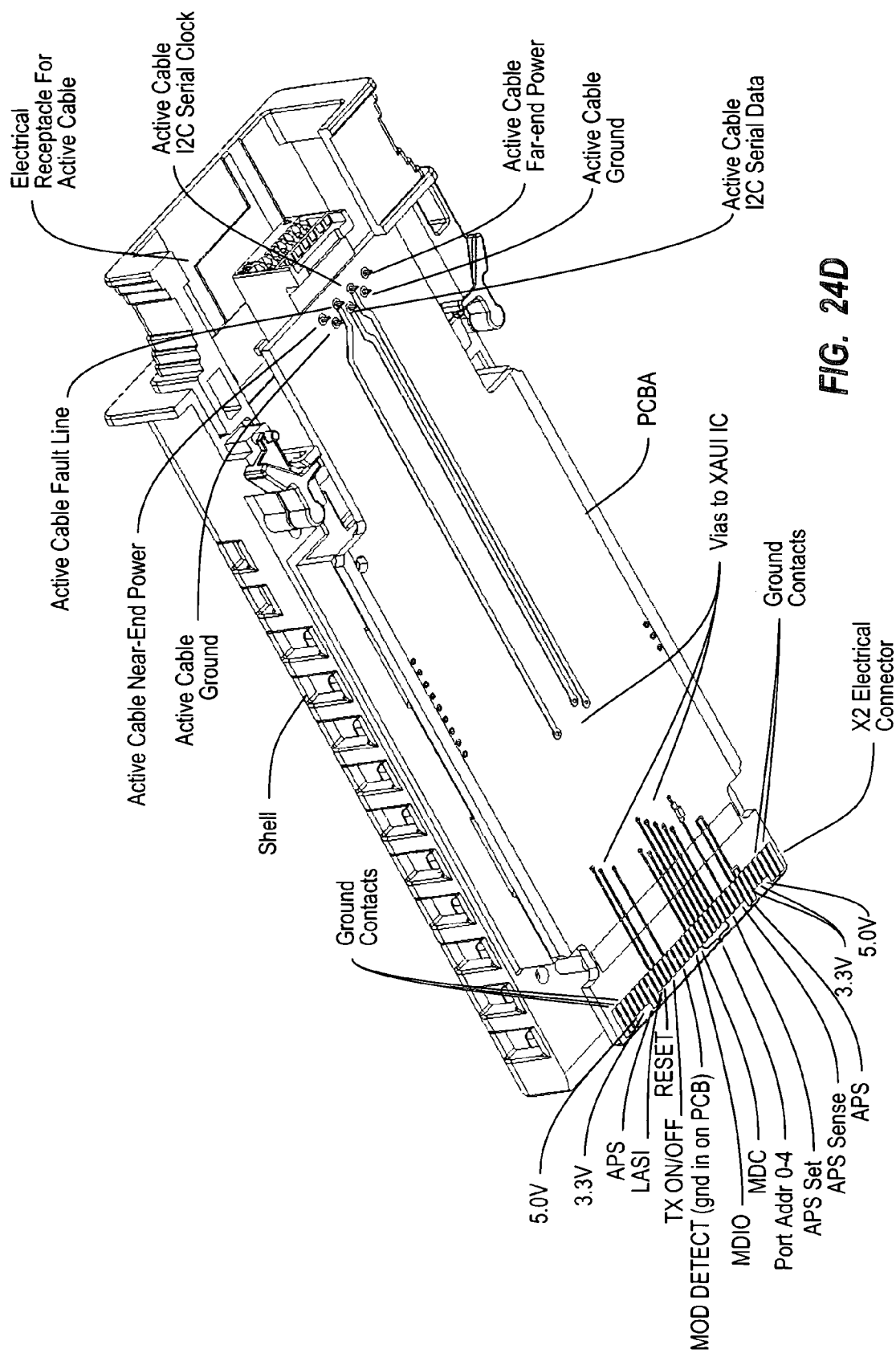
FIG. 24D illustrates a final perspective view of the adaptor of FIG. 24A.

FIG. 24C illustrates a top perspective with a portion of the shell cut-away to expose features of the internal design, particularly the layout of the top of the PCBA. Four sets of XAUI signal differential pairs are routed in each direction from the X2 edge connector are routed directly to and from the XAUI SERDES. The TX output of the XAUI SERDES is directly tied to the TX pins of the active cable electrical receptacle. Similarly, high speed lines from the receive pins of the active cable receptacle are coupled to the RX input of the XAUI SERDES. Also shown in FIG. 24 is a crystal oscillator (labeled XTAL). This is normally required to provide the timing basis of the transmitted serial signal.

FIG. 24 shows a bottom perspective view of the adapter with the bottom shell cover removed. This view illustrates connection low speed status and control lines to and from the XAUI SERDES which used to adapt them to the related signals used by the active cable receptacle while at the same time the expectation of the host system for the responses from these connections. The SERDES will provide an interface to EEPROM to provide an appropriate response to a serial ID query from the host. Also show in FIG. 24D are the various power supply connections for the 3.3V and 5.0V supplies as well as the previously discussed APS supply.

Accordingly, an active cable is described in which an electrical connection is provided on at least one side of the cable to receive the high speed electrical signal, while having the signal being communicated optically through most of the cable length. An adaptor for adapting between SFP, XFP or X2 and the active cable connector has also been described.

The present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. An integrated cable comprising:
   a first optical fiber within the integrated cable;
   a first opto-electrical transducer within the integrated cable and coupled to a first end of the first optical fiber such that when a first optical signal is present on the first optical fiber, the first opto-electrical transducer receives the first optical signal and converts the first optical signal into a first electrical signal;
   a first electrical connector integrated with the integrated cable and coupled to the first opto-electrical transducer such that when the first optical signal is received by the first opto-electrical transducer, the first electrical connector receives the first electrical signal, wherein the first electrical connector is sized to connect with a first electrical port external to the cable such that when connected to the first electrical port and when the first electrical signal is present on the first electrical connector, the first electrical signal is provided to the first electrical port;
   a retiming mechanism for supporting retiming of an input high speed electrical signal to reduce total link jitter in the integrated cable; and
   a mechanism for providing host selectable pre-emphasis of an output high speed electrical signal to reduce total link jitter, wherein the level of pre-emphasis is host adjustable via a serial interface of the integrated cable.

2. An integrated cable in accordance with claim 1, further comprising:
   a protective coating configured to surround the first optical fiber, the first opto-electrical transducer and at least portions of the first electrical connector.

3. An integrated cable in accordance with claim 1, further comprising:
   a first electro-optical transducer within the integrated cable and coupled to the first electrical connector such that when a second electrical signal is applied to the first electrical connector, the first electro-optical transducer receives the second electrical signal and converts the second electrical signal into a second optical signal; and
   a second optical fiber within the integrated cable and coupled to the first electro-optical transducer such that when the second electrical signal is present on the first electrical connector, the second optical fiber receives the second optical signal from the first electro-optical transducer at a first end of the second optical fiber.

4. An integrated cable in accordance with claim 3, further comprising:
   a first optical connector coupled to a second end of the first optical fiber; and
   a second optical connector coupled to a second end of the second optical fiber.

5. An integrated cable in accordance with claim 4, wherein the first and second optical connector form part of the same piece.

6. An integrated cable in accordance with claim 3, further comprising:
   a second opto-electrical transducer within the integrated cable and coupled to a second end of the second optical fiber such that when a third optical signal is present on the second optical fiber, the second opto-electrical transducer receives the third optical signal and converts the third optical signal into a third electrical signal;
   a second electrical connector integrated with the integrated cable and coupled to the second opto-electrical transducer such that when the third optical signal is received by the second opto-electrical transducer, the second electrical connector receives the third electrical signal, wherein the second electrical connector is sized to connect with a second electrical port external to the cable such that when connected to the second electrical port and when the third electrical signal is present on the second electrical connector, the third electrical signal is provided to the second electrical port; and
   a second electro-optical transducer within the integrated cable and coupled to the second electrical connector such that when a fourth electrical signal is applied to the second electrical connector, the second electro-optical transducer receives the fourth electrical signal and converts the fourth electrical signal into a fourth optical signal,
   wherein the first optical fiber is coupled to the second electro-optical transducer such that when the fourth electrical signal is present on the second electrical connector, the first optical fiber receives the fourth optical signal from the second electro-optical transducer at a second end of the first optical fiber.

7. An integrated cable in accordance with claim 1, wherein the integrated cable supports data rates of between 1 to 11.5 gigabits per second, inclusive.

8. An integrated cable in accordance with claim 1, wherein a length of the integrated cable is between 1 and 30 meters.

9. An integrated cable in accordance with claim 1, further comprising:
a mechanism for providing host selectable equalization of the input high speed electrical signal to reduce total link jitter.

10. An integrated cable in accordance with claim 1, further comprising:
a mechanism that provides preemphasis of an output high speed electrical signal to reduce total link jitter.

11. An integrated cable in accordance with claim 1, wherein the integrated cable supports predefined limits of added deterministic and total jitter of a high speed signal.

12. An integrated cable in accordance with claim 11, wherein the predefined limits of added deterministic and total jitter are chosen to allow concatenation of up to 3 cables.

13. An integrated cable in accordance with claim 1, wherein the integrated cable has an optical connection at a second end of the integrated cable to thereby form a first E-O cable, the integrated cable being part of a sequence of cables including the first E-O cable at a first end of the sequence, a second E-O cable at the second end of the sequence, and one or more optical cables between the first and second E-O cables.

14. An integrated cable in accordance with claim 1, wherein the integrated cable has an optical connection at a second end of the integrated cable, wherein the optical connection is sized to be coupled to an optical transceiver.

15. An integrated cable in accordance with claim 1, wherein the integrated cable has a second electrical connector at a second end of the integrated cable to thereby form a first E-E cable, the electrical connection being sized to connect with a receptacle of a cable plug end adaptor.

16. An integrated cable in accordance with claim 1, wherein the integrated cable has a second electrical connector at a second end of the integrated cable to thereby form a first E-E cable, the first electrical connector being a male connector, and second electrical connector being a female connector configured to receive an electrical connector that is sized and shaped the same as the first electrical connector.

17. An integrated cable comprising:
a first optical fiber within the integrated cable;
a first opto-electrical transducer within the integrated cable and coupled to a first end of the first optical fiber such that when a first optical signal is present on the first optical fiber, the first opto-electrical transducer receives the first optical signal and converts the first optical signal into a first electrical signal;
a first electrical connector integrated with the integrated cable and coupled to the first opto-electrical transducer such that when the first optical signal is received by the first opto-electrical transducer, the first electrical connector receives the first electrical signal, wherein the first electrical connector is sized to connect with a first electrical port external to the cable such that when connected to the first electrical port and when the first electrical signal is present on the first electrical connector, the first electrical signal is provided to the first electrical port; and
a mechanism for supporting adaptive equalization of an input high speed electrical signal to reduce total link jitter in the integrated cable;
a retiming mechanism for supporting retiming of an input high speed electrical signal to reduce total link jitter in the integrated cable;
an electrical conductor configured to carry electrical power to the cable end; and
means for converting down the electrical power to power at least the retiming mechanism.

18. An integrated cable in accordance with claim 17, wherein the equalization is configured to compensate for high frequency rolloff of the host's traces.

19. An integrated cable in accordance with claim 17, wherein the equalization is configured to compensate for the integrated cable's high frequency rolloff.

20. An integrated cable in accordance with claim 17, wherein the equalization is automatically adaptive to host impairments.

21. An integrated cable in accordance with claim 17, wherein the power is at least 40 volts.

* * * * *